US012642531B2

(12) United States Patent
Shelton, IV et al.

(10) Patent No.:  US 12,642,531 B2
(45) Date of Patent:      Jun. 2, 2026

(54) IMPLANTABLE SPHINCTER ASSISTANCE DEVICE WITH DUAL ZONE CONTROLLED RATE OF CONSTRICTION FORCE

(71) Applicant: Cilag GmbH International, Zug (CH)

(72) Inventors: Frederick E. Shelton, IV, Hillsboro, OH (US); Kevin M. Fiebig, Cincinnati, OH (US); Tylor C. Muhlenkamp, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 1118 days.

(21) Appl. No.: 17/552,793

(22) Filed: Dec. 16, 2021

(65) Prior Publication Data

US 2023/0200815 A1      Jun. 29, 2023

(51) Int. Cl.
A61B 17/12          (2006.01)
A61B 17/00          (2006.01)

(52) U.S. Cl.
CPC ................... *A61B 17/12013* (2013.01); *A61B 2017/00477* (2013.01); *A61B 2017/00827* (2013.01);
(Continued)

(58) Field of Classification Search
CPC .... A61B 17/12013; A61B 2017/00477; A61B 2017/00827; A61B 2017/00862; A61B 2017/00876; A61B 2017/00964; A61B 2017/12018; A61B 2017/00893; A61B 2090/0808
See application file for complete search history.

(56) References Cited

U.S. PATENT DOCUMENTS 7,175,589 B2      2/2007  Deem et al.
7,695,427 B2      4/2010  Kugler et al.
(Continued)

FOREIGN PATENT DOCUMENTS

DE          3011742 A1      10/1981
EP          2182885 B1      3/2015

OTHER PUBLICATIONS

Cordon et al. Artificial urinary sphincters for male stress urinary incontinence: current perspectives, 9, 175-183, 2016 (Year: 2016).*
(Continued)

*Primary Examiner* — Christine H Matthews
*Assistant Examiner* — Brooke Nicole Kohutka
(74) *Attorney, Agent, or Firm* — FBT Gibbons LLP

(57) ABSTRACT

An apparatus includes a plurality of beads. Each bead includes a housing and a magnet positioned within the housing. The apparatus also includes a plurality of interconnection elements. Each interconnection element movably joins together a corresponding pair of beads. The plurality of beads and the plurality of interconnection elements are sized and configured to form an expandable loop around an anatomical structure in a patient. The expandable loop is configured to apply a constrictive force to the anatomical structure. The constrictive force has a first rate of change when a dilation ratio of the expandable loop is within a first range, a second rate of change when the dilation ratio of the expandable loop is within a second range, and a third rate of change when the dilation ratio of the expandable loop is within a third range.

16 Claims, 40 Drawing Sheets

(52) U.S. Cl.
CPC .............. *A61B 2017/00862* (2013.01); *A61B 2017/00876* (2013.01); *A61B 2017/00964* (2013.01); *A61B 2017/12018* (2013.01)

(56) References Cited

U.S. PATENT DOCUMENTS

| | | | |
|---|---|---|---|
| 8,070,670 | B2 | 12/2011 | Deem et al. |
| 8,734,475 | B2 | 5/2014 | Ekvall et al. |
| 8,870,898 | B2 | 10/2014 | Beisel et al. |
| 10,245,133 | B2 | 4/2019 | Alharmi et al. |
| 10,405,865 | B2 | 9/2019 | Shelton, IV et al. |
| 10,517,600 | B2 | 12/2019 | Beisel et al. |
| 10,543,074 | B2 | 1/2020 | Frigstad et al. |
| 10,716,570 | B2 | 7/2020 | Shelton, IV et al. |
| 10,813,737 | B2 | 10/2020 | Auld et al. |
| 10,828,064 | B2 | 11/2020 | Flakne et al. |
| 10,842,496 | B2 | 11/2020 | Shelton, IV et al. |
| 10,945,738 | B2 * | 3/2021 | Auld ................. A61B 17/12013 |
| 11,071,619 | B2 | 7/2021 | Shelton, IV et al. |
| 11,076,856 | B2 | 8/2021 | Kopelman |
| 11,207,173 | B2 | 12/2021 | Popescu |
| 11,298,136 | B2 | 4/2022 | Shelton, IV et al. |
| 11,350,946 | B2 | 6/2022 | Dobashi et al. |
| 11,399,928 | B2 | 8/2022 | Shelton, IV et al. |
| 11,478,347 | B2 | 10/2022 | Fiebig et al. |
| 2004/0225361 | A1 * | 11/2004 | Glenn ..................... A61F 2/442 623/17.12 |
| 2005/0197715 | A1 | 9/2005 | Kugler et al. |
| 2009/0062824 | A1 * | 3/2009 | Berg ........................ A61F 5/005 600/12 |
| 2009/0171378 | A1 * | 7/2009 | Coe ........................ A61F 5/0056 606/157 |
| 2011/0098731 | A1 * | 4/2011 | Whitbrook ............ A61F 2/0018 606/151 |
| 2012/0022324 | A1 * | 1/2012 | Forsell ...................... A61F 2/26 600/40 |
| 2014/0088342 | A1 | 3/2014 | Djurovic |
| 2017/0112650 | A1 | 4/2017 | Hingston et al. |
| 2017/0252141 | A1 * | 9/2017 | Alharmi .............. A61B 5/6874 |
| 2019/0274687 | A1 | 9/2019 | Wang et al. |
| 2020/0323530 | A1 * | 10/2020 | Sharma ................ A61B 18/082 |
| 2023/0190287 | A1 | 6/2023 | Shelton, IV et al. |
| 2023/0190288 | A1 | 6/2023 | Shelton, IV et al. |
| 2023/0190289 | A1 | 6/2023 | Shelton, IV et al. |

OTHER PUBLICATIONS

Kobelev, Vladimir, Fundamentals of Springs Mechanics, Third Edition, 2018 (Year: 2018).*
U.S. Appl. No. 17/552,469.
U.S. Appl. No. 17/552,474.
U.S. Appl. No. 17/552,477.
U.S. Appl. No. 17/552,481.
U.S. Appl. No. 17/552,483.
U.S. Appl. No. 17/552,485.
U.S. Appl. No. 17/552,488.
U.S. Appl. No. 17/552,494.
U.S. Appl. No. 17/552,780.
U.S. Appl. No. 17/552,800.
U.S. Appl. No. 17/552,810.
U.S. Appl. No. 17/552,796.
U.S. Appl. No. 17/552,502.
U.S. Appl. No. 17/552,503.
U.S. Appl. No. 17/552,506.
U.S. Appl. No. 17/552,508.
U.S. Appl. No. 17/552,510.
U.S. Appl. No. 17/552,514.
U.S. Appl. No. 17/552,520.
U.S. Appl. No. 17/552,522.

* cited by examiner

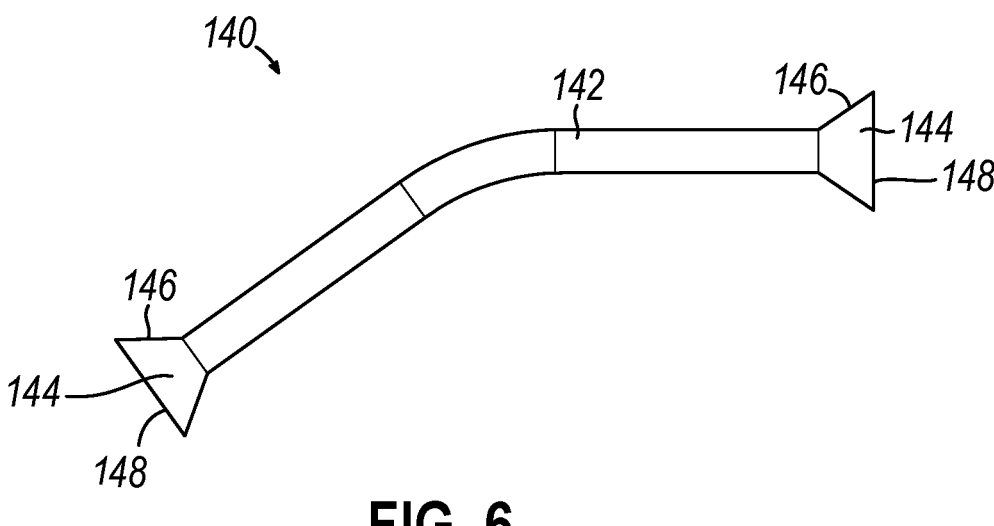
FIG. 6
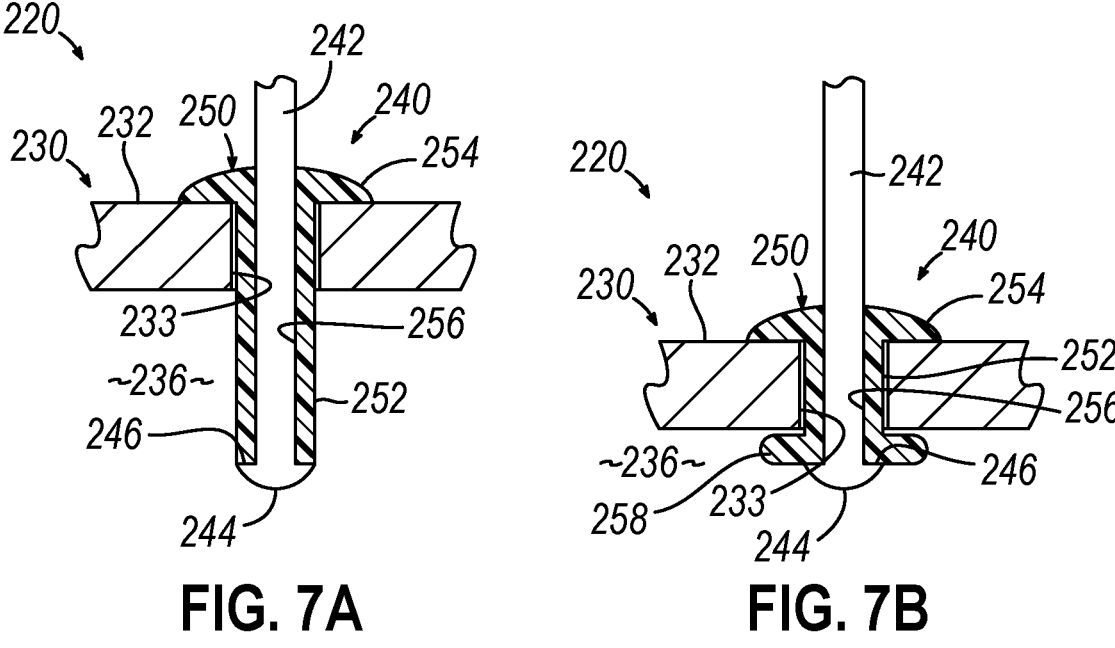
FIG. 7A          FIG. 7B

IMPLANTABLE SPHINCTER ASSISTANCE DEVICE WITH DUAL ZONE CONTROLLED RATE OF CONSTRICTION FORCE

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which effects the esophagus.

A normal, healthy, esophagus is a muscular tube that carries food from the mouth, through the chest cavity and into the upper part of the stomach. A small-valved opening in the esophagus, called the lower esophageal sphincter ("LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes the stomach relative to the lower esophagus; or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein, in its entirety; U.S. Pat. No. 7,695,427, entitled "Methods and Apparatus for Treating Body Tissue Sphincters and the Like," issued Apr. 13, 2010, the disclosure of which is incorporated by reference herein, in its entirety; U.S. Pat. No. 8,070,670, entitled "Methods and Devices for Luminal and Sphincter Augmentation," issued Dec. 6, 2011, the disclosure of which is incorporated by reference herein, in its entirety; and U.S.

Pat. No. 8,734,475, entitled "Medical Implant with Floating Magnets," issued May 27, 2014, the disclosure of which is incorporated by reference herein, in its entirety.

While various kinds and types of instruments have been made and used to treat or otherwise engage anatomical lumens, it is believed that no one prior to the inventors has made or used an invention as described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts a top plan view of an exemplary link for use with the sphincter augmentation device of FIG. 3, showing the link having a pair of flared flat heads;

FIG. 7A depicts a top, cross-sectional view of a portion of another sphincter augmentation device having a link including a rivet, showing a shaft of the rivet in an undeformed state;

FIG. 7B depicts a top, cross-sectional view of a portion of the sphincter augmentation device of FIG. 7A, showing the shaft of the rivet in a deformed state to deploy a shop head for securing the link to a bead of the sphincter augmentation device;

Figure 33A:
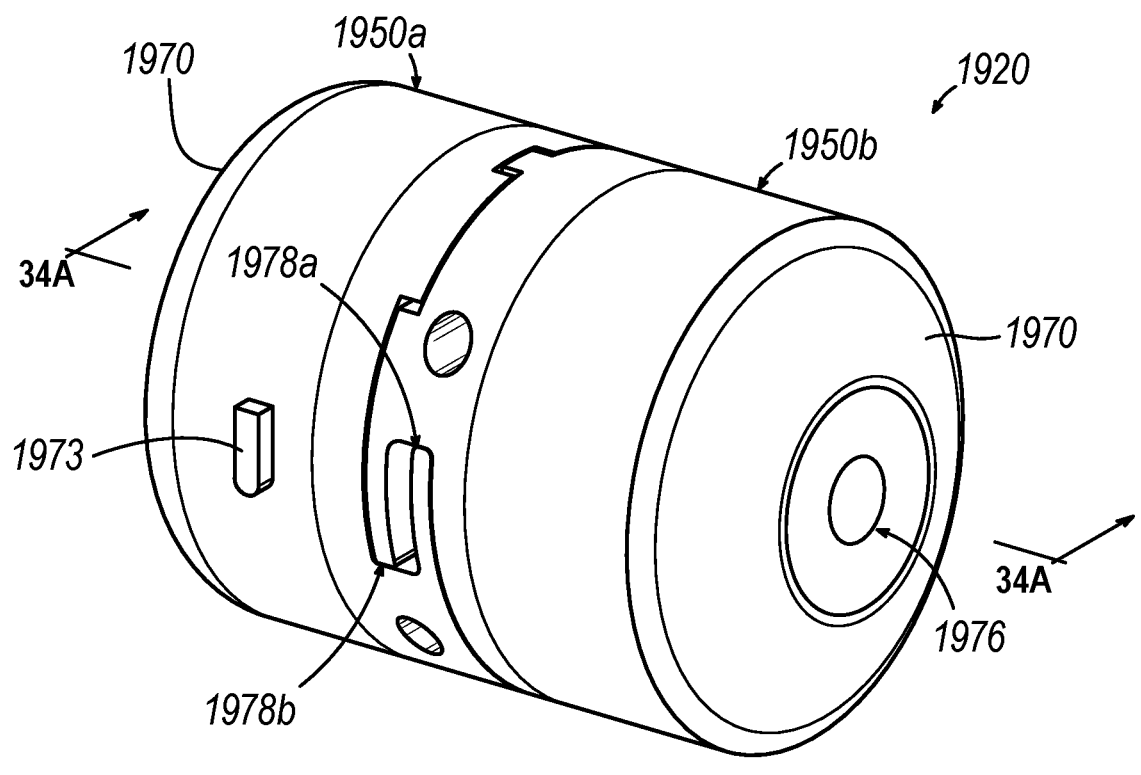
FIG. 33A depicts a perspective view of a portion of another exemplary sphincter augmentation device, showing
Figure 33B:
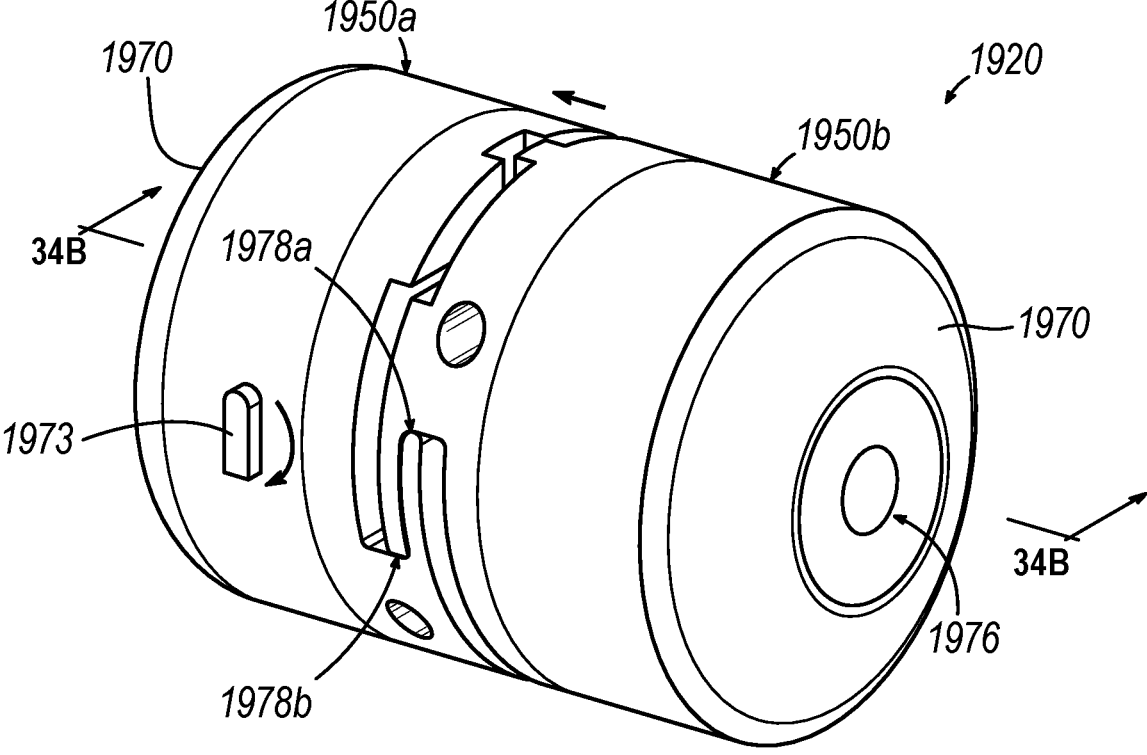
Figure 34A:
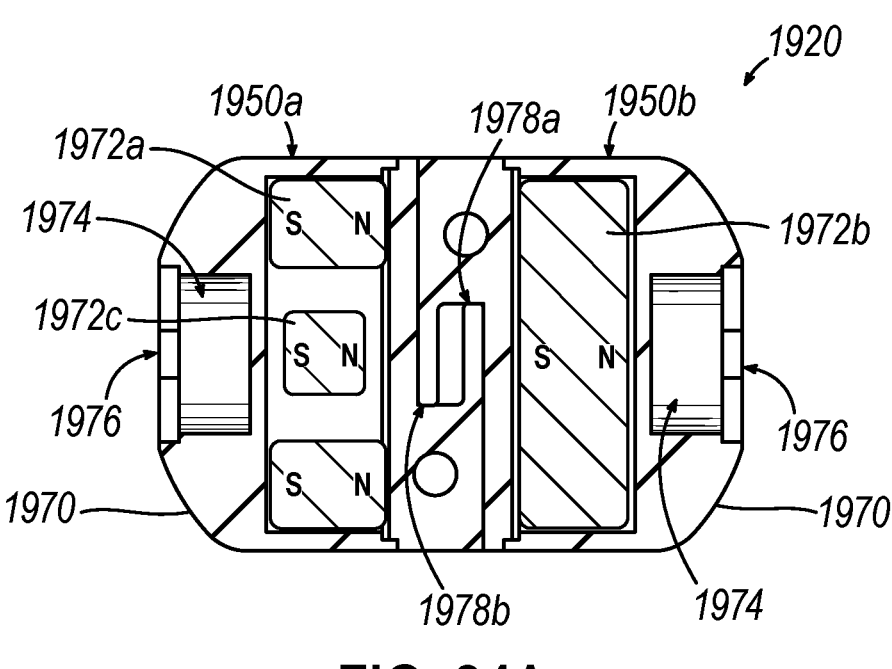
Figure 34B:
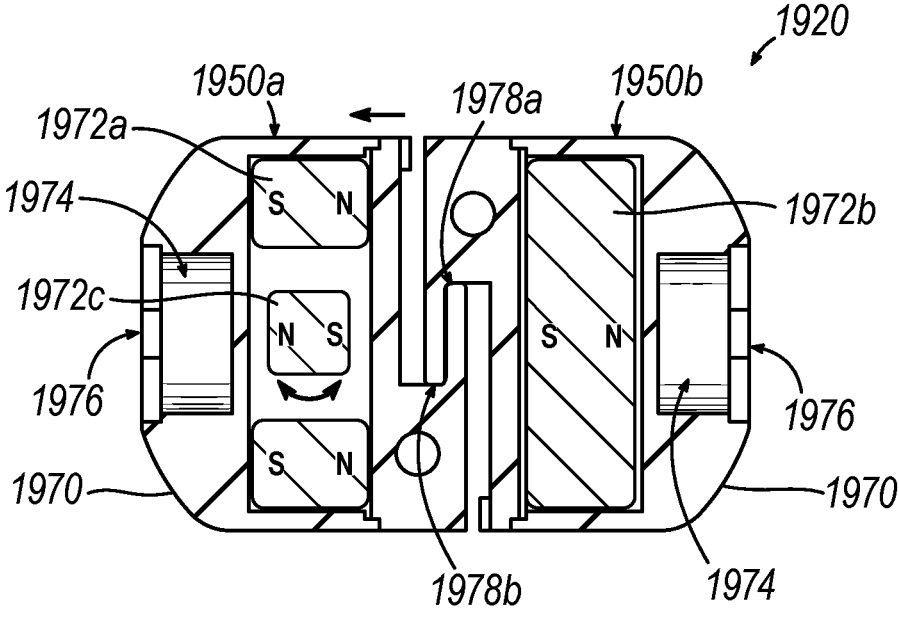
Figure 35:
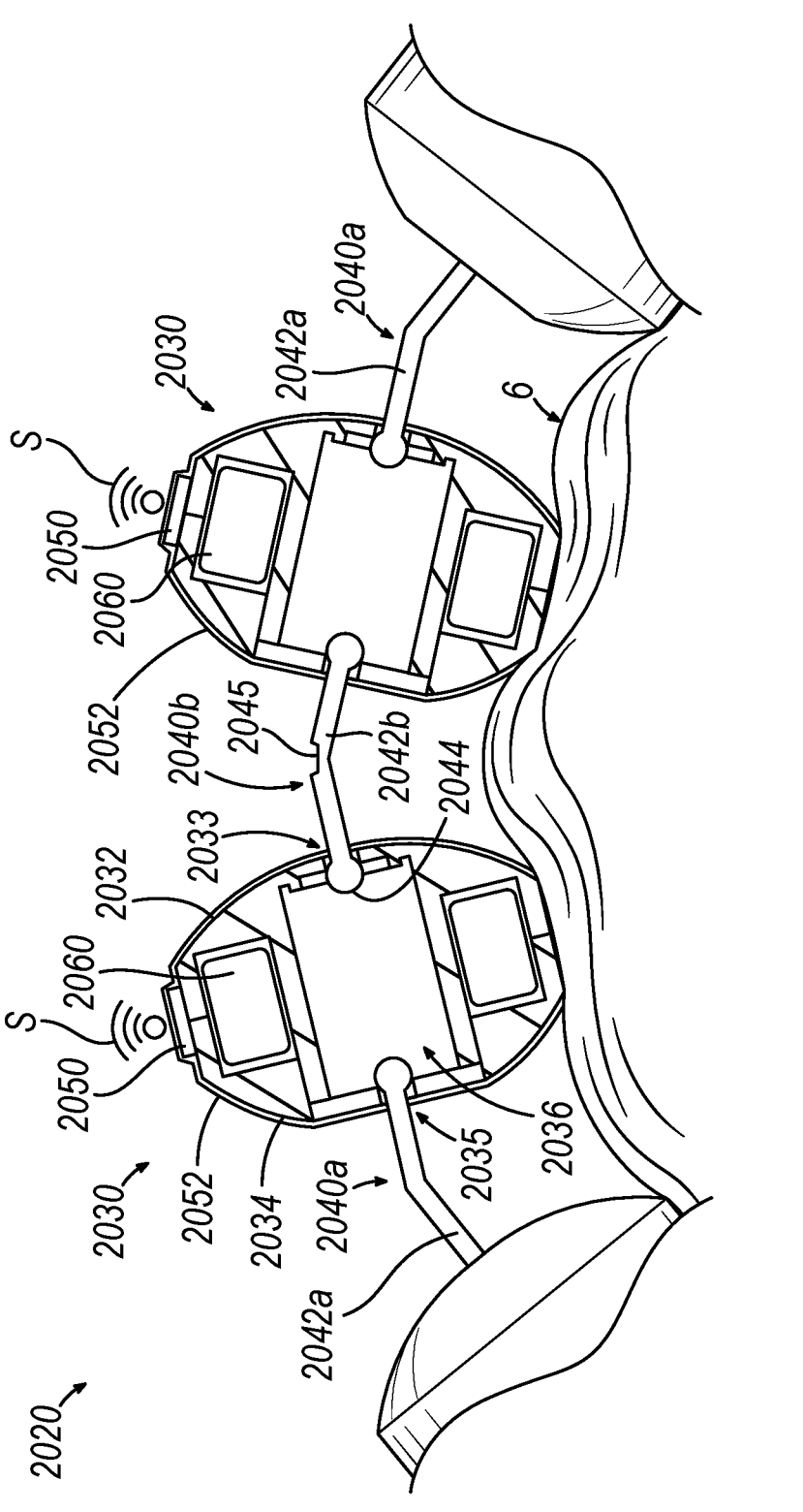
Figure 36:
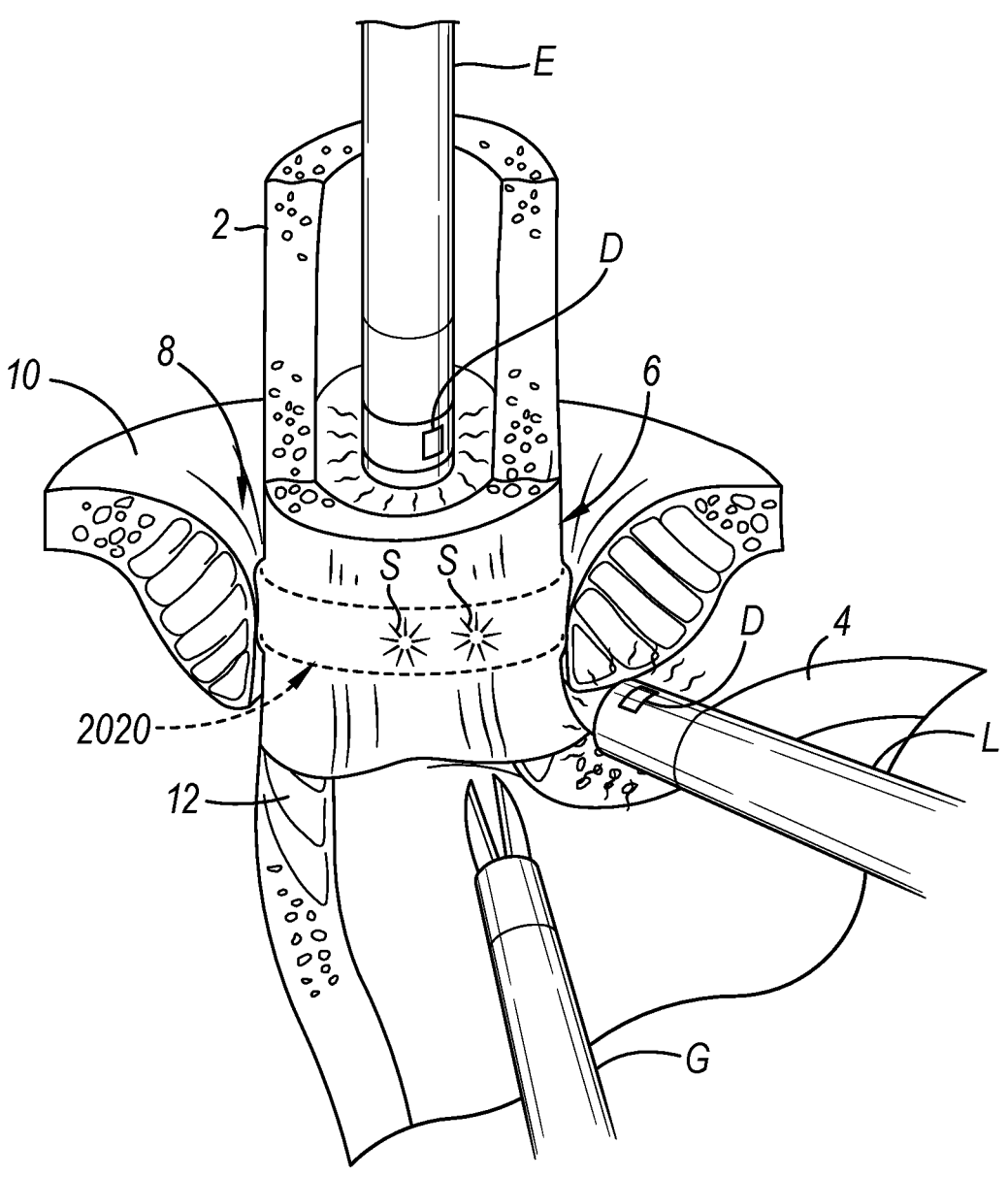

5 a clasp structure of the device having a knob configured to rotate a rotatable magnet of the clasp structure for selectively attracting and repelling a magnet of another clasp structure of the device, showing the knob in a first position such that the rotatable magnet attracts the magnet of the other clasp structure;

FIG. 33B depicts a perspective view of the portion of the sphincter augmentation device of FIG. 33A, showing the knob in a second position such that the rotatable magnet repels the magnet of the other clasp structure;

FIG. 34A depicts a cross-sectional view of the portion of the sphincter augmentation device of FIG. 33A, taken along section line 34A-34A in FIG. 33A;

FIG. 34B depicts a cross-sectional view of the portion of the sphincter augmentation device of FIG. 33A, taken along section line 34B-34B in FIG. 33B;

FIG. 35 depicts a top, cross-sectional view of a portion of another exemplary sphincter augmentation device, showing a link of the device having a breakaway wire with a release notch, and further showing beads of the device that flank the breakaway wire having respective bailout beacons; and FIG. 36 depicts a cross-sectional isometric view, taken along a coronal plane of the body, of a human esophago-gastric junction, showing the sphincter augmentation device of FIG. 35 installed about the LES and visually obscured by tissue overgrowth, and further showing the bailout beacons transmitting signals to detectors of an endoscope and laparoscope for guiding graspers toward the release notch.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Example of Sphincter Augmentation Device

Figure 1:
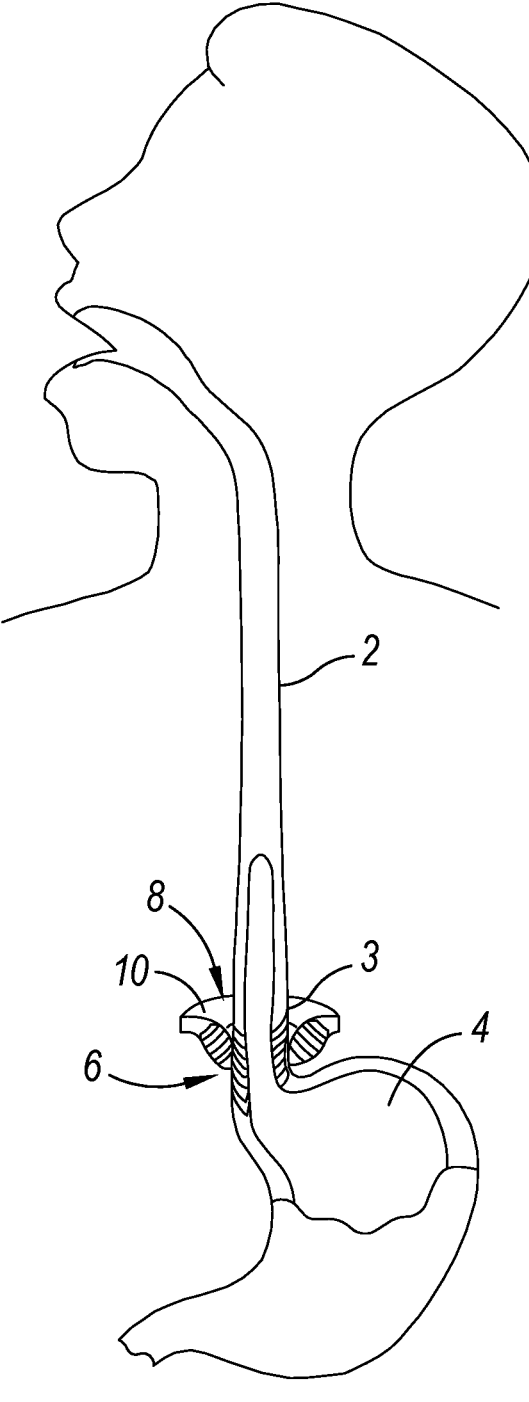
FIG. 1 depicts a cross-sectional side view, taken along a coronal plane of the body, of a biological passage.
Figure 2:
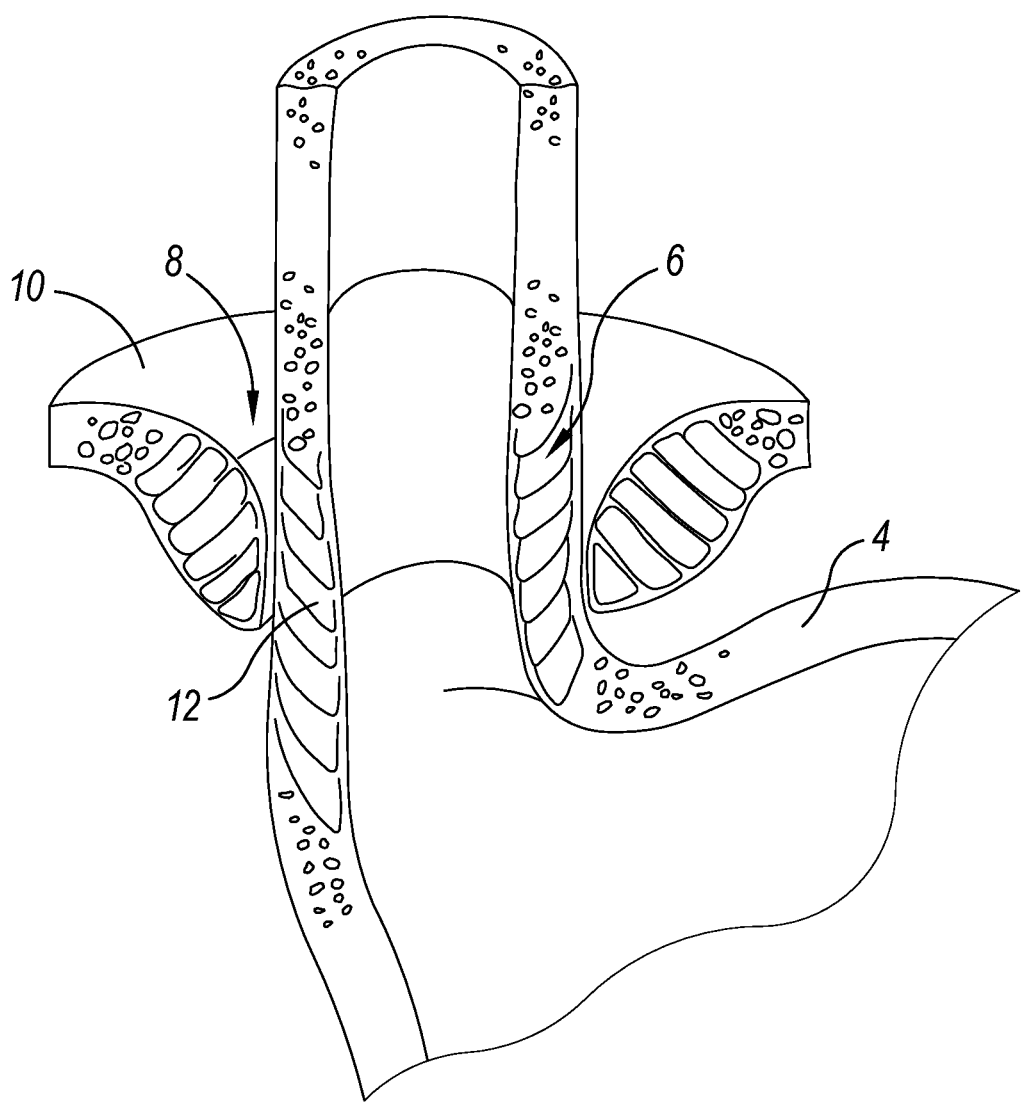
FIG. 2 depicts a cross-sectional isometric view, taken along a coronal plane of the body, of a human esophagogastric junction.
Figure 3:
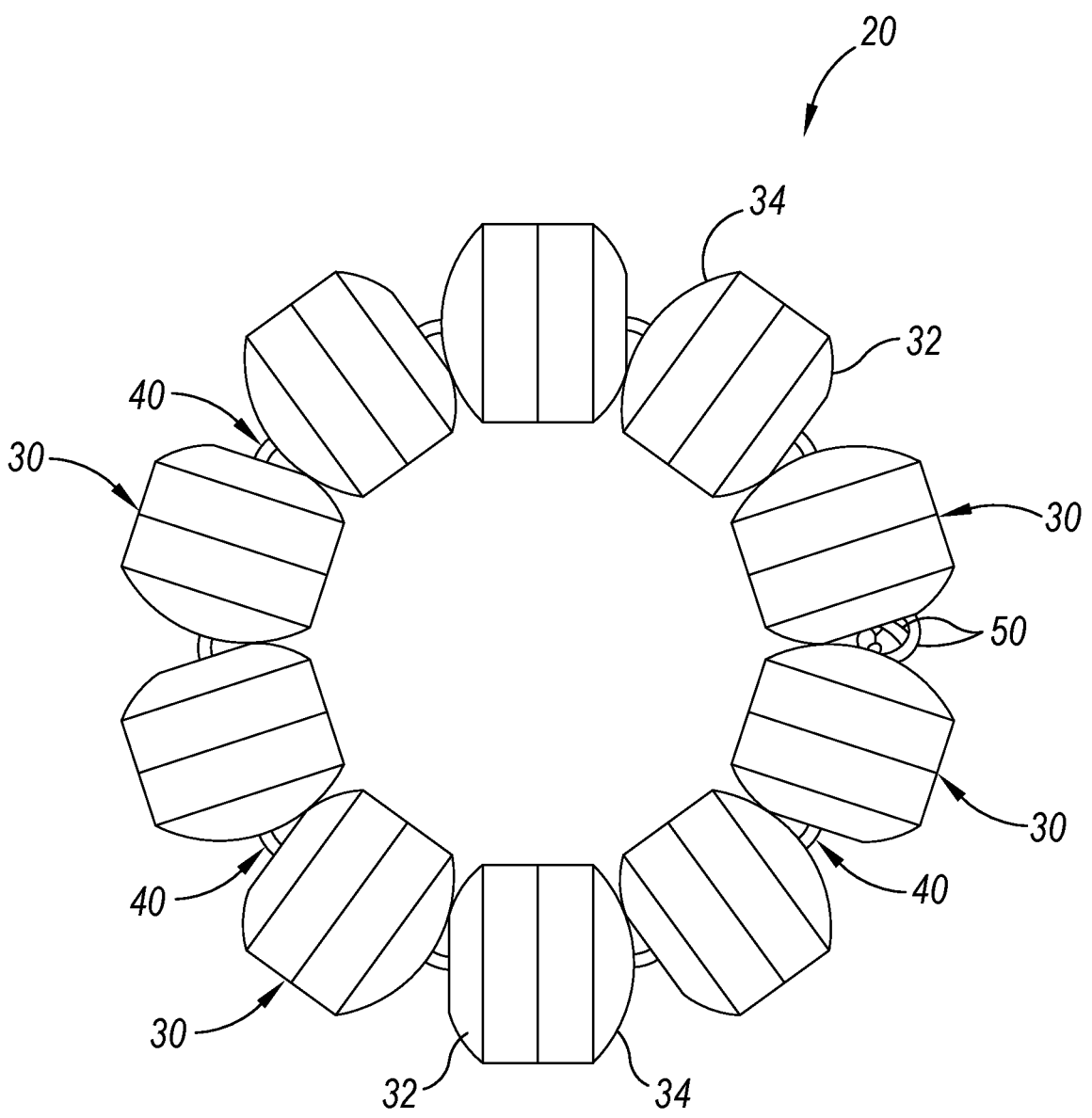
FIG. 3 depicts a top plan view of an example of a sphincter augmentation device.

FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state to act as a valve. In other words, a healthy LES (6) may transition from the occluded state to the opened state to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

If LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or LES (6) may properly transition between the occluded state and the opened state.

Figure 4:
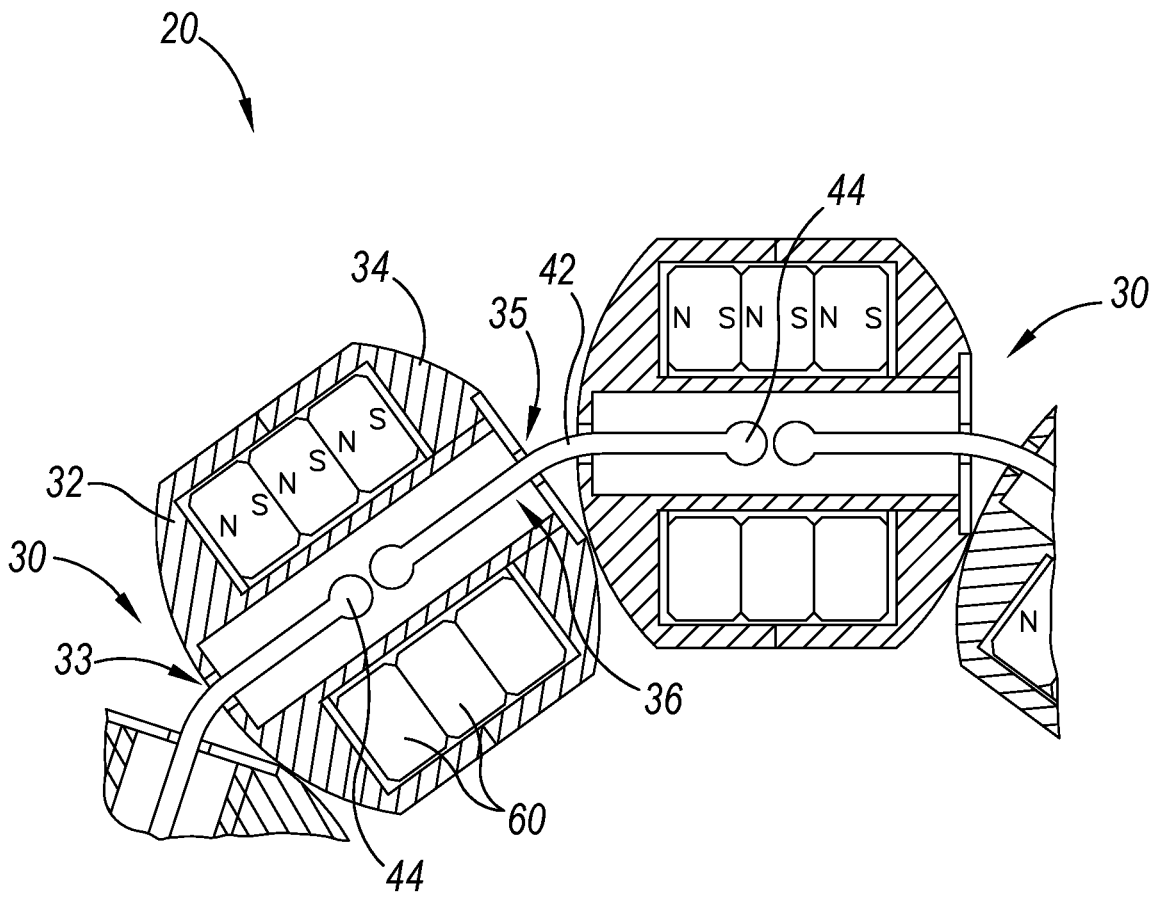
FIG. 4 depicts a partial, cross-sectional view of a portion of the sphincter augmentation device of FIG. 3.

FIGS. 3-5B show an example of a sphincter augmentation device (20) that may be used as an implant around a malfunctioning LES (6) to assist the LES (6) in transitioning between the occluded state and the opened state. Device (20) of this example comprises a plurality of beads (30) that are joined together by a plurality of links (40). Each bead (30) comprises a pair of housings (32, 34) that are securely fastened to each other. By way of example only, housings (32, 34) may be formed of a non-ferrous material (e.g., titanium, plastic, etc.). Each bead (30) further comprises a plurality of annular or toroidal rare-earth permanent magnets (60) that are stacked next to each other within housings (32, 34). In the present example, magnets (60) are completely sealed within beads (30). As best seen in FIG. 4, each bead (30) also defines a chamber (36) that is configured to receive a portion of a respective pair of links (40). Housing (32) defines an opening (33) at one end of chamber (36); while housing (34) defines an opening (35) at the other end of chamber (36).

Each link (40) of the present example comprises a wire (42) that is pre-bent to form an obtuse angle. The free end of each wire (42) terminates in a ball tip (44). Beads (30) are joined together by links (40) such that a first end portion of a link (40) is in one bead (30), a second end portion of the same link (40) is in another bead (30), and an intermediate portion of the same link (40) is positioned between those two beads (30). Chambers (36) of beads (30) are configured to freely receive ball tips (44) and adjacent regions of wires (42); while openings (33, 35) are configured to prevent ball tips (44) from exiting chambers (36). Openings (33, 35) are nevertheless sized to allow wire (42) to slide through openings (33, 35). Thus, links (40) and beads (30) are configured to allow beads (30) to slide along links (40) through a restricted range of motion.

Figure 5A:
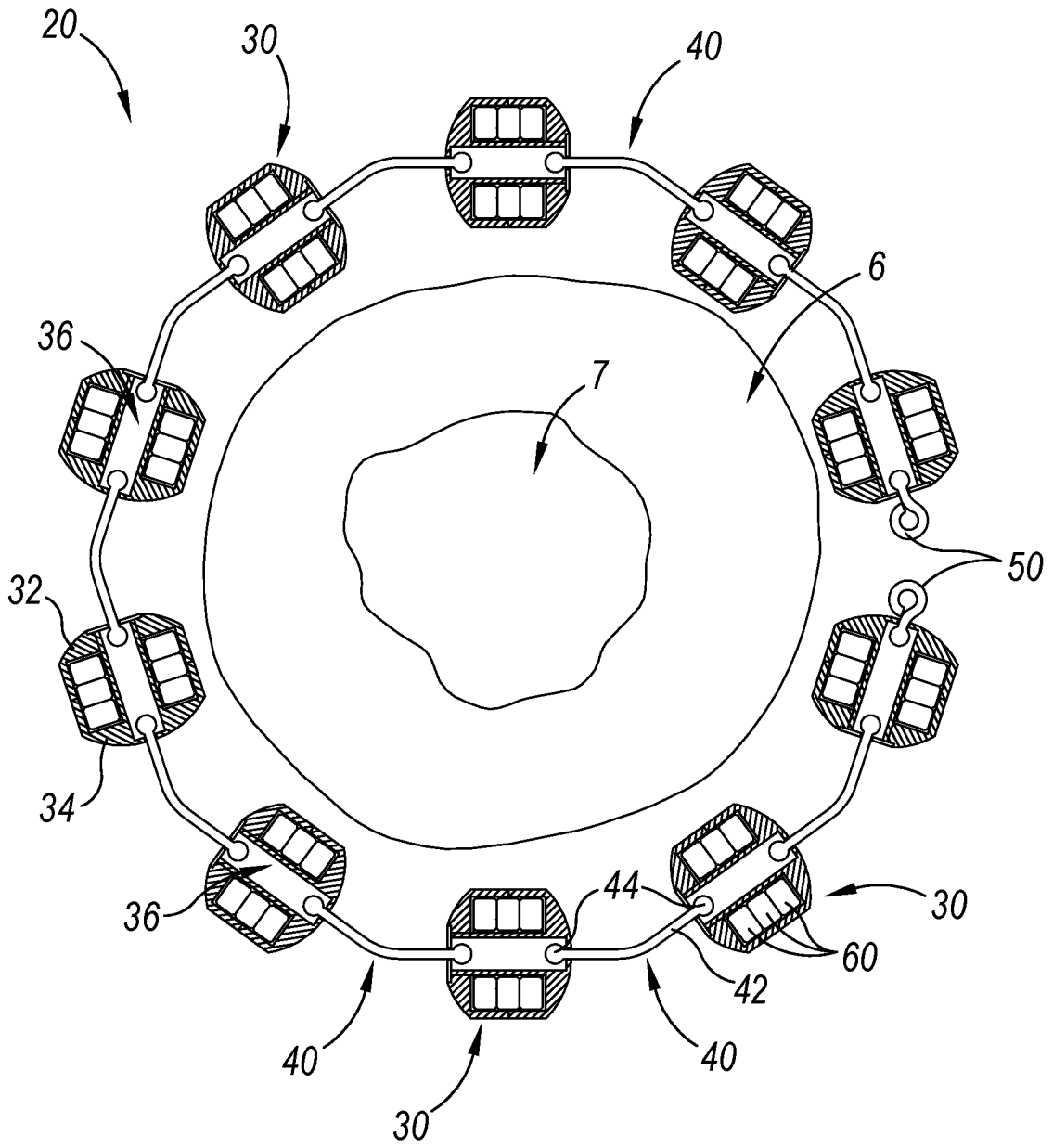
FIG. 5A depicts a top, cross-sectional view of the sphincter augmentation device of FIG. 3 positioned about an LES, with the sphincter augmentation device in an open and expanded configuration.
Figure 5B:
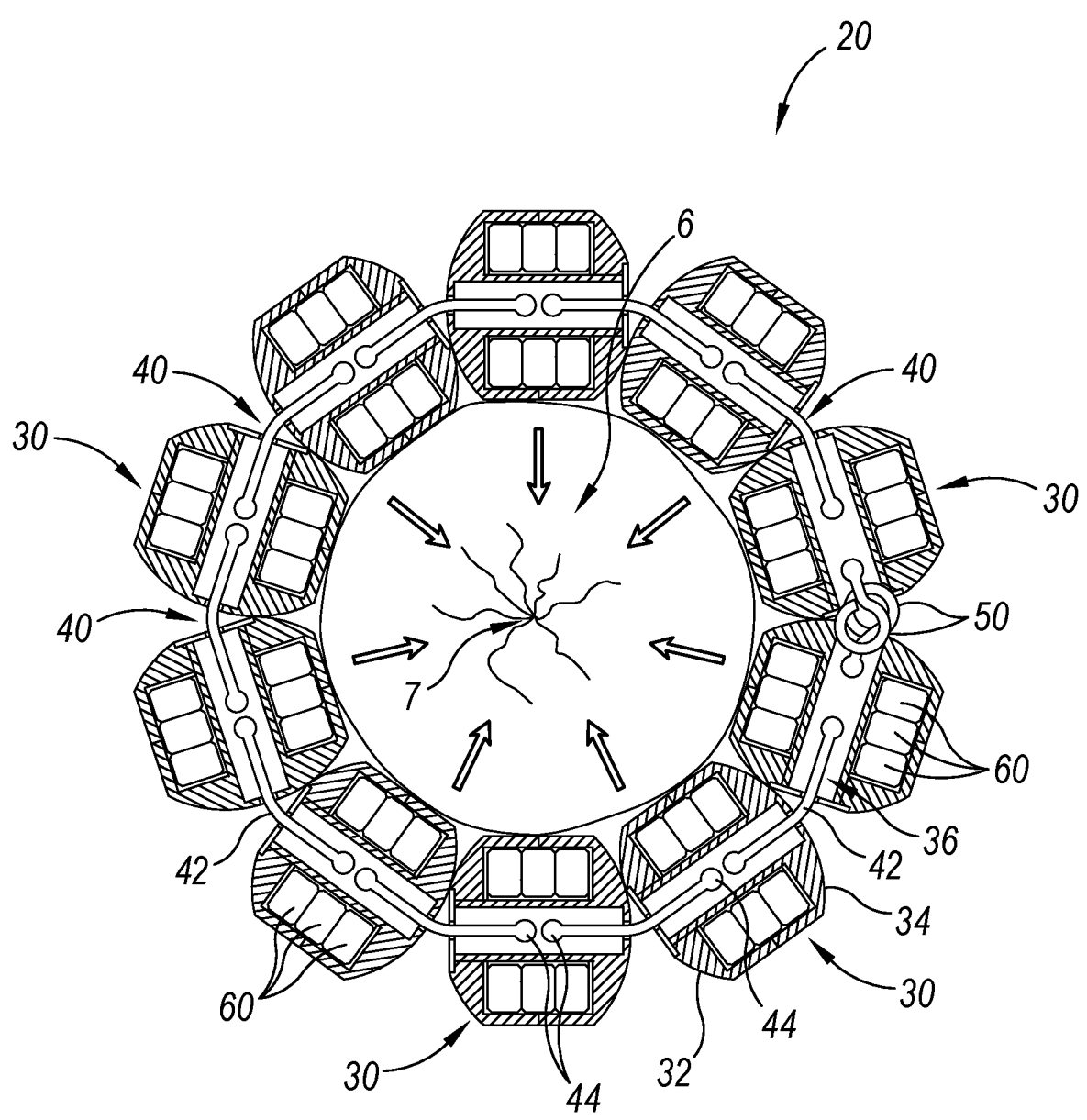
FIG. 5B depicts a top, cross-sectional view of the sphincter augmentation device of FIG. 3 positioned about the LES of FIG. 5A, with the sphincter augmentation device in a closed and contracted configuration.

As best seen in FIGS. 5A-5B, two beads (30) have opposing fastener features (50) that allow the ends of device (20) to be coupled together to form a loop. In the present example, fastener features (50) comprise eyelets. In some other versions, fastener features (50) comprise complementary clasp features. As another merely illustrative example, fastener features (50) may be configured and operable in accordance with one or more of the teachings of U.S. Pat. No. 10,405,865, entitled "Method for Assisting a Sphincter," issued Sep. 10, 2019, the disclosure of which is incorporated by reference herein, in its entirety. Other suitable ways in which the ends of device (20) may be coupled together to form a loop will be apparent to those of ordinary skill in the art in view of the teachings herein. Those of ordinary skill in the art will also recognize that it may be desirable to provide fastener features (50) that can be decoupled if it becomes necessary or otherwise warranted to remove device (20) from the patient.

FIG. 5A shows device (20) in an open, expanded state, with device (20) being positioned about LES (6). At this stage, the opening (7) defined by LES (6) is in a persistently open state (e.g., allowing the patient to undesirably experience GERD and/or other undesirable conditions), warranting the securement of device (20) about the LES (6). FIG. 5B shows device (20) secured about the LES (6), with device (20) in a closed, contracted state. Device (20) is secured closed via fastener features (50). Magnets (60) are oriented within beads (30) such that each bead (30) will be magnetically attracted to the adjacent bead (30) in device (20). In other words, beads (30) are magnetically attracted to each other to magnetically bias device (20) toward the contracted configuration shown in FIG. 5B.

With device (20) secured around the LES (6) and in the contracted configuration, device (20) deforms the LES (6) radially inwardly to substantially close the opening defined by the LES (6). In doing so, device (20) prevents the patient from experiencing GERD and/or other undesirable conditions that may be associated with a persistently open opening (7) at the LES (6). While magnets (60) have a tesla value that is high enough to substantially maintain opening (7) in a closed state to the point of preventing GERD and/or other undesirable conditions that may be associated with a persistently open opening (7), the tesla value of magnets (60) is low enough to allow LES (6) to expand radially outwardly to accommodate passage of a bolus of food, etc. through the opening (7) of LES (6). To accommodate such expansion, beads (30) may simply slide along links (40) to enlarge the effective diameter of device (20) as the bolus passes. After the bolus passes, the magnetic bias of magnets (60) will return device (20) to the contracted state shown in FIG. 5B. Device (20) thus ultimately prevents GERD and/or other undesirable conditions that may be associated with a persistently open opening (7); while still permitting the normal passage of food, etc. from the esophagus (2) to the stomach (4).

In addition to the foregoing, device (20) may be constructed and operable in accordance with at least some of the teachings of U.S. Pat. No. 7,695,427, the disclosure of which is incorporated by reference herein, in its entirety; and/or U.S. Pat. No. 10,405,865, the disclosure of which is incorporated by reference herein, in its entirety.

II. Examples of Implantable Sphincter Assistance Devices with Composite Material Interconnection Elements In some instances, it may be desirable to provide improved control of the expansion and contraction of device (20) via the interconnection elements (e.g., links (40)) between beads (30). For example, it may be desirable to improve the bending resistance, stiffness, and/or buckling strength of the interconnection elements to thereby improve the consistency of the contraction of device (20). In addition, or alternatively, it may be desirable to improve the tensile strength and/or shear strength of the heads (e.g., ball tips (44)) of the interconnection elements to thereby improve the expanded diameter maximum restriction stop strength of the interconnection elements. In some instances, it may also be desirable to improve the fatigue life of device (20) and/or to improve the resistance of device (20) to twisting that might otherwise be caused by re-orientation of magnets (60) when exposed to a strong magnetic field such as those used in magnetic resonance imaging (MRI), via the interconnection elements (e.g., links (40)) between beads (30). Each of the interconnection elements described below may provide one or more these functionalities.

A. Exemplary Interconnection Element with Flared Flat Heads

FIG. 6 shows an exemplary interconnection element in the form of a link (140) for use with sphincter augmentation device (20). Link (140) is similar to link (40) described above except as otherwise described below. In this regard, link (140) of this example may be used to movably (e.g., slidably) join together a pair of beads (not shown), such as beads (30).

Link (140) of the present example comprises a main body in the form of a generally cylindrical wire (142) that is pre-bent to form an obtuse angle. In some versions, wire (142) may be constructed of a composite material, such as a polymer. In addition, or alternatively, wire (142) may have a diameter substantially equal to or less than that of openings (33, 35) of beads (30), for example. The free ends of wire (142) each terminate in a restriction feature in the form of a conical tip, also referred to as a flared flat head (144). In this regard, each flared flat head (144) includes an outwardly-tapered surface (146) extending away from the respective free end of wire (142) and a flat end surface (148), which may have a diameter substantially greater than that of openings (33, 35) of beads (30), for example. In some versions, flared flat heads (144) may each be constructed of a composite material, such as a polymer. In addition, or alternatively, flared flat heads (144) may each have a strength greater than that of wire (142). For example, flared flat heads (144) may each be constructed of a material different material from that of wire (142), or may each be constructed of a different form of a same material as that of wire (142). In any event, a plurality of beads of a sphincter augmentation device, such as beads (30) of sphincter augmentation device (20), may be joined together by respective links (140) such that a first end portion of a link (140) is in one bead (30), a second end portion of the same link (140) is in another bead (30), and an intermediate portion of the same link (140) is positioned between those two beads (30). Chambers (36) of such beads (30) may be configured to freely receive flared flat heads (144) and adjacent regions of wires (142); while openings (33, 35) of such beads (30) may be configured to prevent flared flat heads (144) from exiting chambers (36). Openings (33, 35) may nevertheless be sized to allow wire (142) to slide through openings (33, 35). Thus, links (140) and beads (30) may be configured to allow beads (30) to slide along links (140) through a restricted range of motion.

It will be appreciated that flared flat heads (144) may provide increased resistance to exiting chambers (36) and/or increased shear strength, at least by comparison to ball tips (44), such that link (140) may provide improved structural integrity to sphincter augmentation device (20) when used in place of a respective link (40). In addition, or alternatively, flared flat heads (144) may provide increased rotational capacity of link (140) relative to beads (30) with decreased risk of binding or hanging, at least by comparison to ball tips (44).

B. Exemplary Interconnection Element with Pop Rivet Heads

FIGS. 7A-7B show a portion of another exemplary sphincter augmentation device (220) including a plurality of beads (230) (one shown) and interconnection elements in the form of links (240) (one shown). Beads (230) and links (240) are similar to beads (30) and links (40) described above, respectively, except as otherwise described below. In this regard, bead (230) of this example includes a pair of housings (232) (one shown), a plurality of annular or tor-oidal rare-earth permanent magnets (not shown), such as magnets (60), a chamber (236) that is configured to receive a portion of a respective pair of links (240), and a pair of openings (233) (one shown) at respective ends of chamber (236). Link (240) of this example may be used to movably (e.g., slidably) join together a pair of beads (230).

Link (240) of the present example comprises a main body in the form of a generally cylindrical wire (242), which may be pre-bent to form an obtuse angle. In some versions, wire (242) may be constructed of a composite material, such as a polymer. The free ends (one shown) of wire (242) each terminate in a restriction feature in the form of a bulbous tip (244) defining an annular abutment surface (246), which may have an outer diameter substantially equal to or less than an inner diameter of openings (233) of bead (230), for example. In this regard, link (240) of the present example further comprises a pair of rivets (250) (one shown) each including a deformable shaft (252) configured to be received within a respective opening (233) of bead (230), a pre-formed factory head (254) configured to abut an outer surface of a respective housing (232), and a central bore (256) configured to slidably receive a respective region of wire (242) adjacent to a corresponding bulbous tip (244) such that each annular abutment surface (246) may confront a free end of the shaft (252) of the respective rivet (250). In some versions, rivets (250) may each be constructed of a material different material from that of wire (242). In other versions, rivets (250) may each be constructed of a different form of a same material as that of wire (242).

In any event, each shaft (252) may be deformable from an undeformed state (FIG. 7A) in which the respective rivet (250) and wire (242) are collectively removable from the corresponding bead (230), and a deformed state (FIG. 7B) in which at least a portion of the shaft (252) is deployed into a shop head (258) for sandwiching a wall of the respective housing (232) against the corresponding factory head (254) to thereby secure the respective rivet (250) to the respective housing (232). For example, wire (242) may be pulled in an upward direction (within the frame of reference of FIGS. 7A-7B) to cause abutment surface (246) to compress the free end of shaft (252) against an inner surface of the respective housing (232) to thereby deform shaft (252) in a predeter-mined manner for deploying shop head (258). It will be appreciated that such deformation of shaft (252) may include plastic deformation, such that shop head (258) may remain deployed after shaft (252) has been deformed to deploy shop head (258). Thus, beads (230) of sphincter augmentation device (220) may be joined together by respective links (240) when the shaft (252) of each rivet (250) is deformed to deploy the respective shop head (258) such that a first end portion of a link (240) is in one bead (230), a second end portion of the same link (240) is in another bead (230), and an intermediate portion of the same link (240) is positioned between those two beads (230). Chambers (236) of such beads (230) may be configured to freely receive bulbous tips (244) and adjacent regions of wires (242); while openings (233) of beads (230) may be configured to prevent rivets (250), and thus bulbous tips (244), from exiting chambers (236). Central bore (256) may nevertheless be sized to allow wire (242) to slide through bore (256). Thus, links (240) and beads (230) may be configured to allow beads (230) to slide along links (240) through a restricted range of motion.

In some versions, rivet (250) may be movably secured to the respective housing (232) when the respective shop head (258) is deployed. For example, the distance between the corresponding shop head (258) and factory head (254) may be substantially greater than a thickness of the wall of the respective housing (232). In some such cases, rivet (250) may be fixedly secured to wire (242) near the respective bulbous tip (244) such that wire (242) and rivet (250) may collectively slide within the corresponding opening (233). For example, an epoxy or other suitable adhesive may be applied between wire (242) and rivet (250). In some ver-sions, the application of such epoxy or other suitable adhe-sive may be performed after deployment of shop head (258). In other versions, the application of such epoxy or other suitable adhesive may be performed during deployment of shop head (258). For example, such epoxy or other suitable adhesive may be initially contained within a capsule (not shown) of rivet (250) which may be ruptured during deploy-ment of shop head (258) to automatically apply such epoxy or other suitable adhesive between wire (242) and rivet (250).

Figures 8, 9, 10A, 10B, 10C:
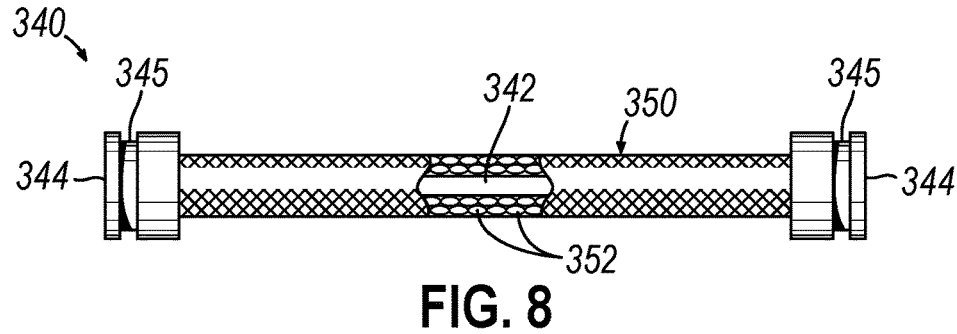
FIG. 8 depicts a side elevation view of another exemplary link for use with the sphincter augmentation device of FIG. 3, showing the link having a titanium wire core and a liquid crystal polymer sheath.
FIG. 9 depicts an exploded perspective view of another exemplary link for use with the sphincter augmentation device of FIG. 3, showing the link having a liquid crystal polymer sheath and crimpable collar heads.
FIG. 10A depicts a side elevation view of the link of FIG. 9, showing crimping of one of the collar heads at one end of the liquid crystal polymer sheath, and further showing advancement of a pair of washers along the liquid crystal polymer sheath.
FIG. 10B depicts a side elevation view of the link of FIG. 9, showing crimping of the other of the collar heads at the other end of the liquid crystal polymer sheath to capture the pair of washers between the crimped collar heads.
FIG. 10C depicts a side elevation view of the link of FIG. 9, showing the washers keyed into respective recesses within the openings of corresponding beads for coupling the beads together.

C. Exemplary Interconnection Element with Titanium Wire Core, Molded Heads, and Liquid Crystal Polymer Sheath FIG. 8 shows another exemplary interconnection element in the form of a link (340) for use with sphincter augmen-tation device (20). Link (340) is similar to link (40) described above except as otherwise described below. In this regard, link (340) of this example may be used to movably (e.g., bendably) join together a pair of beads (not shown), such as beads (30).

Link (340) of the present example comprises an elongate core in the form of a generally cylindrical, annealed titanium wire (342). In other versions, the core of link (340) may be provided in the form of a polymeric cable, such as a high-density polyethylene cable. In any event, the free ends of wire (342) each terminate in a restriction feature in the form of a cylindrical head (344). In this regard, each cylindrical head (344) may be constructed of a polymeric material, such as a liquid crystal polymer (e.g., VECTRA® by Celanese Corporation of Dallas, Texas), and may be molded onto the respective free end of wire (342). In the example shown, each cylindrical head (344) includes an annular groove (345) configured to engage an edge of a respective opening (33, 35) of a corresponding bead (30), for releasably and/or rotatably securing the cylindrical head (344) to the corresponding bead (30). To that end, each cylindrical head (344) may have an outer diameter at least slightly greater than an inner diameter of the respective opening (33, 35), while each annular groove (345) may have an outer diameter substantially equal to or less than the inner diameter of the respective opening (33, 35) to permit the edge of each opening (33, 35) to key into the respective annular groove (345). In some versions, each cylindrical head (344) may be rotatable relative to the corresponding bead (30) while the edge of the opening (33, 35) is keyed into the respective annular groove (345). In addition, or alternatively, each cylindrical head (344) may be released from the corresponding bead (30) by applying a threshold separation force therebetween to unseat the edge of the opening (33, 35) from the respective annular groove (345).

In any event, link (340) of the present example further comprises a generally cylindrical sheath (350) positioned over wire (342) such that sheath (350) and wire (342) may collectively define a main body of link (340). Sheath (350) includes a bundle of interwoven, braided, and/or wound polymeric fibers (352). In some versions, each fiber (352) may be constructed of a liquid crystal polymer. In addition, or alternatively, each fiber (352) may be coated with a polyurethane coating for improving abrasion resistance and/or providing a water barrier, and/or with any other suitable coating material for providing antibacterial protection, for providing a pharmaceutical/biological agent to aid in recovery and/or reduce inflammation, and/or for preventing tissue from adhering to link (340) in a manner that might otherwise impede functionality. Thus, a plurality of beads of a sphincter augmentation device, such as beads (30) of sphincter augmentation device (20), may be joined together by respective links (340) such that a first end portion of a link (340) is secured to one bead (30), a second end portion of the same link (340) is secured to another bead (30), and an intermediate portion of the same link (340) is positioned between those two beads (30). In this manner, links (340) and beads (30) may be configured to allow beads (30) to move relative to each other via outward bending of links (340) through a restricted range of motion. In some versions, links (340) may be pre-bent to promote consistent and reliable outward bending and thereby inhibit links (340) from interfering with the interfaces between beads (30), such as when sphincter augmentation device (20) is in the contracted state. In other versions, beads (30) may be slidable along link (340). In any event, sheath (350) may hold the axial load while wire (342) may provide link (340) with sufficient rigidity to resist bending of link (340) when exposed to a strong magnetic field such as those used in magnetic resonance imaging (MRI), without increasing fatigue sensitivity.

It will be appreciated that sheath (350) may provide improved tensile properties to link (340) and/or improved fatigue resilience to lateral loading, at least by comparison to links (40), such that link (340) may provide improved structural integrity to sphincter augmentation device (20) when used in place of a respective link (40). In addition, or alternatively, sheath (350) may provide increased flexibility further minimizing any risk of binding of wire (342) between beads (30), at least by comparison to link (40).

D. Exemplary Interconnection Element with Liquid Crystal Polymer Sheath and Crimped Collars FIGS. 9-10C show a portion of another exemplary sphincter augmentation device (420) including a plurality of beads (430) and interconnection elements in the form of links (440) (one shown). Beads (430) and links (440) are similar to beads (30) and links (40) described above, respectively, except as otherwise described below. In this regard, beads (430) of this example each include a pair of housings (432, 434), a plurality of annular or toroidal rare-earth permanent magnets (not shown), such as magnets (60), a chamber (436) that is configured to receive a portion of a respective pair of links (440), and a pair of openings (433, 435) at respective ends of chamber (436). Link (440) of this example movably (e.g., slidably and/or bendably) joins together a pair of beads (430).

Link (440) of the present example comprises a pair of restriction features in the form of first and second head assemblies (444a, 444b) secured to respective ends of a main body in the form of a generally cylindrical sheath (450) including a bundle of interwoven, braided, and/or wound polymeric fibers (452). In some versions, each fiber (452) may be constructed of a liquid crystal polymer. In addition, or alternatively, each fiber (452) may be coated with a polyurethane coating for improving abrasion resistance and/or providing a water barrier, and/or with any other suitable coating material for providing antibacterial protection, for providing a pharmaceutical/biological agent to aid in recovery and/or reduce inflammation, and/or for preventing tissue from adhering to link (440) in a manner that might otherwise impede functionality. In any event, first and second head assemblies (444a, 444b) include first and second inner collars (454a, 454b), respectively, and first and second outer collars (456a, 456b), respectively, configured to cooperate with each other to retain a corresponding end of sheath (450). Link (440) of the present example further comprises first and second washers (458a, 458b) configured to slidably couple sheath (450) to respective beads (30).

In this regard, first inner collar (454a) may initially be received within a first end of sheath (450) and first outer collar (456a) may then be positioned over the first end of sheath (450) and crimped to thereby pinch the first end of sheath (450) between first inner and outer collars (454a, 456a) and form first head assembly (444a), and first and second washers (458a, 458b) may be slid from a second end of sheath (450) toward the first end of sheath (450), as shown in FIG. 10A. Second inner collar (454b) may subsequently be received within a second end of sheath (450) and second outer collar (456b) then be positioned over the second end of sheath (450) and crimped to thereby pinch the second end of sheath (450) between second inner and outer collars (454b, 456b) and form second head assembly (444b), with first and second washers (458a, 458b) slidably captured between first and second head assemblies (444a, 444b), as shown in FIG. 10B. First and second washers (458a, 458b) may then be keyed into respective annular recesses (459) of openings (433, 435). Thus, beads (430) of sphincter augmentation device (420) may be joined together by respective links (440) such that a first end portion of a link (440) is in one bead (430), a second end portion of the same link (440) is in another bead (430), and an intermediate portion of the same link (440) is positioned between those two beads (430). In the example shown, each outer collar (456a, 456b) has an outer diameter greater than the inner diameter of each washer (458a, 458b), such that engagement between outer collars (456a, 456b) and washers (458a, 458b) may restrict longitudinal motion of each link (440) relative to the respective beads (430), thereby preventing links (440) from being pulled out of the respective beads (430). In this manner, links (440) and beads (430) may be configured to allow beads (430) to slide along links (440) and/or to move relative to each other via outward bending of links (440) through a restricted range of motion.

In some versions, link (440) may further comprise an elongate core (not shown) in the form of an annealed titanium wire or a polymeric cable, such as a high-density polyethylene cable, in a manner similar to that described above in connection with FIG. 8.

III Examples of Implantable Sphincter Assistance Devices with Dual Zone Controlled Rate of Constriction Force In some instances, it may be desirable to adjust the constriction force and/or a rate of change of the constriction force that is applied by device (20) based on a dilation ratio of device (20) (e.g., a ratio of the diameter of the loop formed by device (20) in a current state of expansion relative to the maximum diameter of the loop formed by device (20) in the fully expanded state). FIGS. 11A-13 show a portion of another exemplary sphincter augmentation device (520) that may provide such functionality and that includes a plurality of beads (530) and interconnection elements in the form of links (540). Beads (530) and links (540) are similar to beads (30) and links (40) described above, respectively, except as otherwise described below. In this regard, beads (530) of this example each include a pair of housings (532, 534), at least one annular or toroidal rare-earth permanent magnet (560), a chamber (536) that is configured to receive a portion of a respective pair of links (540), and a pair of openings (533, 535) at respective ends of chamber (536). Links (540) of this example each movably (e.g., slidably) join together a respective pair of beads (530).

In the example shown, each chamber (536) includes an inner cylindrical portion (537), a pair of outer conical portions (538) terminating at respective openings (533, 535), and a pair of intermediate enlarged portions (539) extending between inner cylindrical portion (537) and respective outer conical portions (538). A resilient member in the form of a toroidal slanted coil spring (541) is positioned within each intermediate enlarged portion (539), the purpose of which is described below.

Links (540) of the present example each comprise a main body in the form of a generally cylindrical wire (542) with free ends which each terminate in a restriction feature in the form of a conical head (544). In this regard, each conical head (544) includes an outwardly-tapered cam surface (546) extending away from the respective free end of wire (542) and a flat end surface (548), which may have a diameter substantially greater than that of openings (533, 535) of beads (530), for example. In some versions, wire (542) and/or conical heads (544) may be constructed of a composite material, such as one or more polymers. For example, each link (540) may be at least partially constructed of a flexible plastic material or elastomer. In this regard, each link (540) may be synthetic and may allow for bending relative to beads (530) to improve motion between beads (530) while limiting maximum extension of beads (530) away from each other. In addition, or alternatively, each link (540) may include a woven plastic belt or band to inhibit fraying and fatigue while providing flexibility and longitudinal strength. In any event, beads (530) of sphincter augmentation device (520) are joined together by respective links (540) such that a first end portion of a link (540) is in one bead (530), a second end portion of the same link (540) is in another bead (530), and an intermediate portion of the same link (540) is positioned between those two beads (530). Chambers (536) of such beads (530) may be configured to freely receive conical heads (544) and adjacent regions of wires (542); while openings (533, 535) of such beads (530) may be configured to prevent conical heads (544) from exiting chambers (536). Openings (533, 535) may nevertheless be sized to allow wire (542) to slide through openings (533, 535). Thus, links (540) and beads (530) may be configured to allow beads (530) to slide along links (540) through a restricted range of motion.

Figure 11A:
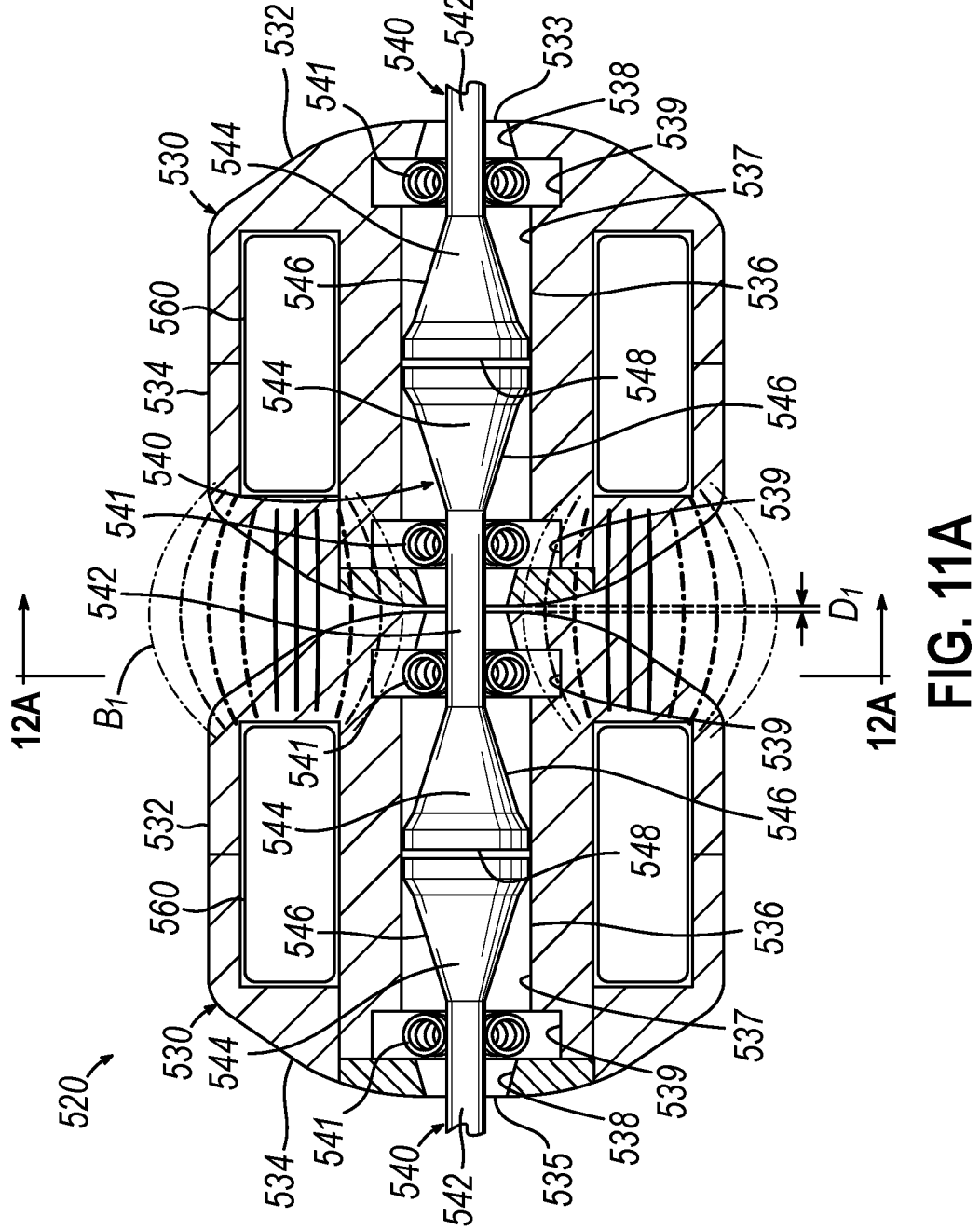
FIG. 11A depicts a top, cross-sectional view of a portion of another exemplary sphincter augmentation device having a pair of beads coupled together by a link, showing toroidal coil springs of each bead positioned about a wire of the link to apply a minimal constrictive force to the link when a dilation ratio of the device is between approximately 0% and approximately 25%.

In the example shown, each coil spring (541) is resiliently biased toward a radially contracted state in which coil spring (541) has an inner diameter substantially equal to or slightly greater than an outer diameter of wire (542), as shown in FIG. 11A. In this state, each wire (542) may provide negligible or no resistance to the respective coil spring (541). Each coil spring (541) may be radially expanded by the respective cam surface (546) to adjust the amount of resistance applied to the respective coil spring (541) and likewise adjust a constrictive force applied by the respective coil spring (541) to the corresponding link (540), as described in greater detail below.

Figures 12A, 12B, 12C:
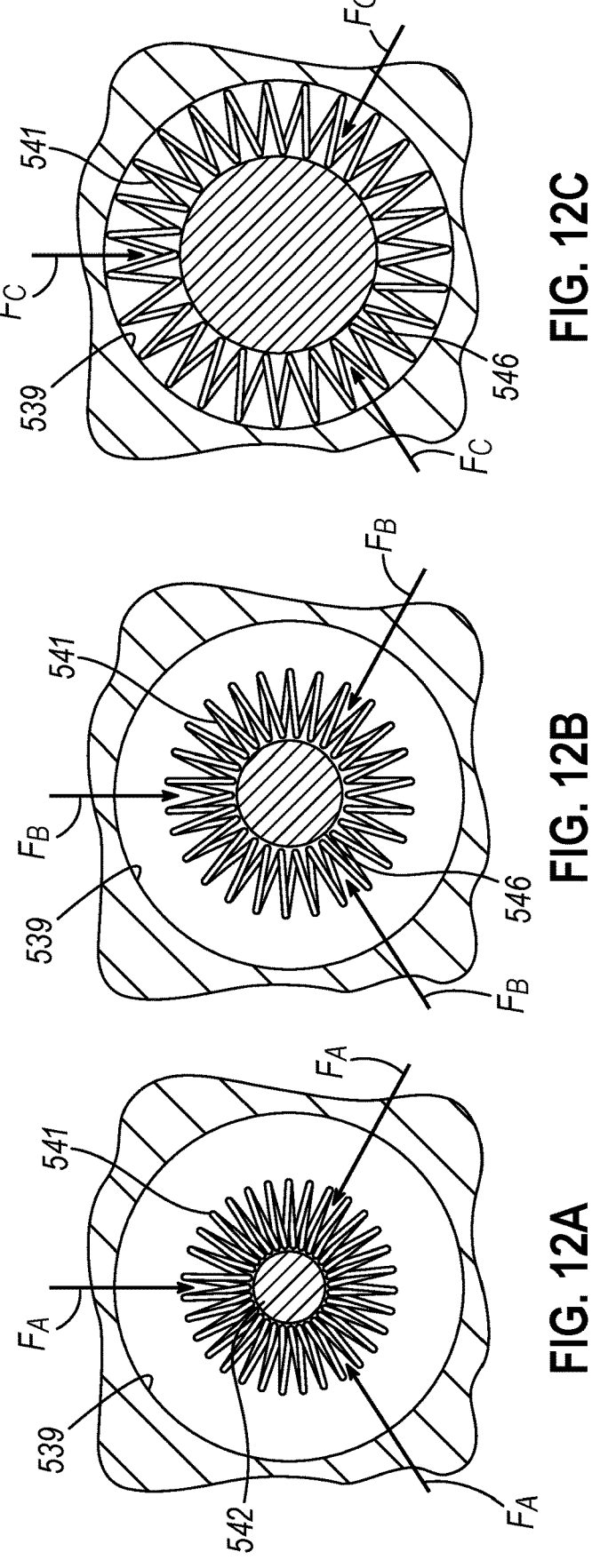
FIG. 12A depicts a cross-sectional view of a portion of the sphincter augmentation device of FIG. 11A, taken along section line 12A-12A in FIG. 11A.
FIG. 12B depicts a cross-sectional view of a portion of the sphincter augmentation device of FIG. 11A, taken along section line 12B-12B in FIG. 11B.
FIG. 12C depicts a cross-sectional view of a portion of the sphincter augmentation device of FIG. 11A, taken along section line 12C-12C in FIG. 11C.

As shown in FIG. 11A, device (520) may initially have a dilation ratio of between approximately 0% and approximately 25%, at which beads (530) may be spaced apart from each other by a first distance ($D_1$) of between approximately 0% and approximately 25% of the maximum distance between beads (530) (e.g., which may occur when device (520) is fully expanded). Due to this relative positioning of beads (530), magnets (560) may be spaced apart from each other to generate a first magnetic field ($B_1$) which applies a first magnetic force ($F_1$) between magnets (560) having a maximal magnitude, such as between approximately 32 gf and approximately 57 gf. Also due to this relative positioning of beads (530), coil springs (541) may each be positioned over the wire (542) of the respective link (540) and may thereby remain in the contracted state with wire (542) providing negligible or no resistance to coil spring (541) such that each coil spring (541) may apply a first constrictive force ($F_A$) having a minimal magnitude to link (540), as shown in FIG. 12A.

Figure 11B:
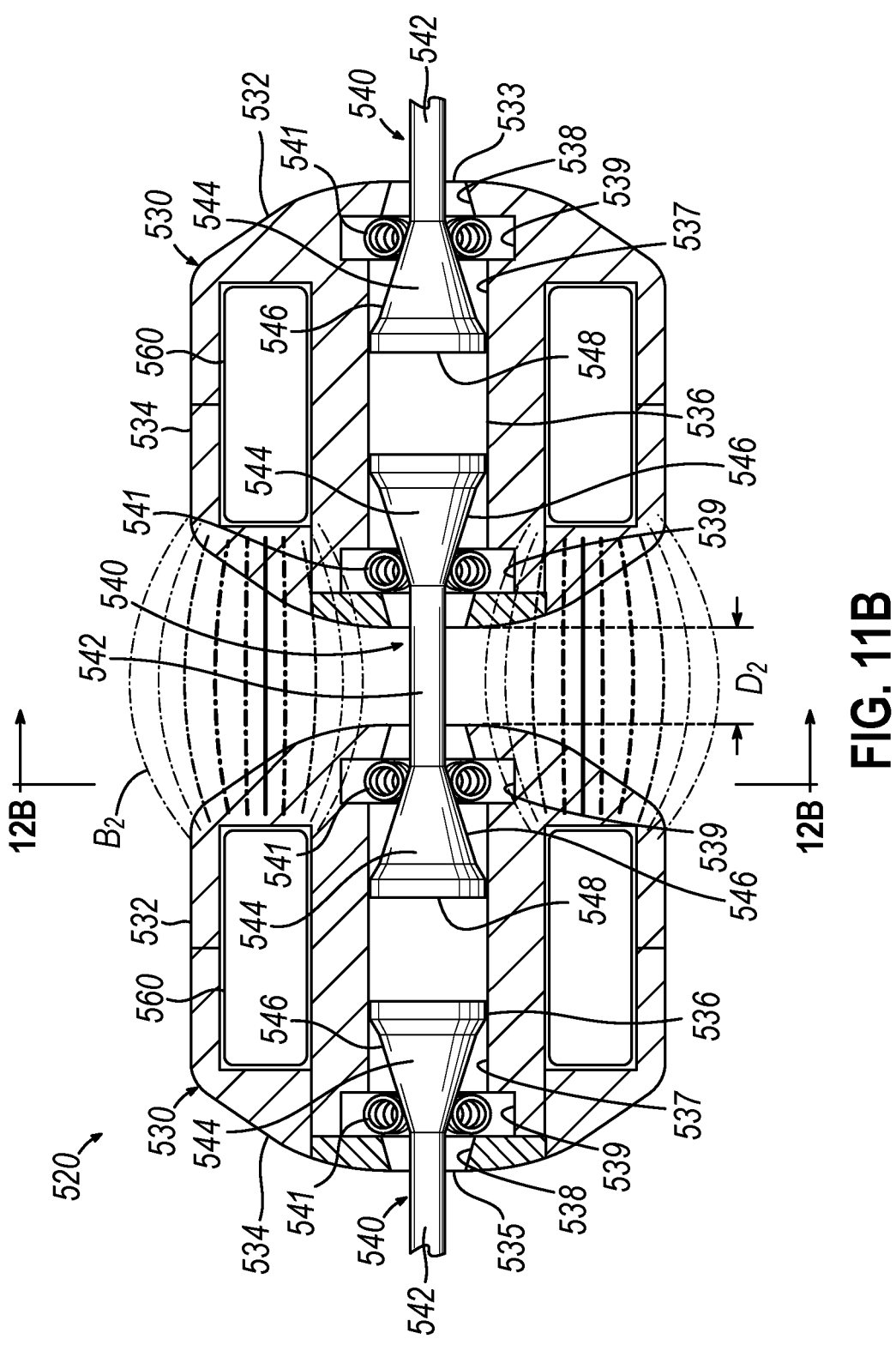
FIG. 11B depicts a top, cross-sectional view of a portion of the sphincter augmentation device of FIG. 11A, showing the toroidal coil springs of each bead positioned about a narrow portion of a tapered cam surface of the link to apply an intermediate constrictive force to the link when the dilation ratio of the device is between approximately 25% and approximately 75%.

As shown in FIG. 11B, device (520) may subsequently expand to have a dilation ratio of between approximately 25% and approximately 75%, at which beads (530) may be spaced apart from each other by a second distance ($D_2$) of between approximately 25% and approximately 75% of the maximum distance between beads (530). Due to this relative positioning of beads (530), magnets (560) may be spaced apart from each other to generate a second magnetic field ($B_2$) which applies a second magnetic force ($F_2$) between magnets (560) having an intermediate magnitude (e.g., slightly less than the first magnetic force ($F_1$)). Also due to this relative positioning of beads (530), coil springs (541) may each be positioned over a relatively narrow portion of cam surface (546) of the respective link (540) and may thereby be urged radially outwardly by cam surface (546) to a first expanded state such that each coil spring (541) may apply a second constrictive force ($F_B$) having an intermediate magnitude (e.g., slightly greater than first constrictive force ($F_A$)) to link (540), as shown in FIG. 12B.

Figure 11C:
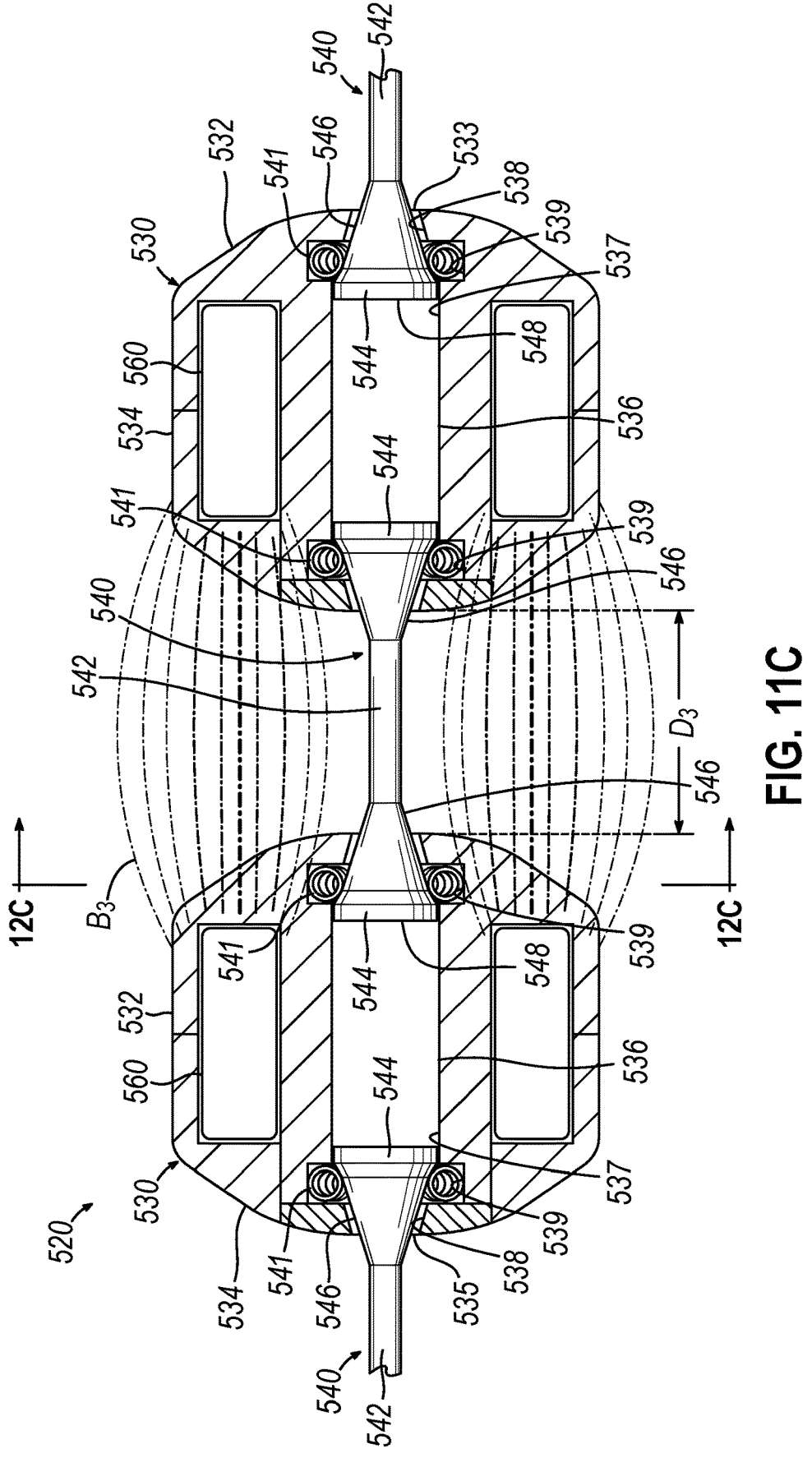
FIG. 11C depicts a top, cross-sectional view of a portion of the sphincter augmentation device of FIG. 11A, showing the toroidal coil springs of each bead positioned about a wide portion of a tapered cam surface of the link to apply a maximal constrictive force to the link when the dilation ratio of the device is between approximately 75% and approximately 100%.

As shown in FIG. 11C, device (520) may subsequently further expand to have a dilation ratio of between approximately 75% and approximately 100%, at which beads (530) may be spaced apart from each other by a third distance ($D_3$) of between approximately 75% and approximately 100% of the maximum distance between beads (530). Due to this relative positioning of beads (530), magnets (560) may be spaced apart from each other to generate a third magnetic field ($B_3$) which applies a third magnetic force ($F_3$) between magnets (560) having a minimal magnitude (e.g., substantially less than the second magnetic force ($F_2$)). Also due to this relative positioning of beads (530), coil springs (541) may each be positioned over a relatively wide portion of cam surface (546) of the respective link (540) and may thereby be urged further radially outwardly by cam surface (546) to a second expanded state such that each coil spring (541) may apply a third constrictive force (Fc) having a maximal magnitude (e.g., substantially greater than second constrictive force ($F_B$)) to link (540), as shown in FIG. 12C. In the example shown, each coil spring (541) engages an annular backstop surface of the corresponding intermediate enlarged portion (539) of the respective chamber (536) when in the second expanded state to prevent further radial expansion of the coil spring (541).

Thus, expansion of device (520) and separation of beads (530) (and, conversely, contraction of device (520) and approximation of beads (530)) may occur in two distinct phases to provide improved control of the constrictive forces applied by device (520). In the first phase, magnets (560) are the primary source of the constrictive forces applied by device (20). In the second phase, coil springs (541) are the primary source of the constrictive forces applied by device (20). Following the initial separation of magnets (560) (e.g., via the application of a threshold separation force between approximately 32 gf and approximately 57 gf), the constrictive load of beads (530) may be reduced, at which time coil springs (541) may engage cam surfaces (546) and increase the constrictive load of beads (530) to a point greater than the original maximal load of magnets (560) (e.g., greater than approximately 57 gf). Such a dual-phase approach may promote separation of all magnets (560) of device (520) prior to sufficient engagement of coil springs (541) to increase the constrictive load of beads (530) above the original maximal load of magnets (560). In some versions, the biphasic expansion and contraction of device (520) may be provided entirely (or at least primarily) via magnets (560) for the first phase; and entirely (or at least primarily) via elasticity of interconnection elements (540) themselves for the second phase, such that coil springs (541) may be omitted.

Figure 13:
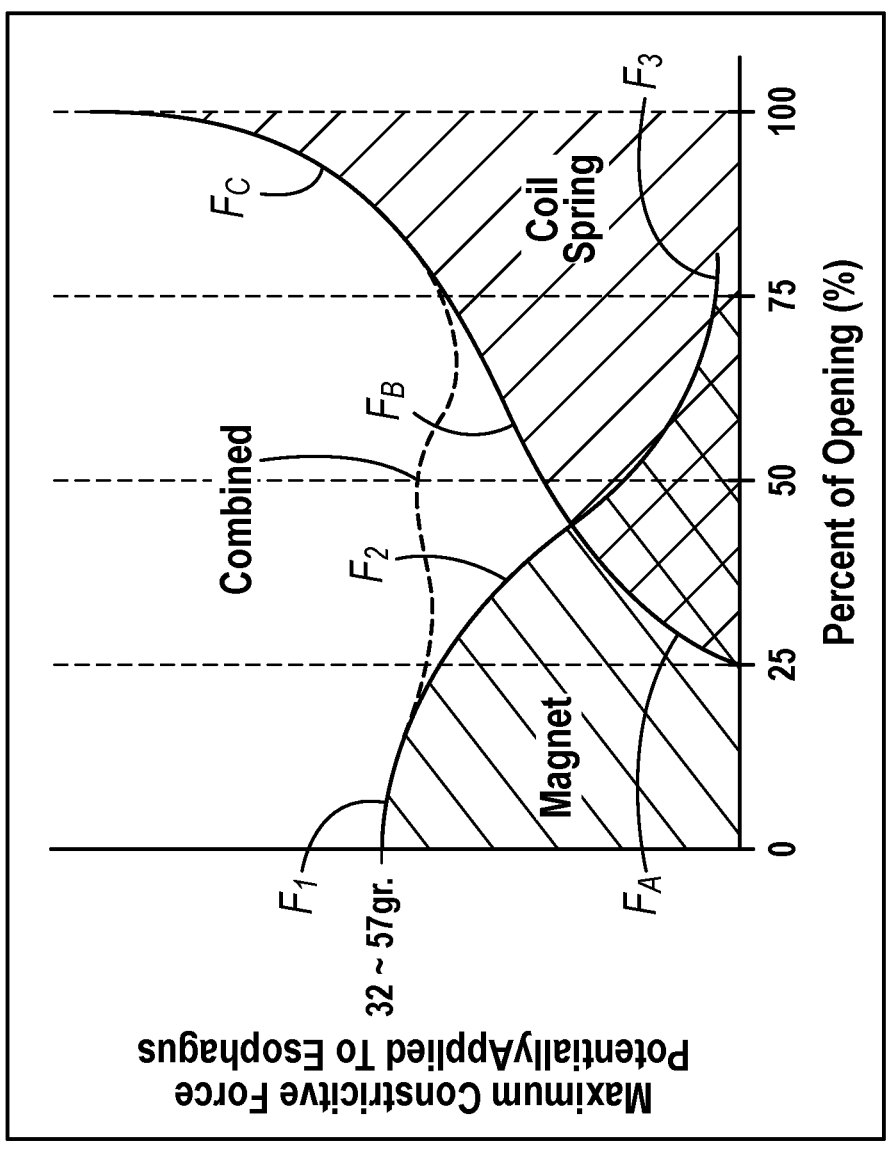
FIG. 13 depicts a graph of the maximum constrictive force applied by the sphincter augmentation device of FIG. 11A plotted against the dilation ratio of the device.

In this regard, FIG. 13 shows an example of the maximum constrictive force potentially applied by device (520) to a lumen, such as esophagus (2), plotted against the dilation ratio (also referred to as a percentage of opening) of device (520). As shown, the constrictive force applied by device (520) has at least three different rates of change based on the dilation ratio. More particularly, the constrictive force has a first rate of change while the dilation ratio is between approximately 0% and approximately 25% based primarily on magnets (560), at least one second rate of change while the dilation ratio is between approximately 25% and approximately 75% based on both magnets (560) and coil springs (541), and a third rate of change while the dilation ratio is between approximately 75% and approximately 100% based primarily on coil springs (541).

As shown in FIG. 13, the constrictive forces provided by magnets (560) while device (520) is fully contracted (e.g., while the dilation ratio is between approximately 0% and approximately 25%) and while device (520) is partially contracted (e.g., while the dilation ratio is between approximately 25% and approximately 75%) are each substantially greater than the constrictive force provided by magnets (560) while device (520) is fully expanded (e.g., while the dilation ratio is between approximately 75% and approximately 100%). In this regard, the constrictive force provided by magnets (560) while device (520) is fully contracted is greater than the constrictive force provided by magnets (560) while device (520) is partially contracted, although the rate of change of the constrictive force provided by magnets (560) while device (520) is partially contracted is substantially greater than the rate of change of the constrictive force provided by magnets (560) while device (520) is fully contracted.

IV. Examples of Implantable Sphincter Assistance Devices with Bimodal Circumferential Restriction Force Threshold In some instances, it may be desirable to provide improved control of the constriction force applied by device (20) and/or to change the sizes of the minimum and maximum inner diameters of device (20) at the fully contracted and fully expanded states, respectively, such as for promoting homogeneity of the force applied by device (20) during expansion and contraction of device (20) and/or while device (20) is in the fully expanded and fully contracted states. As used herein, "homogeneity" refers to the application of a substantially uniform force to tissue via device (20) at equal intervals along the circumference of device (20), such as by applying substantially equal forces to tissue at each bead (30). It will be appreciated that such homogeneity may be desirable during expansion and contraction of device (20) and/or while device (20) is in either the fully expanded or fully contracted state, in order to avoid applying forces that are inconsistent with each other (e.g., in direction and/or in magnitude) about the circumference of the tissue, which might otherwise interfere with proper dilation and closure of the LES (6) or other biological passage at which device (20) is installed. For example, a plurality of expandable and contractable zones may be defined at substantially equal intervals about the circumference of device (20), such as between respective pairs of circumferentially-adjacent beads (30). Homogenous expansion or contraction may be achieved when all of the zones expand or contract at a uniform rate (e.g., at a substantially same rate as each other). A homogeneous fully expanded or contracted state may be achieved when all of the zones are equally sized (e.g., such that the respective pairs of circumferentially-adjacent beads (30) are equally spaced apart).

While a device (20) having uniformly configured and equally spaced apart beads (30) may theoretically provide such homogeneity, minor manufacturing defects or other imperfections of device (20) and/or unique anatomical features of the particular LES (6) or other biological passage at which device (20) is installed may impair the ability of device (20) to actually provide such homogeneity. Thus, it may be desirable to compensate for these types of variations. In addition, or alternatively, device (20) may have a minimum inner diameter at the fully contracted state that is too large relative to the LES (6) or other biological passage at which device (20) is installed such that each bead (30) may not properly engage the tissue, thereby impairing the ability of device (20) to provide homogeneous force application in the fully contracted state. Thus, it may be desirable to decrease the minimum inner diameter of device (20) at the fully contracted state. Each of the devices described below may provide one or more these functionalities.

Figure 14:
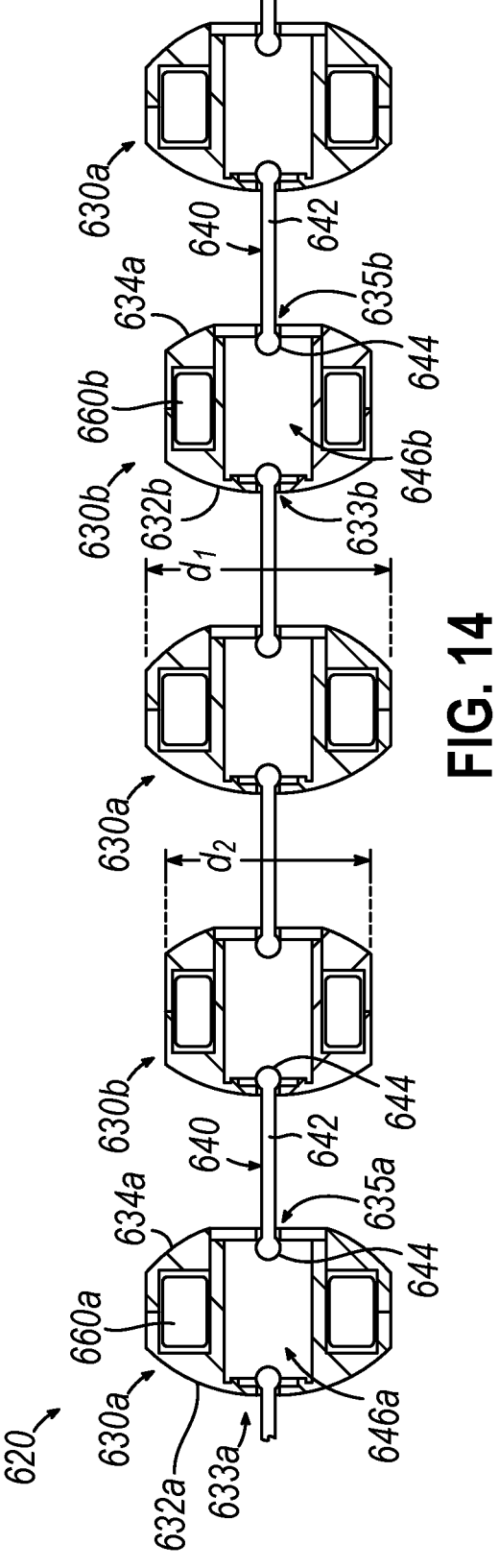
FIG. 14 depicts a top, cross-sectional view of a portion of another exemplary sphincter augmentation device, showing beads of the device having circumferentially-alternating diameters for accommodating differently-sized magnets.

A. Exemplary Device with Beads Having Circumferentially-Alternating Diameters FIGS. 14-15B show another exemplary sphincter augmentation device (620) including a plurality of beads (630a, 630b) and interconnection elements in the form of links (640). Beads (630a, 630b) and links (640) are similar to beads (30) and links (40) described above, respectively, except as otherwise described below. In this regard, beads (630a, 630b) of this example each include a first housing (632a, 632b), a second housing (634a, 634b), at least one annular or toroidal rare-earth permanent magnet (660a, 660b), a chamber (646a, 646b) that is configured to receive a portion of a respective pair of links (640), a first opening (633a, 633b) at a first end of chamber (646a, 646b), and a second opening (635a, 635b) at a second end of chamber (646a, 646b). Links (640) of this example each include a main body in the form of a generally cylindrical wire (642) with free ends which each terminate in a restriction feature in the form of a ball tip (644) and movably (e.g., slidably) join together a respective pair of beads (630a, 630b).

Figure 15A:
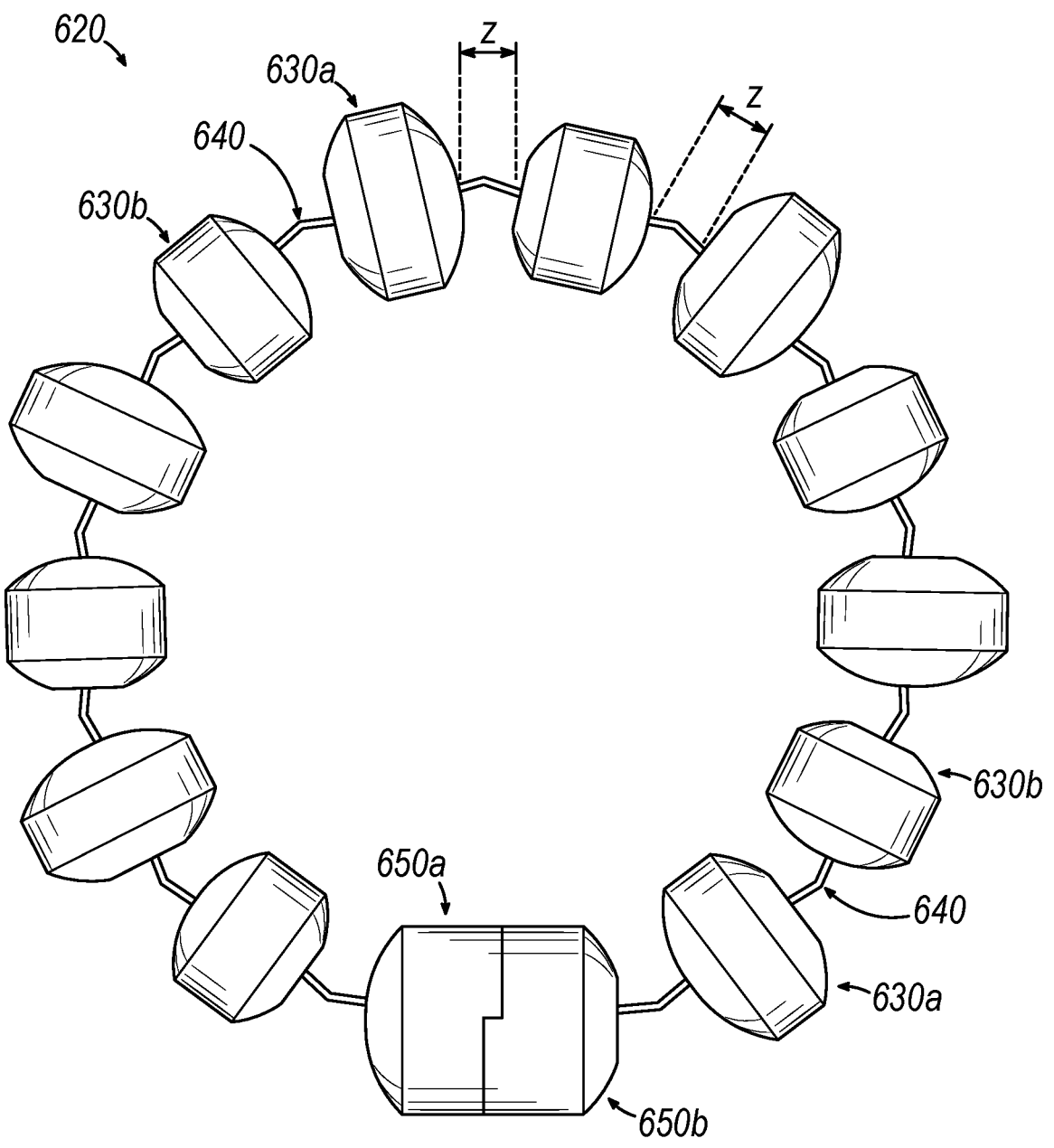
FIG. 15A depicts a top plan view of the sphincter augmentation device of FIG. 14, showing the device in a fully expanded state.
Figure 15B:
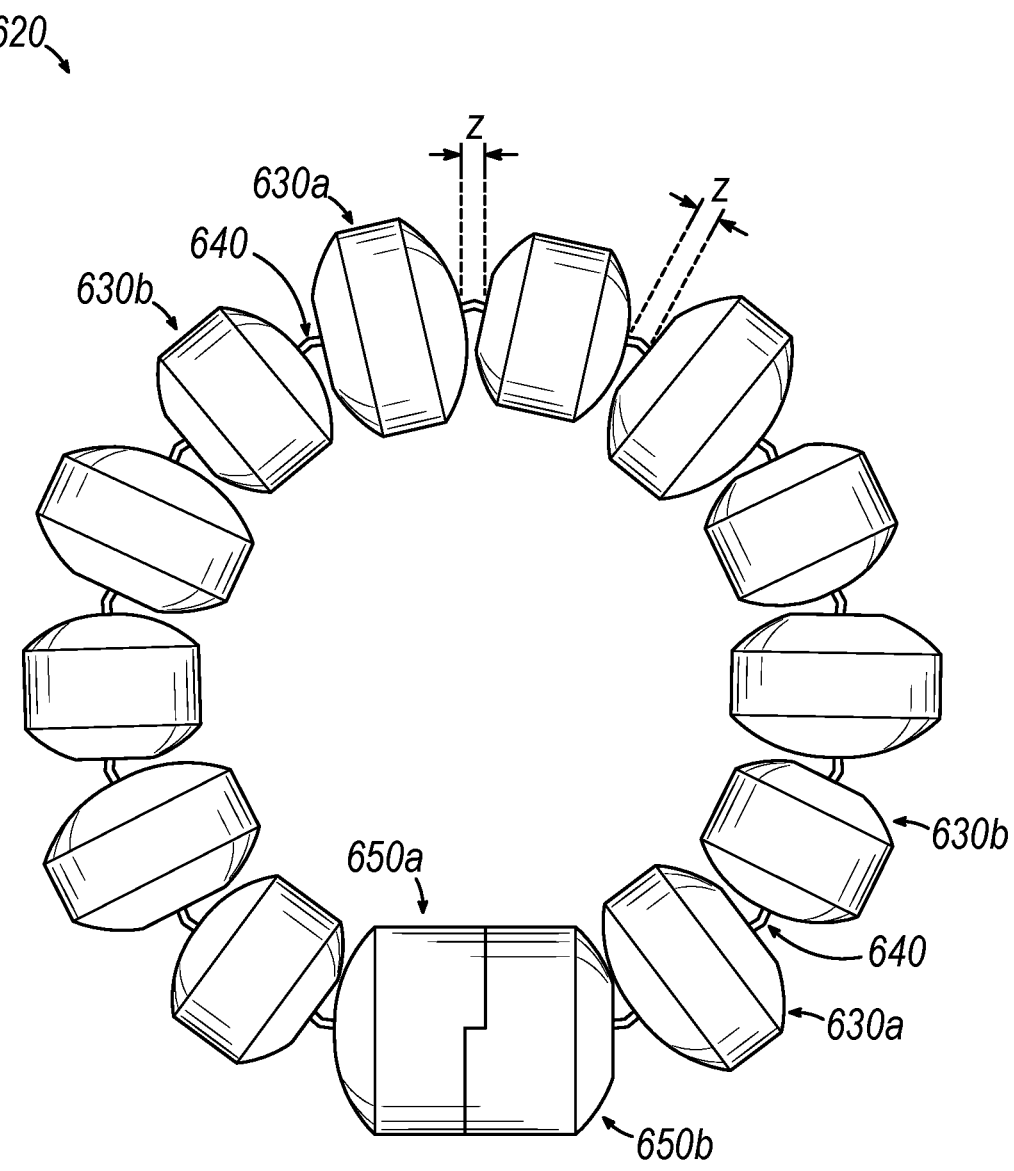
FIG. 15B depicts a top plan view of the sphincter augmentation device of FIG. 14, showing the device in a fully contracted state.

Sphincter augmentation device (620) of the present version also includes opposing fastener features in the form of complementary clasp structures (650a, 650b) coupled to respective beads (630) via corresponding links (640) to allow the ends of device (620) to be coupled together to form a loop, as shown in FIGS. 15A-15B. Clasp structures (650a, 650b) may be constructed and operable in accordance with at least some of the teachings of U.S. Pat. No. 11,071,619, entitled "Coupling Assembly for Implantable Sphincter Assistance Device," issued Jul. 27, 2021, U.S. Pat. No. 10,716,570, entitled "Magnetic Restraint Mechanism for a Sphincter Assist Device," issued Jul. 21, 2020, and/or U.S. Pub. No. 2011/0098731, entitled "Magnetically Assisted Clasps for Prosthetic Implants, and Related Methods," published Apr. 28, 2011, now abandoned, the disclosures of which are incorporated by reference herein, in their entirety.

In the example shown, the plurality of beads (630a, 630b) includes a plurality of first beads (630a) each having a first diameter ($d_1$) (e.g., at a centerline thereof) and a plurality of second beads (630b) each having a second diameter ($d_2$) (e.g., at a centerline thereof) less than the first diameter ($d_1$). As shown, first and second beads (630a, 630b) are arranged in an alternating manner, such that each first bead (630a) is positioned between a pair of second beads (630b) and each second bead (630b) is positioned between a pair of first beads (630a). For example, when the ends of device (620) are coupled together to form a loop, first and second beads (630a, 630b) may alternate with each other circumferentially with respect to the loop (i.e., around the circumference), as shown in FIGS. 15A-15B.

By circumferentially alternating between first and second diameters ($d_1$, $d_2$), beads (630a, 630b) may allow the sizes of magnets (660a, 660b) to circumferentially alternate, thereby permitting different magnetic fields to be generated between adjacent magnets (660a, 660b) than those generated between adjacent, uniformly-sized magnets, such as magnets (60) of device (20). The different sizes of magnets (660a, 660b) may be selected based on the anatomy of a particular patient to provide predetermined magnetic fields for achieving a desired constriction force for that patient. In any event, a plurality of expandable and contractable zones (Z) are defined at substantially equal intervals about the circumference of device (620), and, more particularly, between respective pairs of circumferentially-adjacent beads (630a, 630b). As shown, zones (Z) may expand and contract at a uniform rate and also may be equally sized when device (620) is in either the fully expanded state (FIG. 15A) or the fully contracted state (FIG. 15B), due to the circumferentially-alternating arrangement of magnets (660a, 660b), and may thereby promote homogeneity of the force applied to the tissue by device (620).

B. Exemplary Device with Beads Having Circumferentially-Alternating Lengths

Figure 16:
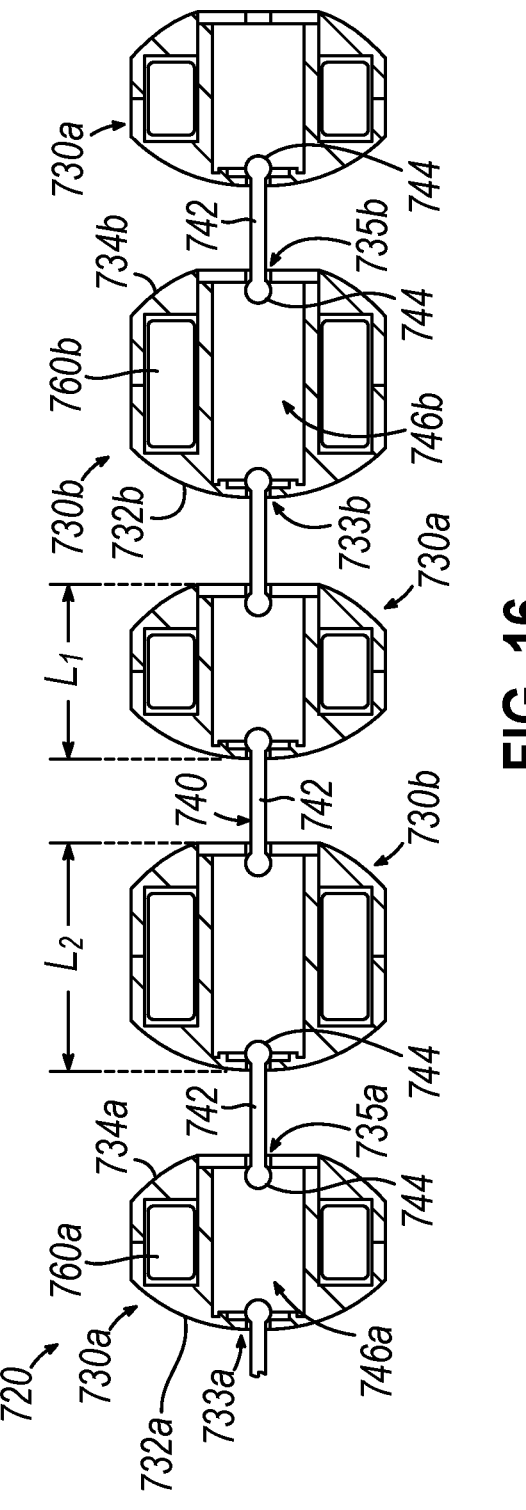
FIG. 16 depicts a top, cross-sectional view of a portion of another exemplary sphincter augmentation device, showing beads of the device having circumferentially-alternating lengths for accommodating differently-sized magnets.
Figure 17A:
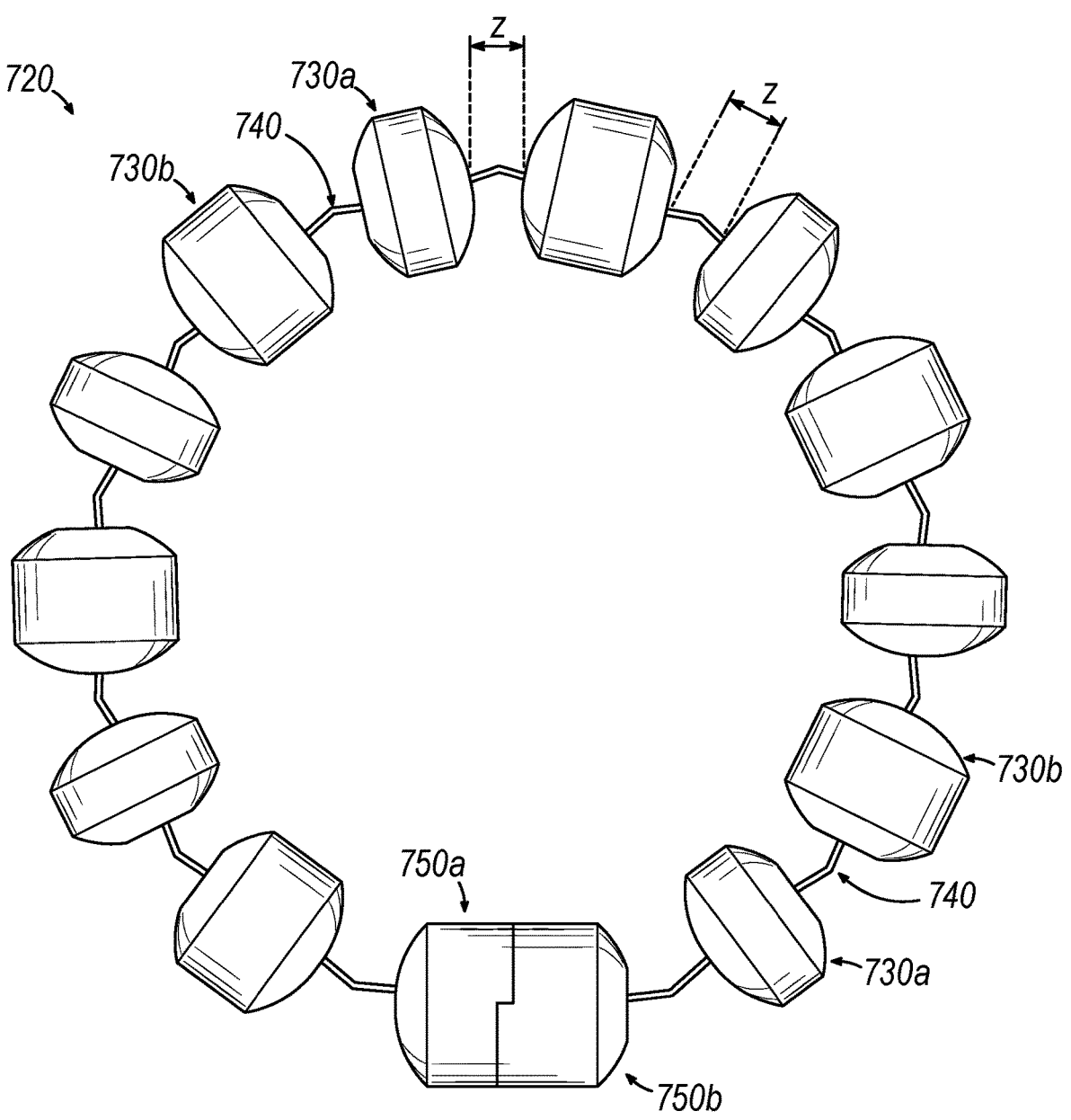
FIG. 17A depicts a top plan view of the sphincter augmentation device of FIG. 16, showing the device in a fully expanded state.
Figure 17B:
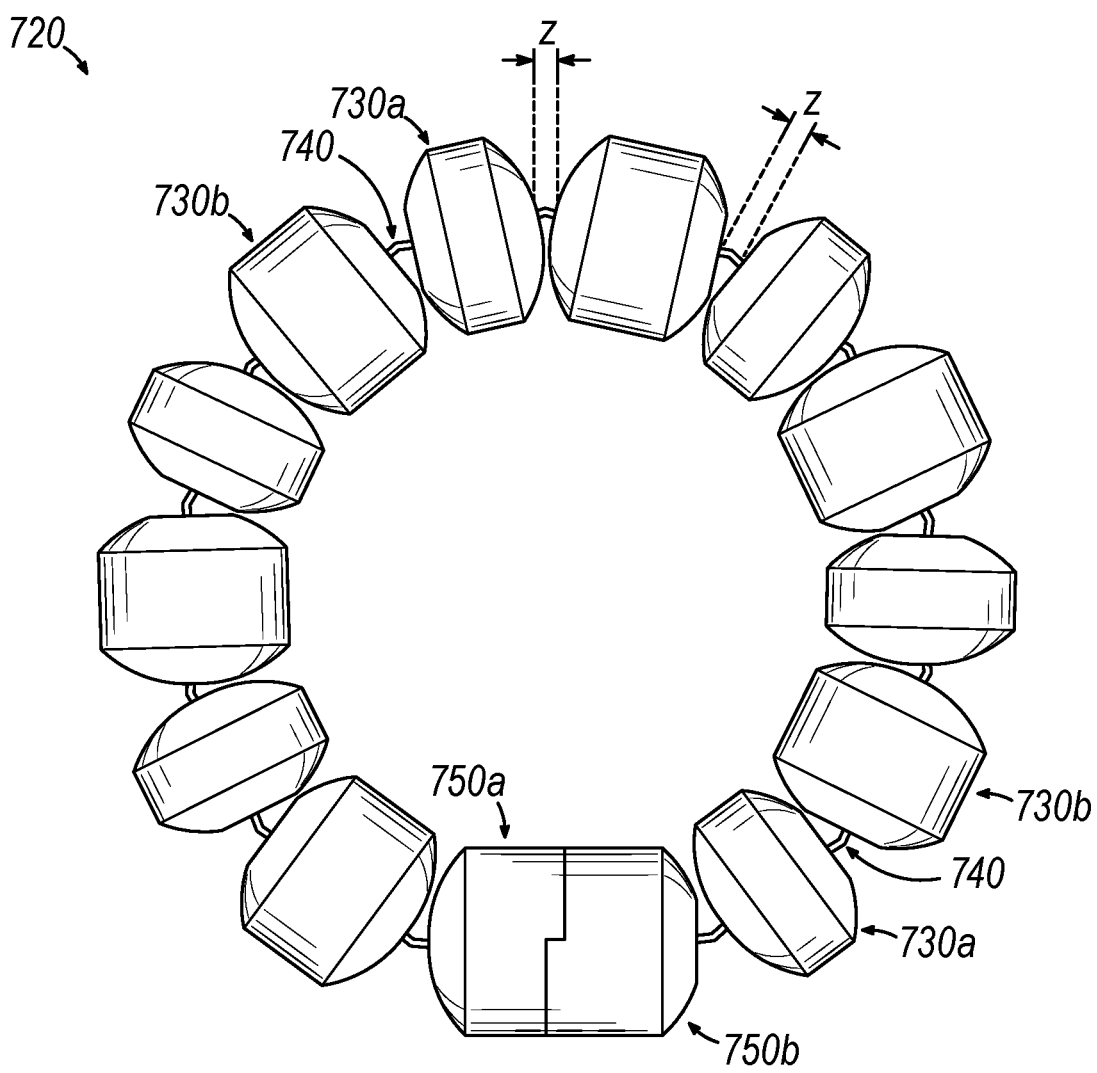
FIG. 17B depicts a top plan view of the sphincter augmentation device of FIG. 16, showing the device in a fully contracted state.

FIGS. 16-17B show another exemplary sphincter augmentation device (720) including a plurality of beads (730a, 730b) and interconnection elements in the form of links (740). Beads (730a, 730b) and links (740) are similar to beads (30) and links (40) described above, respectively, except as otherwise described below. In this regard, beads (730a, 730b) of this example each include a first housing (732a, 732b), a second housing (734a, 734b), at least one annular or toroidal rare-earth permanent magnet (760a, 760b), a chamber (746a, 746b) that is configured to receive a portion of a respective pair of links (740), a first opening (733a, 733b) at a first end of chamber (746a, 746b), and a second opening (735a, 735b) at a second end of chamber (746a, 746b). Links (740) of this example each include a main body in the form of a generally cylindrical wire (742) with free ends which each terminate in a restriction feature in the form of a ball tip (744) and movably (e.g., slidably) join together a respective pair of beads (730a, 730b).

Sphincter augmentation device (720) of the present version also includes opposing fastener features in the form of complementary clasp structures (750a, 750b) coupled to respective beads (730) via corresponding links (740) to allow the ends of device (720) to be coupled together to form a loop, as shown in FIGS. 17A-17B. Clasp structures (750a, 750b) may be constructed and operable in accordance with at least some of the teachings of U.S. Pat. No. 11,071,619, entitled "Coupling Assembly for Implantable Sphincter Assistance Device," U.S. Pat. No. 10,716,570, entitled "Magnetic Restraint Mechanism for a Sphincter Assist Device," and/or U.S. Pub. No. 2011/0098731, now abandoned, entitled "Magnetically Assisted Clasps for Prosthetic Implants, and Related Methods."

In the example shown, the plurality of beads (730a, 730b) includes a plurality of first beads (730a) each having a first length ($L_1$) and a plurality of second beads (730b) each having a second length ($L_2$) less than the first length ($L_1$). As shown, first and second beads (730a, 730b) are arranged in an alternating manner, such that each first bead (730a) is positioned between a pair of second beads (730b) and each second bead (730b) is positioned between a pair of first beads (730a). For example, when the ends of device (720) are coupled together to form a loop, first and second beads (730a, 730b) may alternate with each other circumferentially with respect to the loop, as shown in FIGS. 17A-17B. Due to the differing lengths ($L_1$, $L_2$) of beads (730a, 730b), the distance between the centerline of each first bead (730a) and the ball tips (744) positioned within the respective chamber (746a) may be different from (e.g., greater than) the distance between the centerline of each second bead (730b) and the ball tips (744) positioned within the respective chamber (746b), at least when sphincter augmentation device (720) is in one of the fully contracted state (FIG. 17B) or the fully expanded state (FIG. 17A).

By circumferentially alternating between first and second lengths ($L_1$, $L_2$), beads (730a, 730b) may provide a reduced minimum inner diameter of sphincter augmentation device (720) when the ends of device (720) are coupled together to form a loop and device (720) is in a fully-contracted state (FIG. 17B) without substantially reducing the constrictive force provided thereby, at least by comparison to a sphincter augmentation device having only second beads (730b). In some versions, such circumferential alternating between first and second lengths ($L_1$, $L_2$) may also allow the sizes of magnets (760a, 760b) to circumferentially alternate, thereby permitting different magnetic fields to be generated between adjacent magnets (760a, 760b) than those generated between adjacent, uniformly-sized magnets, such as magnets (60) of device (20). The different sizes of magnets (760a, 760b) may be selected based on the anatomy of a particular patient to provide predetermined magnetic fields for achieving a desired constriction force for that patient. In any event, a plurality of expandable and contractable zones (Z) are defined at substantially equal intervals about the circumference of device (720), and, more particularly, between respective pairs of circumferentially-adjacent beads (730a, 730b). As shown, zones (Z) may expand and contract at a uniform rate and also may be equally sized when device (720) is in either the fully expanded state (FIG. 17A) or the fully contracted state (FIG. 17B), due to the circumferentially-alternating arrangement of magnets (760a, 760b), and may thereby promote homogeneity of the force applied to the tissue by device (720).

C. Exemplary Device with Asymmetric Beads

Figure 18A:
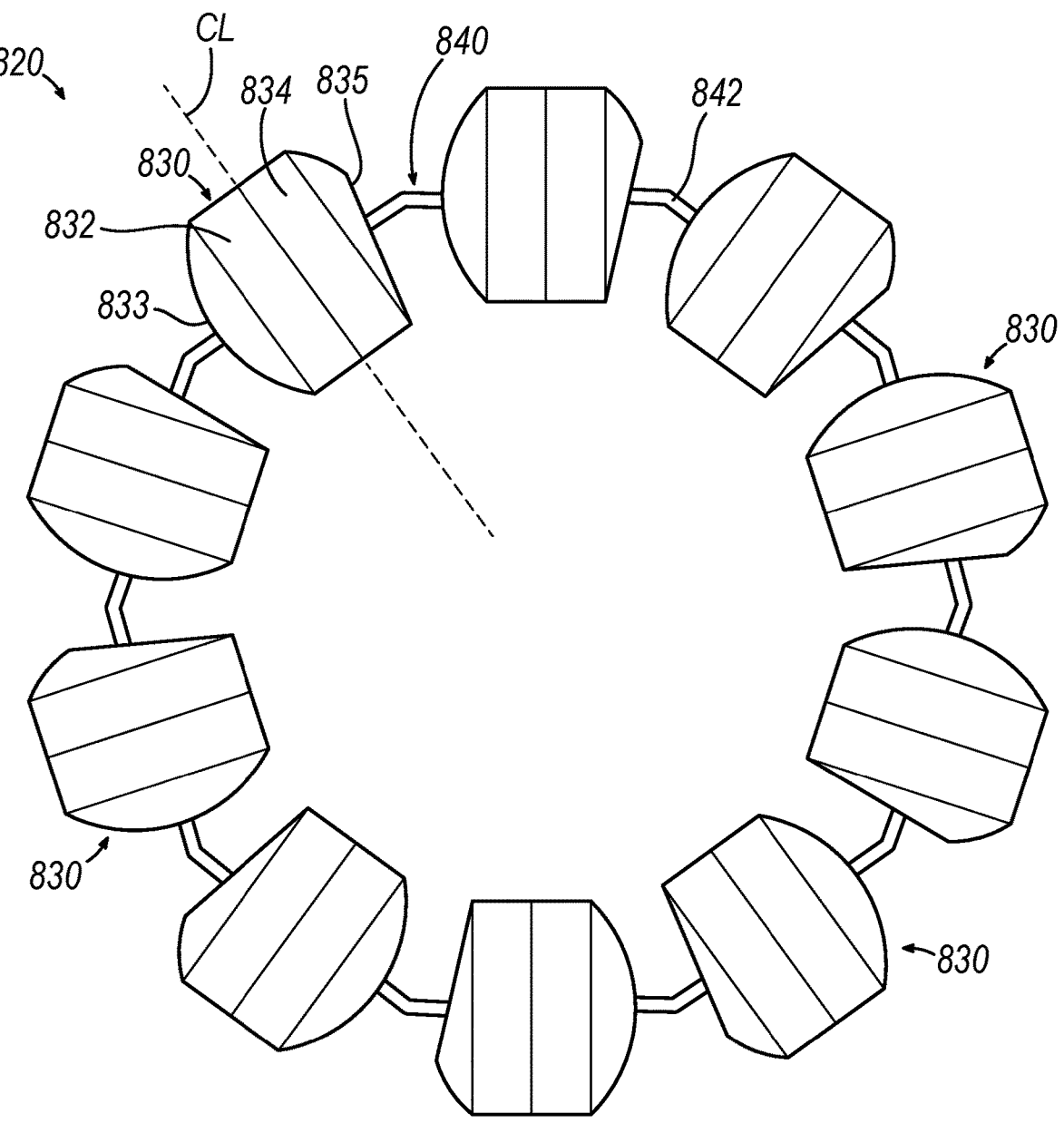
FIG. 18A depicts a top plan view of another exemplary sphincter augmentation device having beads with asymmetric configurations for reducing an inner diameter of the device when in a fully contracted state, showing the device in a fully expanded state.
Figure 18B:
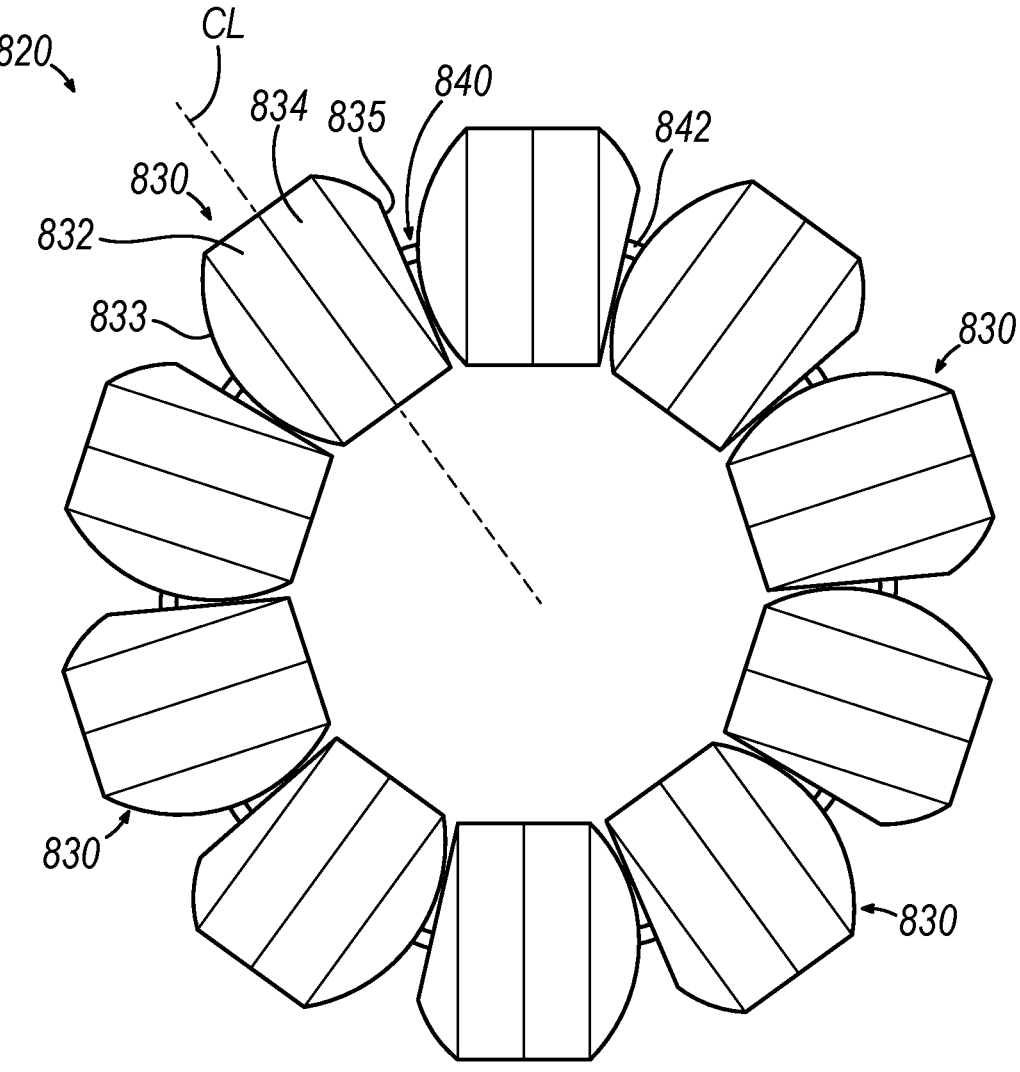
FIG. 18B depicts a top plan view of the sphincter augmentation device of FIG. 18A, showing the device in the fully contracted state.

FIGS. 18A-18B show another exemplary sphincter augmentation device (820) including a plurality of beads (830) and interconnection elements in the form of links (840). Beads (830) and links (840) are similar to beads (30) and links (40) described above, respectively, except as otherwise described below. In this regard, beads (830) of this example each include first and second housings (832, 834), at least one annular or toroidal rare-earth permanent magnet (not shown), such as magnet (60), a chamber (not shown) that is configured to receive a portion of a respective pair of links (840), similar to chamber (36), and a pair of openings (not shown) at respective ends of the chamber. Links (840) of this example each include a main body in the form of a generally cylindrical wire (842) with free ends which each terminate in a restriction feature in the form of a ball tip (not shown) and movably (e.g., slidably) join together a respective pair of beads (830).

Sphincter augmentation device (820) may include opposing fastener features in the form of complementary clasp structures (not shown) to allow the ends of device (820) to be coupled together to form a loop, as shown in FIGS. 18A-18B. Such clasp structures may be constructed and operable in accordance with at least some of the teachings of U.S. Pat. No. 11,071,619, entitled "Coupling Assembly for Implantable Sphincter Assistance Device," U.S. Pat. No. 10,716,570, entitled "Magnetic Restraint Mechanism for a Sphincter Assist Device," and/or U.S. Pub. No. 2011/0098731, now abandoned, entitled "Magnetically Assisted Clasps for Prosthetic Implants, and Related Methods."

In the example shown, each bead (830) is asymmetrical about its central plane (CP). In this regard, each first housing (832) includes a convex end surface (833); and each second housing (834) includes a chamfered end surface (835) which tapers radially inwardly relative the loop formed by device (820). As shown, each convex end surface (833) is configured to abut or otherwise confront the chamfered end surface (835) of the corresponding counterclockwise-adjacent bead (830). By tapering radially inwardly, chamfered end surfaces (835) may provide a reduced minimum inner diameter of sphincter augmentation device (820) when the ends of device (820) are coupled together to form a loop and device (820) is in a fully-contracted state (FIG. 18B), at least by comparison to a sphincter augmentation device having only convex end surfaces (833) on each housing (832, 834). Such a reduction in minimum diameter may promote proper engagement of each bead (830) with the tissue when device (820) is in the fully-contracted state (FIG. 18B); and may thereby promote homogeneity of the force applied to the tissue by device (820) at least when device (820) is in the fully-contracted state. In some versions, chamfered end surfaces (835) may assist with maintaining sphincter augmentation device (820) in a generally circular looped configuration, such as by urging the corresponding clockwise-adjacent bead (830) in a radially inward direction. In other versions, end surface (835) may be concave in addition to or instead of tapering radially inwardly to provide a reduced minimum inner diameter of device (820) at the fully-contracted state.

D. Exemplary Device with Links Having Circumferentially-Alternating Lengths

Figure 19:
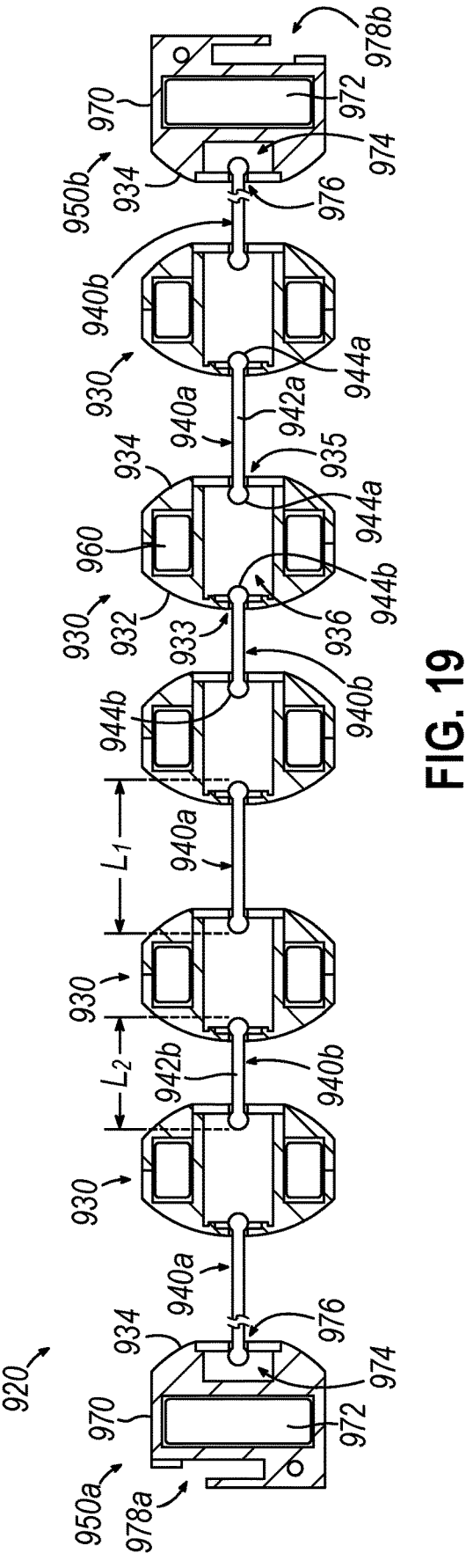
FIG. 19 depicts a top, cross-sectional view of another exemplary sphincter augmentation device, showing links of the device having circumferentially-alternating lengths for providing homogeneous dilation and contraction of the device.
Figure 20A:
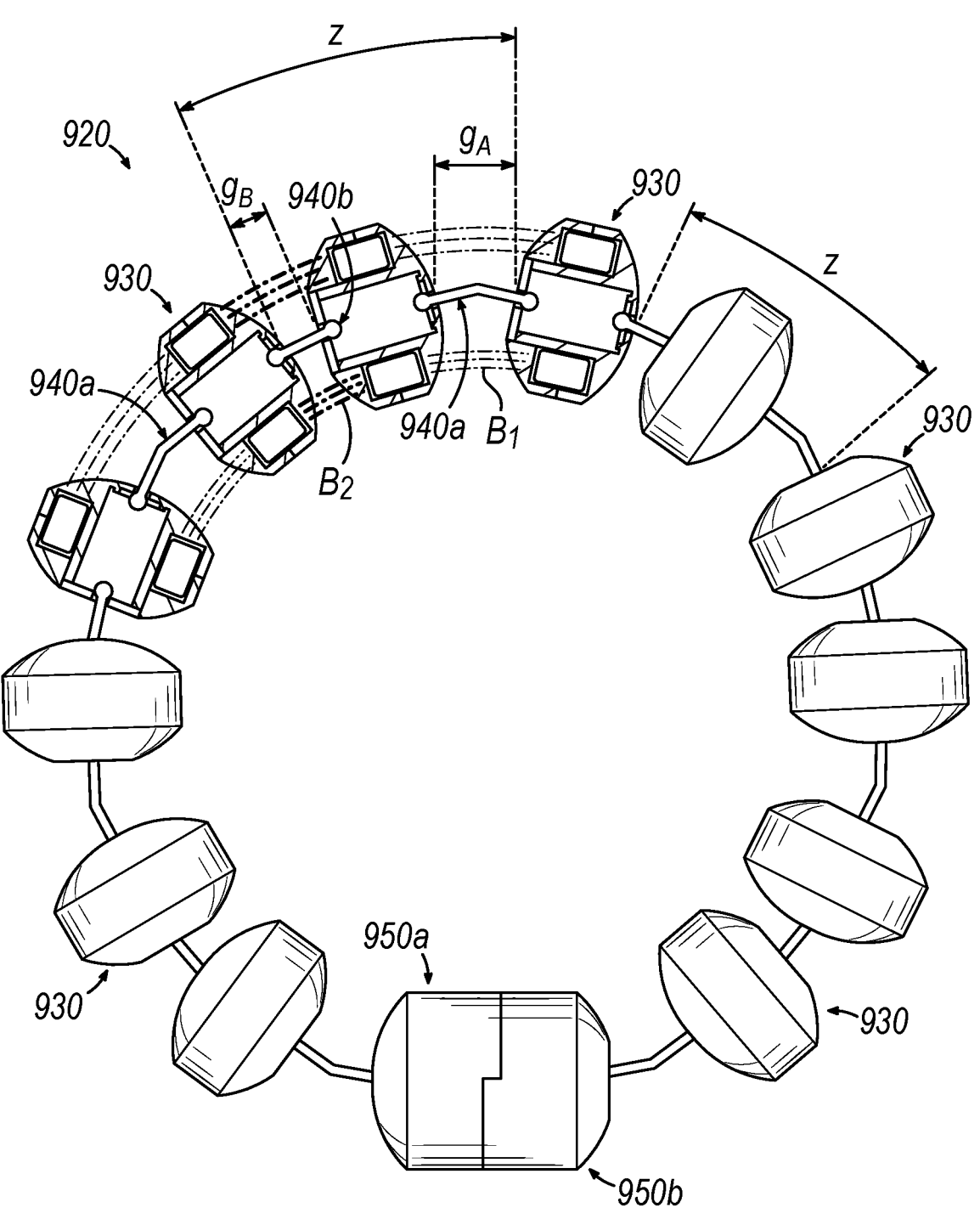
FIG. 20A depicts a top plan view of the sphincter augmentation device of FIG. 19, showing the device in a fully expanded state.
Figure 20B:
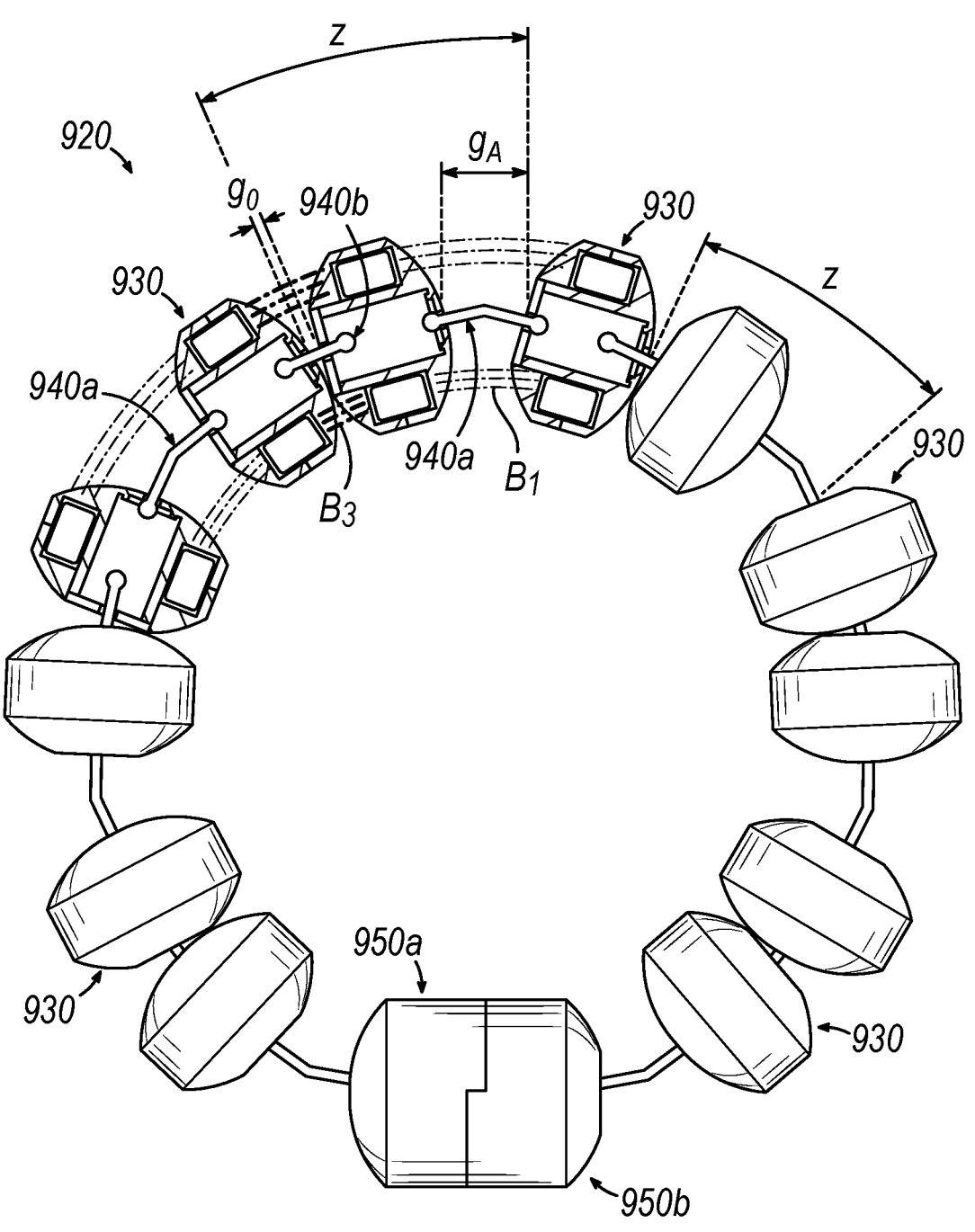
FIG. 20B depicts a top plan view of the sphincter augmentation device of FIG. 19, showing the device in an intermediate state.
Figure 20C:
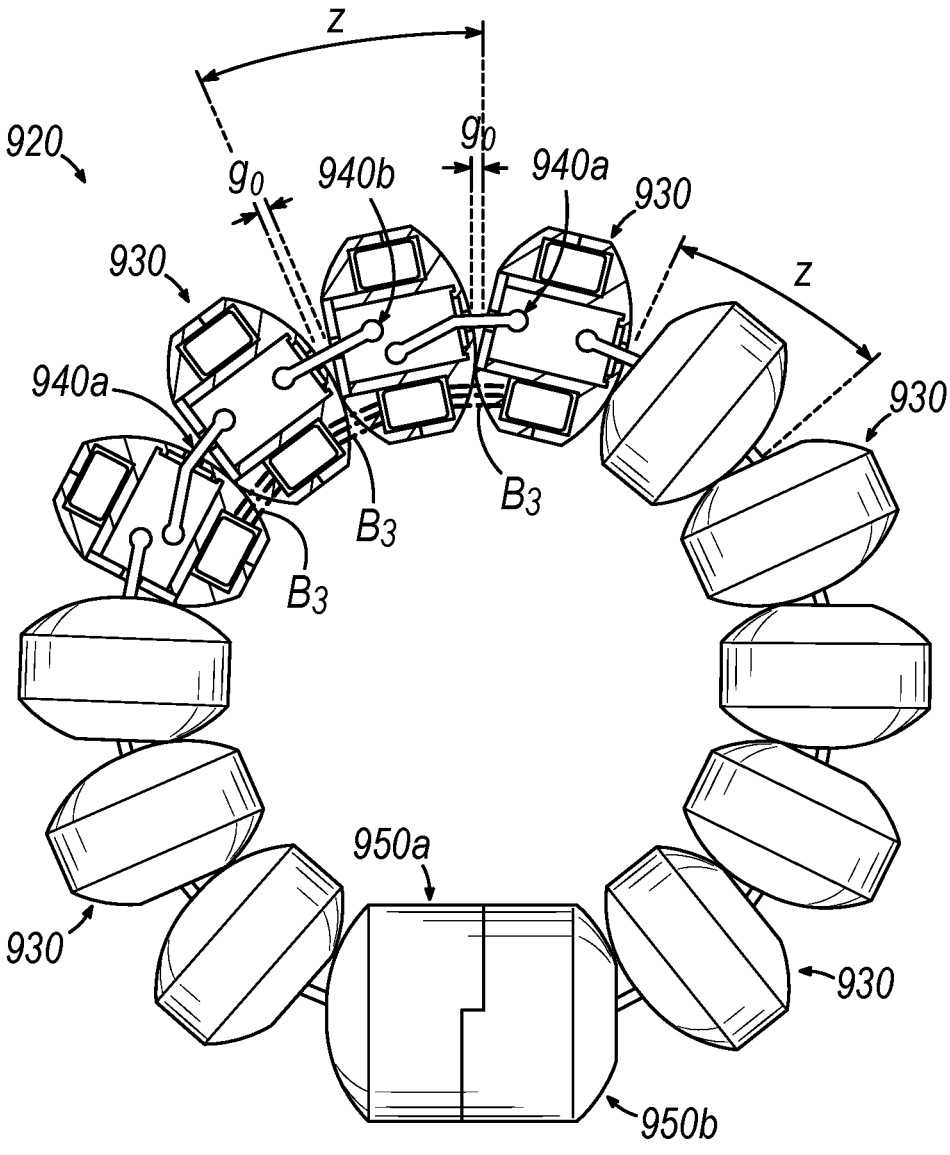
FIG. 20C depicts a top plan view of the sphincter augmentation device of FIG. 19, showing the device in a fully contracted state.

FIGS. 19-20C show another exemplary sphincter augmentation device (920) including a plurality of beads (930) and interconnection elements in the form of links (940a, 940b). Beads (930) and links (940a, 940b) are similar to beads (30) and links (40) described above, respectively, except as otherwise described below. In this regard, beads (930) of this example each include a pair of housings (932, 934), at least one annular or toroidal rare-earth permanent magnet (960), a chamber (936) that is configured to receive a portion of a respective pair of links (940a, 940b), and a pair of openings (933, 935) at respective ends of chamber (936). Links (940a, 940b) of this example each include a main body in the form of a generally cylindrical wire (942a, 942b) with free ends which each terminate in a restriction feature in the form of a ball tip (944a, 944b) and movably (e.g., slidably) join together a respective pair of beads (930).

Sphincter augmentation device (920) of the present version also includes opposing fastener features in the form of complementary clasp structures (950a, 950b) coupled to respective beads (930) via corresponding links (940a, 940b) to allow the ends of device (920) to be coupled together to form a loop, as shown in FIGS. 20A-20C. Clasp structures (950a, 950b) of this example each include a housing (970), a disc-shaped rare-earth permanent magnet (972), a chamber (974) that is configured to receive a portion of a respective link (940a, 940b), an opening (976) at a respective end of chamber (974), and at least one connection element (978a, 978b) configured to mechanically interconnect with the at least one connection element (978a, 978b) of the other clasp structure (950a, 950b) to resist pulling apart of clasp structures (950a, 950b) from each other. In this regard, magnets (972) may have a polar alignment such that magnets (972) are attracted to each other when connection elements (978a, 978b) are interconnected with each other, to thereby help connection elements (978a, 978b) become and stay interconnected with each other. In addition to the foregoing, clasp structures (950a, 950b) may be constructed and operable in accordance with at least some of the teachings of U.S. Pat. No. 11,071,619, entitled "Coupling Assembly for Implantable Sphincter Assistance Device," U.S. Pat. No. 10,716,570, now abandoned, entitled "Magnetic Restraint Mechanism for a Sphincter Assist Device," and/or U.S. Pub. No. 2011/0098731, entitled "Magnetically Assisted Clasps for Prosthetic Implants, and Related Methods."

In the example shown, the plurality of links (940a, 940b) includes a plurality of first links (940a) each having a first length ($L_1$) and a plurality of second links (940b) each having a second length ($L_2$) less than the first length ($L_1$). In some versions, the first length ($L_1$) may be approximately 0.140 inch and the second length ($L_2$) may be approximately 0.100 inch. In addition, or alternatively, wire (942a) of each first link (940*a*) may be pre-bent to form an obtuse angle (not shown). As shown, first and second links (940*a*, 940*b*) are arranged in an alternating manner, such that each first link (940*a*) is positioned between a pair of second links (940*b*) and each second link (940*b*) is positioned between a pair of first links (940*a*). For example, when the ends of device (920) are coupled together to form a loop, first and second links (940*a*, 940*b*) may alternate with each other circumferentially with respect to the loop, as shown in FIGS. 20A-20C.

By circumferentially alternating between first and second lengths ($L_1$, $L_2$), links (940*a*, 940*b*) may provide a reduced maximum inner diameter of sphincter augmentation device (920) thereby reducing the maximum displacement between adjacent beads (930), at least by comparison to a sphincter augmentation device having only first links (940*a*). In some versions, this may cause an increase in the number of adjacent beads (930) which separate from each other during expansion of sphincter augmentation device (920), such as during a swallowing action of the patient.

As shown in FIG. 20A, sphincter augmentation device (920) may initially be in a fully expanded state, such as when a relatively large bolus of food passes through a region of a patient's LES (6) around which sphincter augmentation device (920) is installed. In this state, each pair of adjacent beads (930) that are joined together by first links (940*a*) are spaced apart from each other by a first gap ($g_A$) corresponding to the first length ($L_1$), and each pair of adjacent beads (930) that are joined together by second links (940*b*) are spaced apart from each other by a second gap ($g_B$) corresponding to the second length ($L_2$), such that the first gap ($g_A$) is greater than the second gap ($g_B$). Due to this relative positioning of beads (930), magnets (960) of adjacent beads (930) that are joined together by first links (940*a*) may generate a first magnetic field ($B_1$) which applies a first magnetic force between such magnets (960). Also due to this relative positioning of beads (930), magnets (960) of adjacent beads (930) that are joined together by second links (940*b*) may generate a second magnetic field ($B_2$) which applies a second magnetic force between such magnets (960) that is greater than the first magnetic force applied by first magnetic field ($B_1$).

As shown in FIG. 20B, sphincter augmentation device (920) may subsequently be contracted to an intermediate state (e.g., when a relatively small bolus of food or drink passes through the region of the LES (6) at which sphincter augmentation device (920) is installed. Due to the relatively high magnitude of the second magnetic force compared to the first magnetic force, each pair of adjacent beads (930) that are joined together by first links (940*a*) may remain spaced apart from each other by the first gap ($g_A$), while each pair of adjacent beads (930) that are joined together by second links (940*b*) may be approximated toward each other by the second magnetic force applied by the second magnetic field ($B_2$) to leave a negligible gap ($g_0$) therebetween. As a result, magnets (960) of adjacent beads (930) that are joined together by second links (940*b*) may generate a third magnetic field ($B_3$) which applies a third magnetic force between such magnets (960) that is greater than the second magnetic force applied by second magnetic field ($B_2$), and magnets (960) of adjacent beads (930) that are joined together by first links (940*a*) may continue to generate first magnetic field ($B_1$) which applies a first magnetic force between such magnets (960).

As shown in FIG. 20C, sphincter augmentation device (920) may subsequently be contracted to a fully contracted state (e.g., when nothing is passing through the region of the LES (6) at which sphincter augmentation device (920) is installed). Due to the negligible gap ($g_0$) between each pair of adjacent beads (930) that are joined together by second links (940*b*), each pair of adjacent beads (930) that are joined together by first links (940*a*) may be drawn toward each other by the first magnetic force applied by the first magnetic field ($B_1$) to similarly leave a negligible gap ($g_0$) therebetween. As a result, magnets (960) of adjacent beads (930) that are joined together by first links (940*a*) may also generate the third magnetic field ($B_3$) which applies the third magnetic force between such magnets (960), and magnets (960) of adjacent beads (930) that are joined together by second links (940*b*) may continue to generate the third magnetic field ($B_3$) which applies the third magnetic force between such magnets (960). Thus, the third magnetic force may be applied equally between each pair of adjacent beads (930).

As shown in FIGS. 20A-20C, a plurality of expandable and contractable zones (Z) are defined at substantially equal intervals about the circumference of device (920), and, more particularly, between respective pairs of circumferentially-alternating beads (930) such that each zone (Z) includes a respective pair of circumferentially-adjacent links (940*a*, 940*b*). As shown, zones (Z) may expand and contract at a uniform rate and also may be equally sized when device (920) is in either the fully expanded state (FIG. 20A) or the fully contracted state (FIG. 20B), due to the circumferentially-alternating arrangement of links (940*a*, 940*b*), and may thereby promote homogeneity of the force applied to the tissue by device (920). In this regard, slight variations in the sizes of the gaps between adjacent beads (930) that are joined together by first links (940*a*) (e.g., due to minor manufacturing defects or other imperfections of such beads (930), magnets (960) thereof, or first links (940*a*)) may be at least partially compensated for by slight variations in the sizes of the gaps between adjacent beads (930) that are joined together by second links (940*b*) (e.g., due to minor manufacturing defects or other imperfections of such beads (930), magnets (960) thereof, or second links (940*b*)), and vice-versa, such that the zones (Z) themselves may expand and contract at a uniform rate and also may be equally sized when device (920) is in either the fully expanded state (FIG. 20A) or the fully contracted state (FIG. 20B) despite such slight variations in the sizes of gaps.

E. Exemplary Devices with Beads Having Staggered Link Openings

Figure 21:
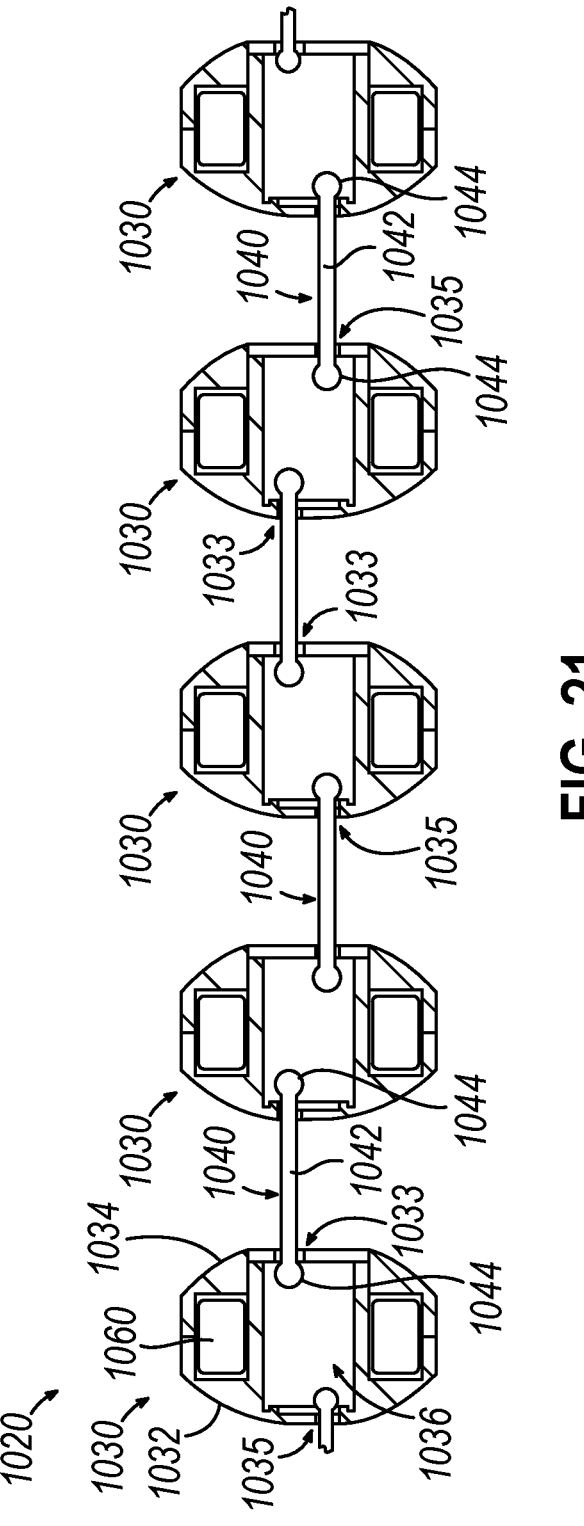
FIG. 21 depicts a top, cross-sectional view of a portion of another exemplary sphincter augmentation device, showing beads of the device having angularly offset link openings for reducing a diameter of the device when in a fully contracted state.
Figure 22A:
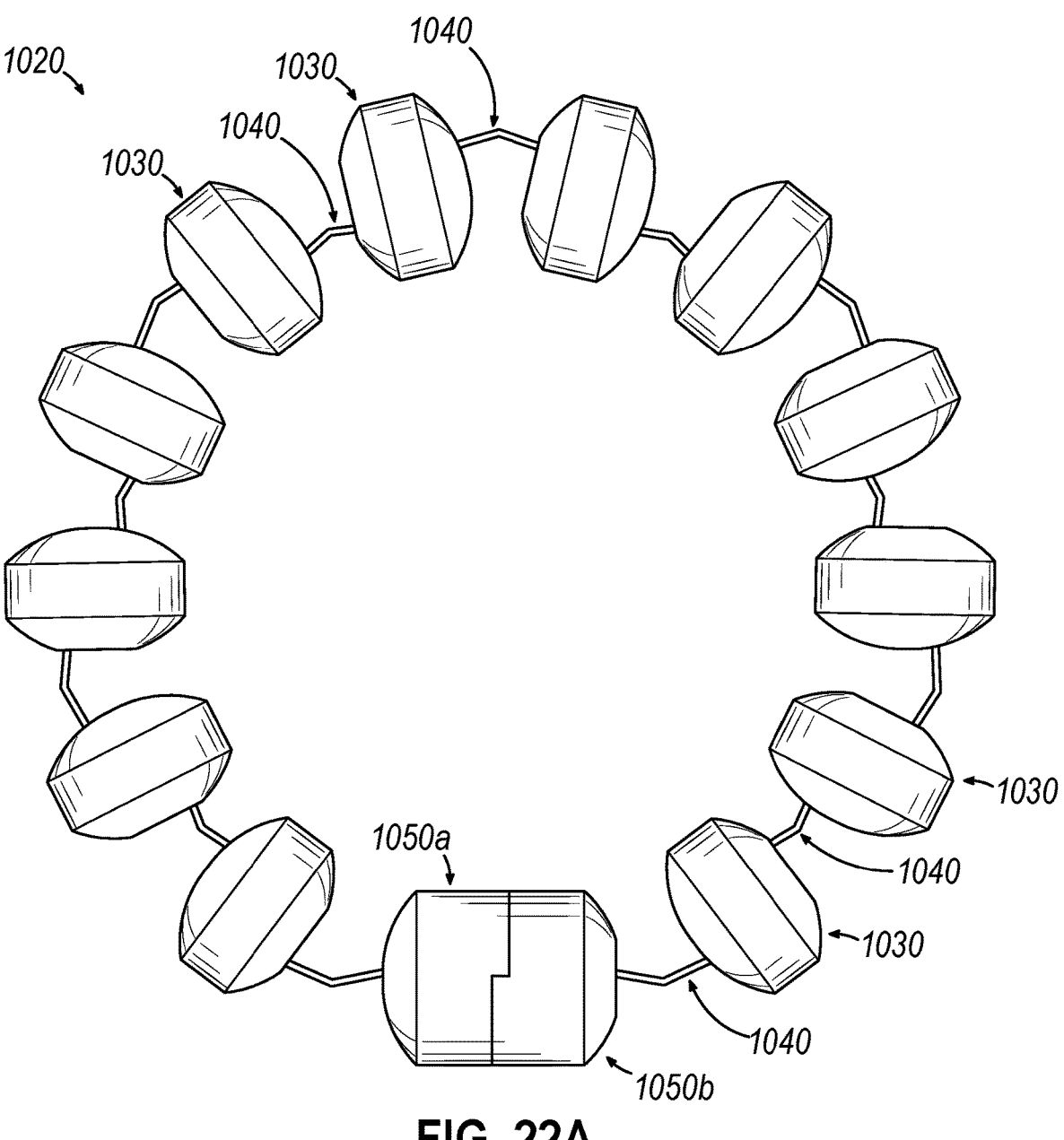
FIG. 22A depicts a top plan view of the sphincter augmentation device of FIG. 21, showing the device in a fully expanded state.
Figure 22B:
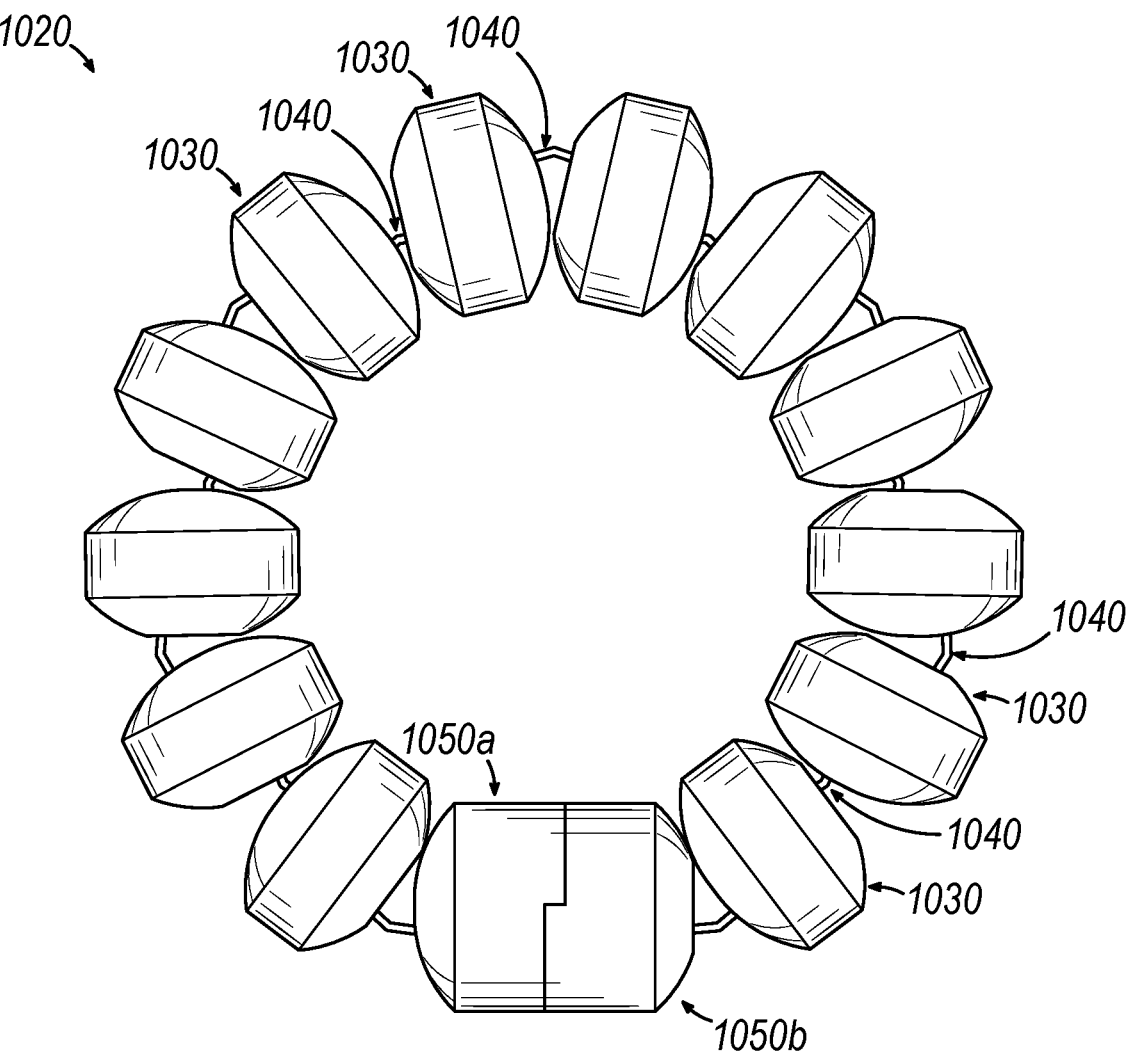
FIG. 22B depicts a top plan view of the sphincter augmentation device of FIG. 21, showing the device in the fully contracted state.

FIGS. 21-22B show another exemplary sphincter augmentation device (1020) including a plurality of beads (1030) and interconnection elements in the form of links (1040). Beads (1030) and links (1040) are similar to beads (30) and links (40) described above, respectively, except as otherwise described below. In this regard, beads (1030) of this example each include a pair of housings (1032, 1034), at least one annular or toroidal rare-earth permanent magnet (1060), a chamber (1036) that is configured to receive a portion of a respective pair of links (1040), and first and second openings (1033, 1035) at respective ends of chamber (1036). Links (1040) of this example each include a main body in the form of a generally cylindrical wire (1042) with free ends which each terminate in a restriction feature in the form of a ball tip (1044) and movably (e.g., slidably) join together a respective pair of beads (1030).

Sphincter augmentation device (1020) of the present version also includes opposing fastener features in the form of complementary clasp structures (1050*a*, 1050*b*) coupled to respective beads (1030) via corresponding links (1040) to allow the ends of device (1020) to be coupled together to form a loop, as shown in FIGS. 22A-22B. Clasp structures (1050a, 1050b) may be constructed and operable in accordance with at least some of the teachings of U.S. Pat. No. 11,071,619, entitled "Coupling Assembly for Implantable Sphincter Assistance Device," U.S. Pat. No. 10,716,570, entitled "Magnetic Restraint Mechanism for a Sphincter Assist Device," and/or U.S. Pub. No. 2011/0098731, now abandoned, entitled "Magnetically Assisted Clasps for Prosthetic Implants, and Related Methods."

In the example shown, first opening (1033) of each bead (1030) is offset from the respective second opening (1035), such that when the ends (not shown) of device (1020) are coupled together to form a loop, first opening (1033) of each bead (1030) may be angularly offset from the respective second opening (1035) with respect to the loop, as shown in FIGS. 22A-22B. For example, each first opening (1033) may be positioned radially outwardly relative to the respective second opening (1035) to be closer to an outer diameter the loop formed by device (1020); or may be positioned radially inwardly relative to the respective second opening (1035) to be closer to an inner diameter of the loop formed by device (1020). In the example shown, each link (1040) extends through a corresponding pair of first openings (1033) or second openings (1035) such that some links (1040) are positioned relatively radially outwardly while other links (1040) are positioned relatively radially inwardly when the ends of device (1020) are coupled together to form a loop. For example, when the ends of device (1020) are coupled together to form a loop, links (1040) may alternate between being relatively radially outward and relatively radially inward circumferentially with respect to the loop, as shown in FIGS. 22A-22B.

Figure 23:
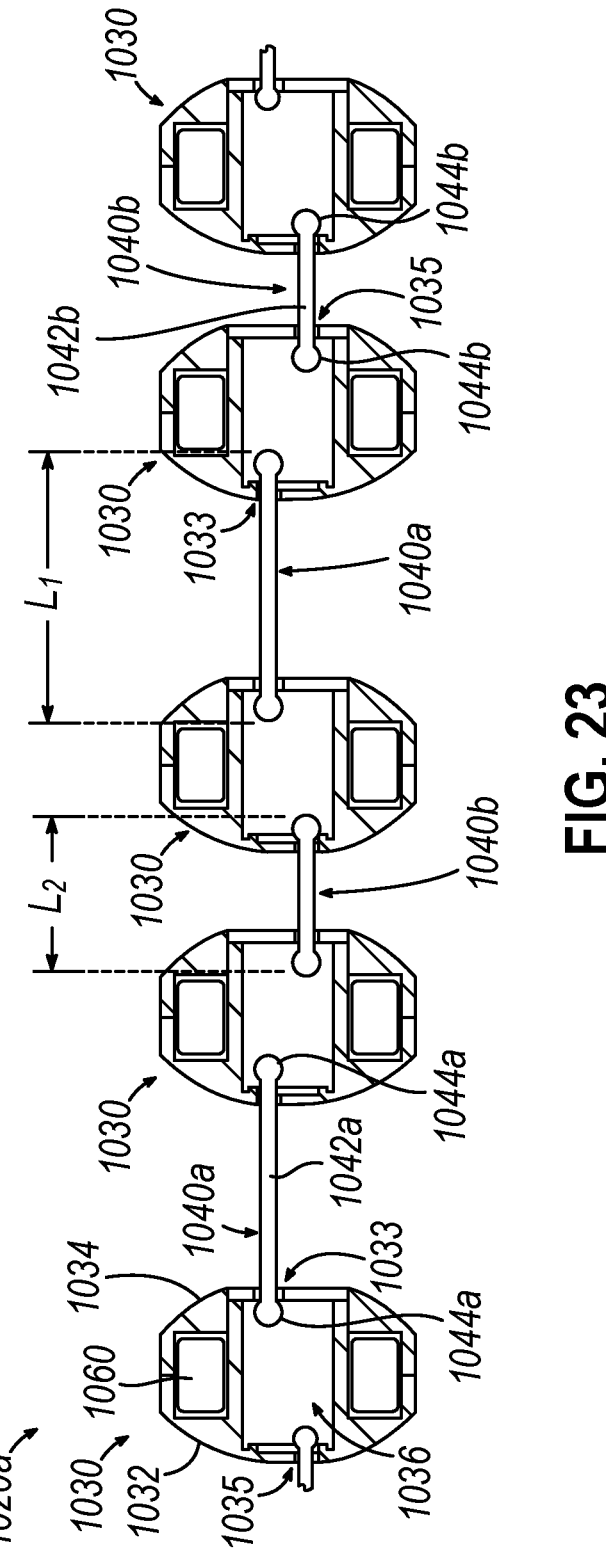
FIG. 23 depicts a top, cross-sectional view of a portion of another exemplary sphincter augmentation device, showing beads of the device having angularly offset link openings for reducing a diameter of the device in a fully contracted state and further showing links of the device having circumferentially-alternating lengths.
Figure 24A:
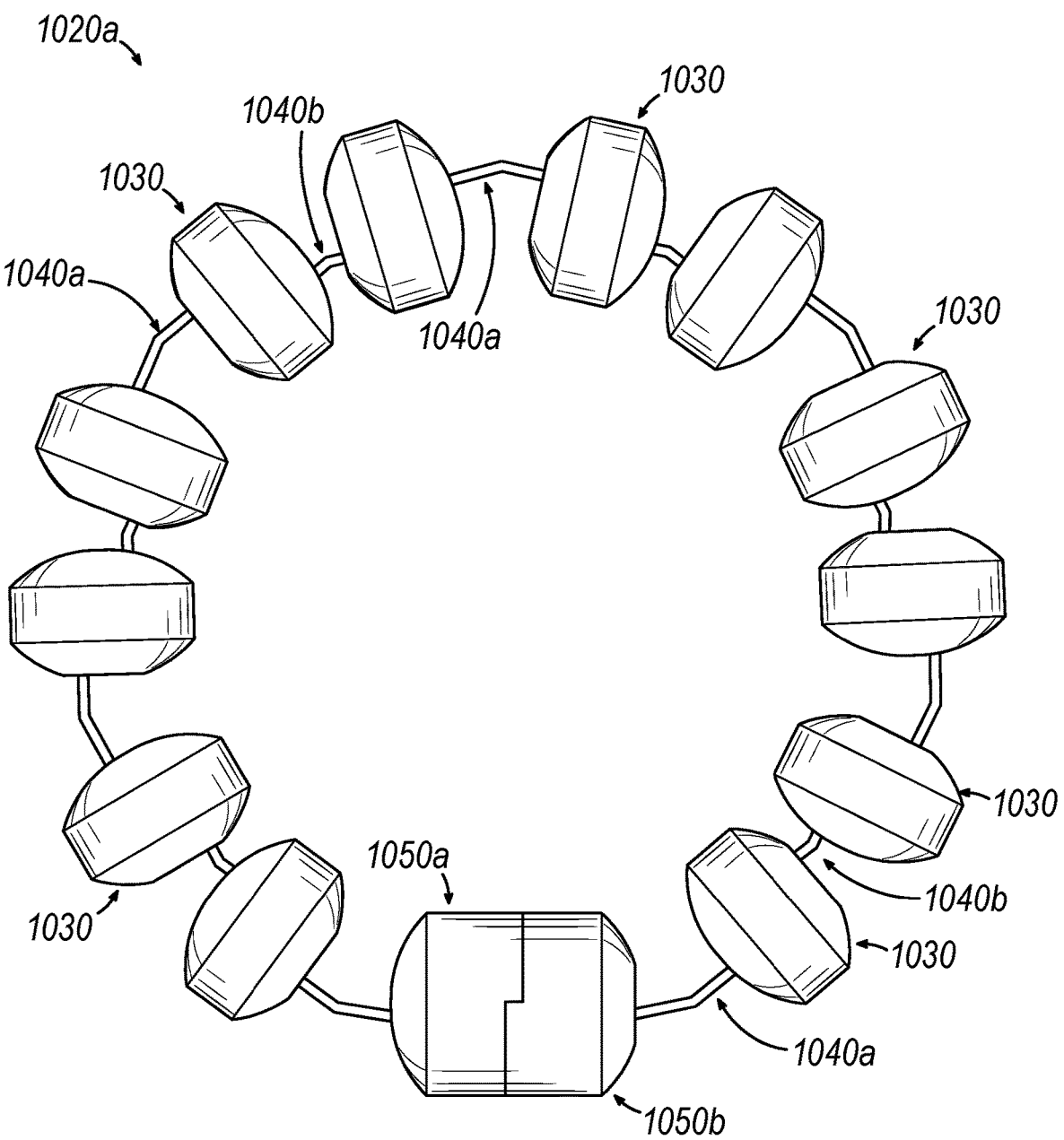
FIG. 24A depicts a top plan view of the sphincter augmentation device of FIG. 23, showing the device in a fully expanded state.
Figure 24B:
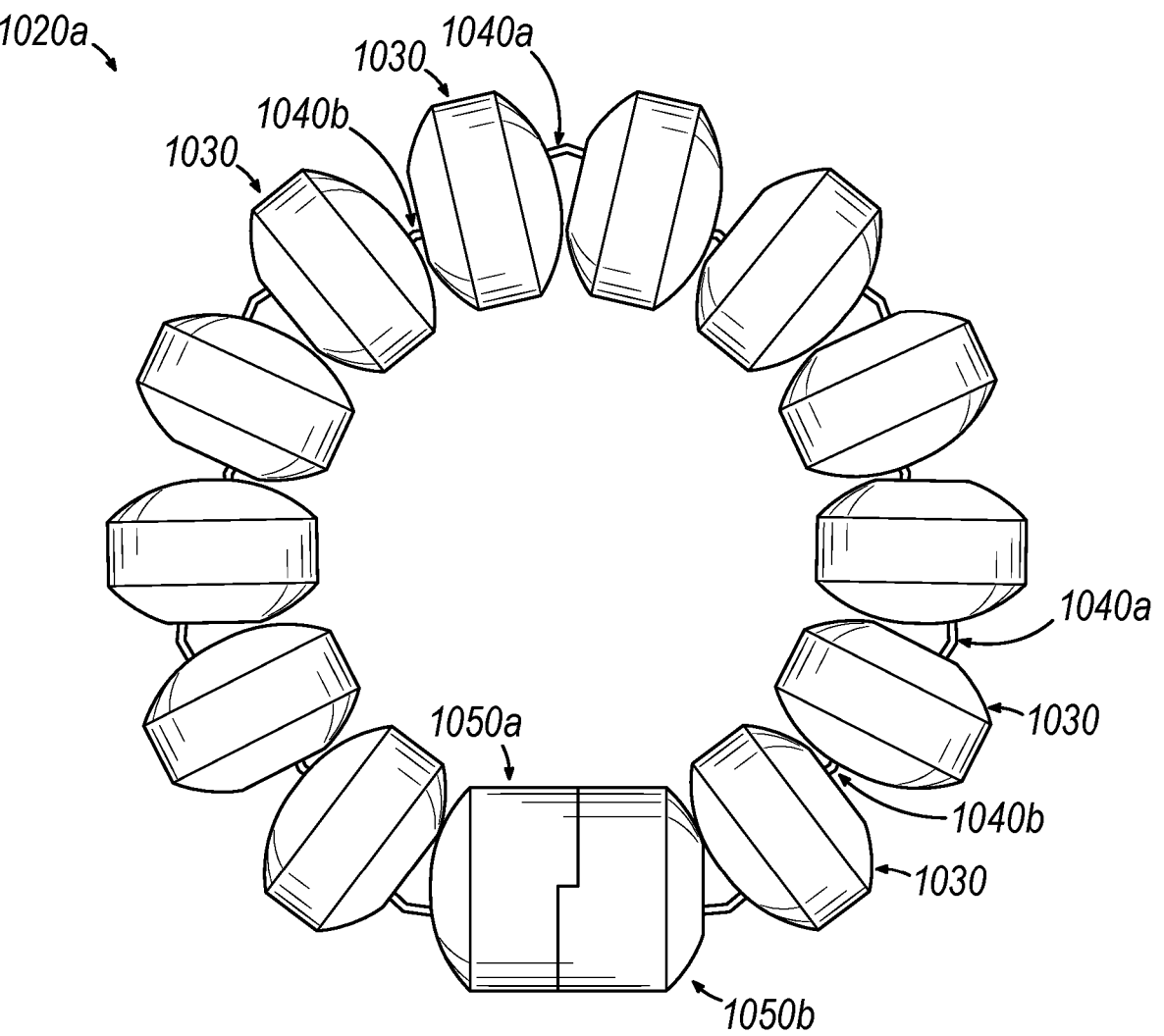
FIG. 24B depicts a top plan view of the sphincter augmentation device of FIG. 23, showing the device in the fully contracted state.

FIGS. 23-24B depict another exemplary sphincter augmentation device (1020a) including a plurality of beads (1030) and interconnection elements in the form of links (1040a, 1040b). Links (1040a, 1040b) of this example each include a main body in the form of a generally cylindrical wire (1042a, 1042b) with free ends which each terminate in a restriction feature in the form of a ball tip (1044a, 1044b) and movably (e.g., slidably) join together a respective pair of beads (1030). In the example shown, the plurality of links (1040a, 1040b) includes a plurality of first links (1040a) each having a first length (L$_1$) and a plurality of second links (1040b) each having a second length (L$_2$) less than the first length (L$_1$). In some versions, the first length (L$_1$) may be approximately 0.140 inch and the second length (L$_2$) may be approximately 0.100 inch. As shown, first and second links (1040a, 1040b) are arranged in an alternating manner, such that each first link (1040a) is positioned between a pair of second links (1040b) and extends through a corresponding pair of first openings (1033) and each second link (1040b) is positioned between a pair of first links (1040a) and extends through a corresponding pair of second openings (1035). Thus, each first link (1040a) is relatively radially outward, and each second link (1040b) is relatively radially inward with respect to the loop, as shown in FIGS. 23A-23B.

V. Examples of Implantable Sphincter Assistance Devices with Single Use Emergency Release Decoupling Interconnection Link In some instances, it may be desirable to provide improved, robust coupling of the ends of device (20) to form the desired loop. In addition, or alternatively, it may be desirable to simplify dismantling the loop (e.g., by decoupling the ends or midpoints of device (20)), such as for facilitating an emergency removal of device (20). Each of the devices described below may provide one or more these functionalities.

A. Exemplary Device with Quick Release Clasps at Device Ends

Figure 25:
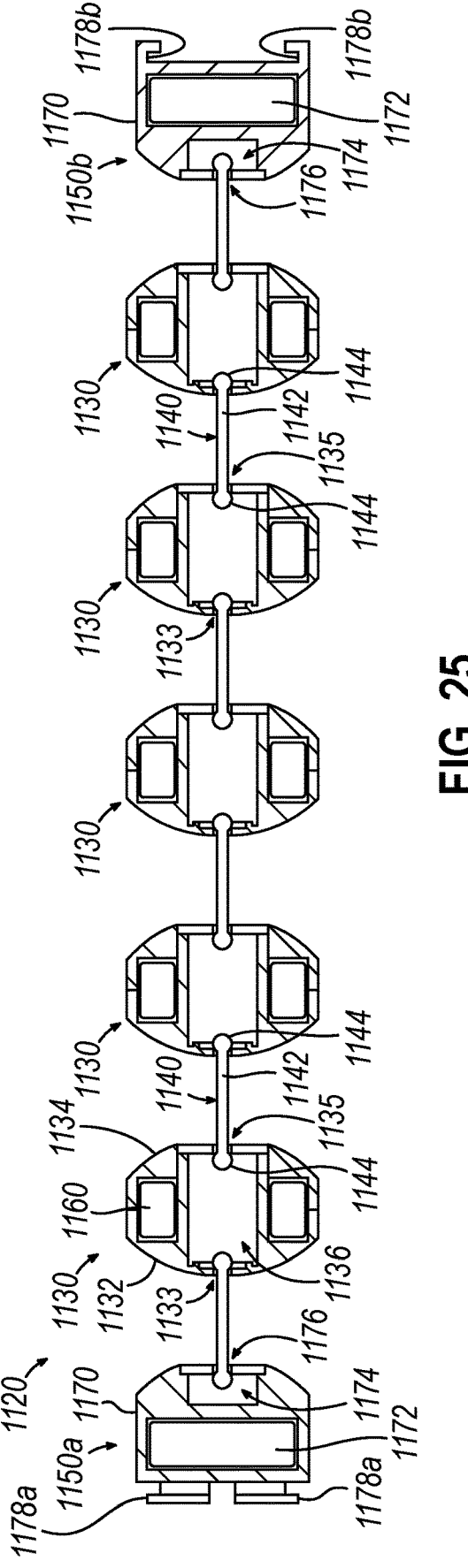
FIG. 25 depicts a top, cross-sectional view of another exemplary sphincter augmentation device, showing clasp structures of the device having quick-release connection elements for coupling ends of the device to form a loop.

FIG. 25 shows another exemplary sphincter augmentation device (1120) including a plurality of beads (1130) and interconnection elements in the form of links (1140). Beads (1130) and links (1140) are similar to beads (30) and links (40) described above, respectively, except as otherwise described below. In this regard, beads (1130) of this example each include a pair of housings (1132, 1134), at least one annular or toroidal rare-earth permanent magnet (1160), a chamber (1136) that is configured to receive a portion of a respective pair of links (1140), and a pair of openings (1133, 1135) at respective ends of chamber (1136). Links (1140) of this example each include a main body in the form of a generally cylindrical wire (1142) with free ends which each terminate in a restriction feature in the form of a ball tip (1144) and movably (e.g., slidably) join together a respective pair of beads (1130).

Sphincter augmentation device (1120) of the present version also includes opposing fastener features in the form of first and second quick-release clasp structures (1150a, 1150b) coupled to respective beads (1130) via corresponding links (1140) to allow the ends of device (1120) to be coupled together to form a loop. Clasp structures (1150a, 1150b) of this example each include a housing (1170), a disc-shaped rare-earth permanent magnet (1172), a chamber (1174) that is configured to receive a portion of a respective link (1140), an opening (1176) at a respective end of chamber (1174), and at least one quick-release connection element (1178a, 1178b). In this regard, first quick-release clasp structure (1150a) includes a pair of quick-release connection elements in the form of flexible tabs (1178a) configured to releasably engage corresponding quick-release connection elements in the form of recesses (1178b) of second quick-release clasp structure (1150b) to thereby couple the ends of device (1120) together to form a loop. Magnets (1172) may have a polar alignment such that magnets (1172) are attracted to each other when connection elements (1178a, 1178b) are interconnected with each other, to thereby help connection elements (1178a, 1178b) become and stay interconnected with each other. In some versions, tabs (1178a) may be biased outwardly into engagement with the corresponding recesses (1178b). In any event, tabs (1178a) may be selectively urged inwardly out of engagement with the corresponding recesses (1178b) in response to application of a threshold pulling force applied between clasp structures (1150a, 1150b) in the circumferential direction (e.g., relative to the loop formed by device (1120)), such as via an instrument, to thereby decouple the ends of device (1120). In some versions, tabs (1178a) may be permanently deformed during disengagement from the corresponding recesses (1178b) to render tabs (1178a) incapable of reengaging the corresponding recesses (1178b) such that the ends of device (1120) may be permanently decoupled from each other. In this manner, clasp structures (1150a, 1150b) may serve as single-use decoupling elements. In any event, clasp structures (1150a, 1150b) may provide a convenient means of quickly dismantling the loop by simply pulling clasp structures (1150a, 1150b) away from each other in a single direction.

B. Exemplary Device with Quick Release Clasps at Device Midpoint

Figures 26, 27:
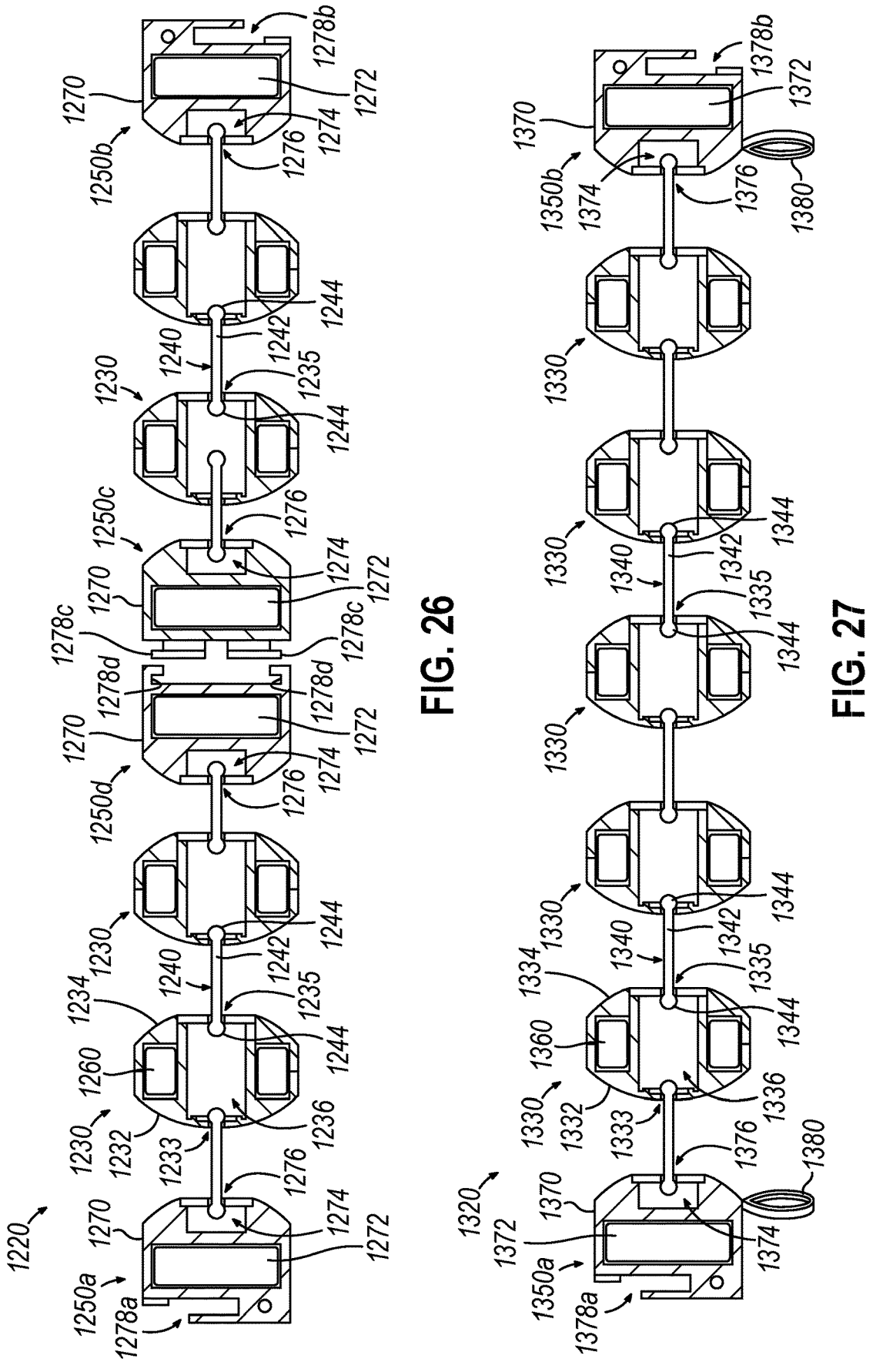
FIG. 26 depicts a top, cross-sectional view of another exemplary sphincter augmentation device, showing clasp structures of the device having quick-release connection elements for coupling midpoints of the device to form a loop.
FIG. 27 depicts a top, cross-sectional view of another exemplary sphincter augmentation device, showing clasp structures of the device having tethers configured to be gripped by an instrument.

FIG. 26 shows another exemplary sphincter augmentation device (1220) including a plurality of beads (1230) and interconnection elements in the form of links (1240). Beads (1230) and links (1240) are similar to beads (30) and links (40) described above, respectively, except as otherwise described below. In this regard, beads (1230) of this example each include a pair of housings (1232, 1234), at least one annular or toroidal rare-earth permanent magnet (1260), a chamber (1236) that is configured to receive a portion of a respective pair of links (1240), and a pair of openings (1233, 1235) at respective ends of chamber (1236). Links (1240) of this example each include a main body in the form of a generally cylindrical wire (1242) with free ends which each terminate in a restriction feature in the form of a ball tip (1244) and movably (e.g., slidably) join together a respective pair of beads (1230).

Sphincter augmentation device (1220) of the present version also includes a first pair of opposing fastener features in the form of complementary clasp structures (1250a, 1250b) coupled to respective beads (1230) via corresponding links (1240) to allow the ends of device (1220) to be coupled together to form a loop, and a second pair of opposing fastener features in the form of first and second quick-release clasp structures (1250c, 1250d) to allow the midpoints of device (1220) to be coupled together to form the loop and/or to allow dismantling of the loop while the ends of device (1220) remain coupled together by clasp structures (1250a, 1250b). In some versions, complementary clasp structures (1250a, 1250b) may be positioned diametrically opposite to quick-release clasp structures (1250c, 1250d). For example, quick-release clasp structures (1250c, 1250d) may be equidistant from complementary clasp structures (1250a, 1250b). In addition, or alternatively, quick-release clasp structures (1250c, 1250d) may be initially coupled to each other by the manufacturer while complementary clasp structures (1250a, 1250b) may be initially decoupled from each other.

Clasp structures (1250a, 1250b, 1250c, 1250d) of this example each include a housing (1270), a disc-shaped rare-earth permanent magnet (1272), a chamber (1274) that is configured to receive a portion of a respective link (1240), an opening (1276) at a respective end of chamber (1274). Clasp structures (1250a, 1250b) also include at least one connection element (1278a, 1278b) configured to mechanically interconnect with the at least one connection element (1278a, 1278b) of the other clasp structure (1250a, 1250b) to resist pulling apart of clasp structures (1250a, 1250b) from each other. In this regard, magnets (1272) of clasp structures (1250a, 1250b) may have a polar alignment such that magnets (1272) of clasp structures (1250a, 1250b) are attracted to each other when connection elements (1278a, 1278b) are interconnected with each other, to thereby help connection elements (1278a, 1278b) become and stay interconnected with each other. In addition to the foregoing, clasp structures (1250a, 1250b) may be constructed and operable in accordance with at least some of the teachings of U.S. Pat. No. 11,071,619, entitled "Coupling Assembly for Implantable Sphincter Assistance Device," U.S. Pat. No. 10,716,570, entitled "Magnetic Restraint Mechanism for a Sphincter Assist Device," and/or U.S. Pub. No. 2011/0098731, now abandoned, entitled "Magnetically Assisted Clasps for Prosthetic Implants, and Related Methods." In some versions, connection elements (1278a, 1278b) are substantially rigid such that clasp structures (1250a, 1250b)

may only be separated from each other via a multi-step separation process in which clasp structures (1250a, 1250b) are pulled apart from each other in multiple directions. For example, when connection elements (1278a, 1278b) are matingly engaged with each other such that the ends of device (1220) are coupled together to form the loop, clasp structures (1250a, 1250b) may initially be pulled away from each other in a first direction (e.g., circumferentially relative to the loop formed by device (1220)) and may subsequently be pulled away from each other in a second direction (e.g., transverse to the first direction) to fully dislodge connection elements (1278a, 1278b) from each other and thereby dismantle the loop.

On the other hand, clasp structures (1250c, 1250d) are configured to be separated from each other via a single-step separation process by simply applying a threshold pulling force between clasp structures (1250c, 1250d) in a single direction. In this regard, first quick-release clasp structure (1250c) includes a pair of quick-release connection elements in the form of flexible tabs (1278c) configured to releasably engage corresponding quick-release connection elements in the form of recesses (1278d) of second quick-release clasp structure (1250d) to thereby couple the midpoints of device (1220) together to form the loop. Magnets (1272) of clasp structures (1250c, 1250d) may have a polar alignment such that magnets (1272) of clasp structures (1250c, 1250d) are attracted to each other when connection elements (1278c, 1278d) are interconnected with each other, to thereby help connection elements (1278c, 1278d) become and stay interconnected with each other. In some versions, tabs (1278c) may be biased outwardly into engagement with the corresponding recesses (1278d). In any event, tabs (1278c) may be selectively urged inwardly out of engagement with the corresponding recesses (1278d) in response to application of a threshold pulling force applied between clasp structures (1250c, 1250d) in a single direction (e.g., circumferentially relative to the loop formed by device (1220)), such as via an instrument, to thereby decouple the midpoints of device (1220). In some versions, tabs (1278c) may be permanently deformed during disengagement from the corresponding recesses (1278d) to render tabs (1278c) incapable of reengaging the corresponding recesses (1278d) such that the midpoints of device (1220) may be permanently decoupled from each other. In this manner, clasp structures (1250c, 1250d) may serve as single-use decoupling elements. In any event, clasp structures (1250c, 1250d) may provide a convenient means of quickly dismantling the loop by simply pulling clasp structures (1250c, 1250d) away from each other in a single direction, such as in cases where performing the multi-step separation process to separate clasp structures (1250a, 1250b) from each other might be difficult or impossible (e.g., due to tissue ingrowth).

C. Exemplary Device with Clasp Tethers for Instrument Gripping

FIG. 27 shows another exemplary sphincter augmentation device (1320) including a plurality of beads (1330) and interconnection elements in the form of links (1340). Beads (1330) and links (1340) are similar to beads (30) and links (40) described above, respectively, except as otherwise described below. In this regard, beads (1330) of this example each include a pair of housings (1332, 1334), at least one annular or toroidal rare-earth permanent magnet (1360), a chamber (1336) that is configured to receive a portion of a respective pair of links (1340), and a pair of openings (1333, 1335) at respective ends of chamber (1336). Links (1340) of this example each include a main body in the form of a generally cylindrical wire (1342) with free ends which each terminate in a restriction feature in the form of a ball tip (1344) and movably (e.g., slidably) join together a respective pair of beads (1330).

Sphincter augmentation device (1320) of the present version also includes opposing fastener features in the form of complementary clasp structures (1350*a*, 1350*b*) coupled to respective beads (1330) via corresponding links (1340) to allow the ends of device (1320) to be coupled together to form a loop. Clasp structures (1350*a*, 1350*b*) of this example each include a housing (1370), a disc-shaped rare-earth permanent magnet (1372), a chamber (1374) that is configured to receive a portion of a respective link (1340), an opening (1376) at a respective end of chamber (1374), and at least one connection element (1378*a*, 1378*b*) configured to mechanically interconnect with the at least one connection element (1378*a*, 1378*b*) of the other clasp structure (1350*a*, 1350*b*) to resist pulling apart of clasp structures (1350*a*, 1350*b*) from each other. In this regard, magnets (1372) may have a polar alignment such that magnets (1372) are attracted to each other when connection elements (1378*a*, 1378*b*) are interconnected with each other, to thereby help connection elements (1378*a*, 1378*b*) become and stay interconnected with each other. In addition to the foregoing, clasp structures (1350*a*, 1350*b*) may be constructed and operable in accordance with at least some of the teachings of U.S. Pat. No. 11,071,619, entitled "Coupling Assembly for Implantable Sphincter Assistance Device," U.S. Pat. No. 10,716,570, entitled "Magnetic Restraint Mechanism for a Sphincter Assist Device," and/or U.S. Pub. No. 2011/0098731, now abandoned, entitled "Magnetically Assisted Clasps for Prosthetic Implants, and Related Methods."

In the example shown, clasp structures (1350*a*, 1350*b*) each include a tether (1380) coupled to housing (1370) and configured to be gripped by an instrument, such as graspers (not shown), for assisting with manipulation of clasp structures (1350*a*, 1350*b*) and device (1320) generally by the instrument. For example, graspers may grip tethers (1380) to manipulate device (1320) during positioning of device (1320) about LES (6). In this regard, tethers (1380) may optionally be interconnected with each other to assist with coupling of clasp structures (1350*a*, 1350*b*) to each other. In some versions, tethers (1380) may be selectively removed from clasp structures (1350*a*, 1350*b*), such as after installation of device (1320) about LES (6). Alternatively, tethers (1380) may be permanently attached to clasp structures (1350*a*, 1350*b*). In the example shown, each tether (1380) is provided in the form of a loop. Each tether (1380) may be constructed of a flexible material, such as a textile. It will be appreciated that each tether (1380) may be constructed of any material suitable for gripping by an instrument.

D. Exemplary Device with Clasp Tabs for Instrument Gripping

Figures 28, 29:
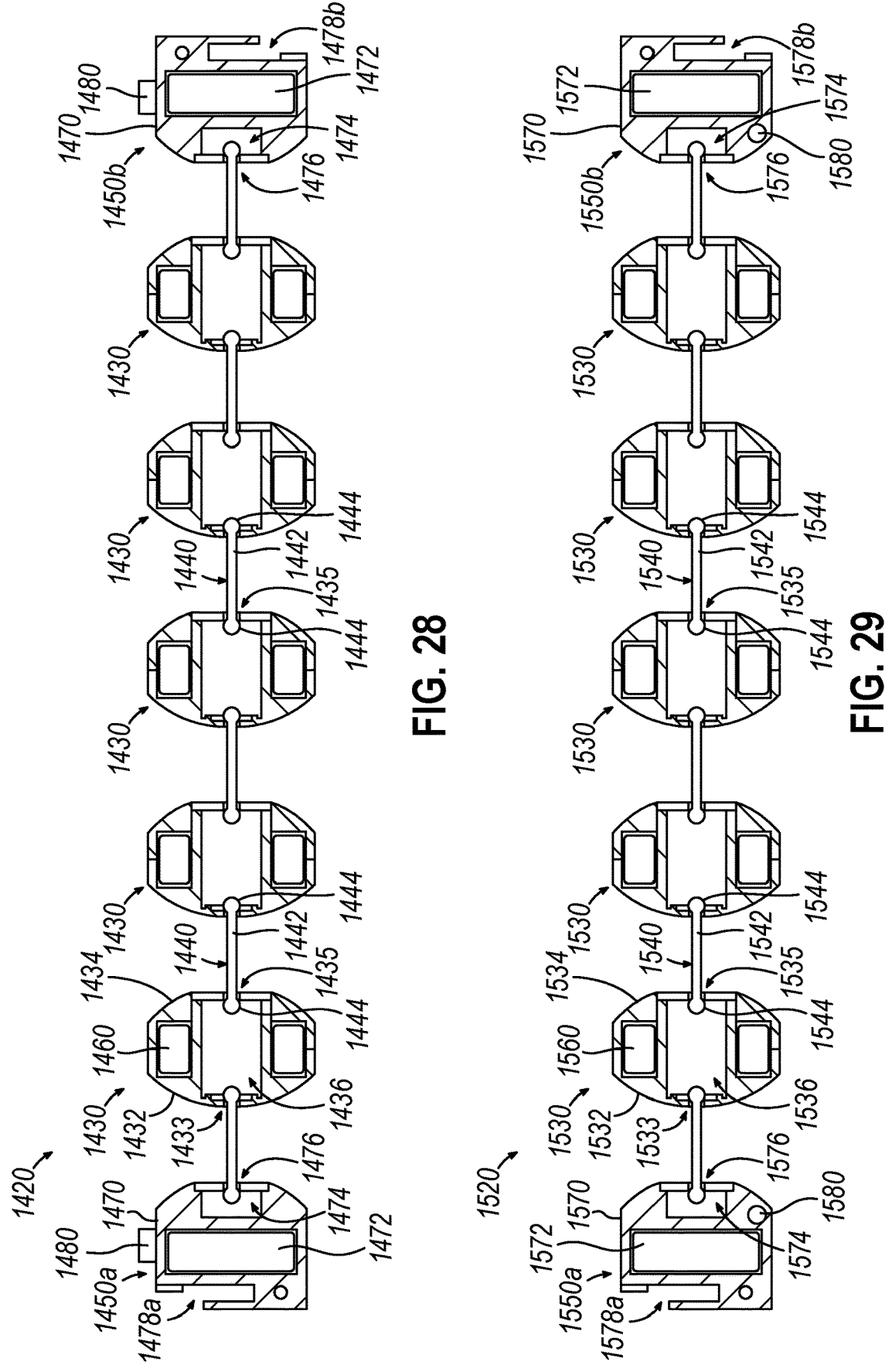
FIG. 28 depicts a top, cross-sectional view of another exemplary sphincter augmentation device, showing clasp structures of the device having tabs configured to be gripped by an instrument.
FIG. 29 depicts a top, cross-sectional view of another exemplary sphincter augmentation device, showing clasp structures of the device having bores configured to be gripped by an instrument.

FIG. 28 shows another exemplary sphincter augmentation device (1420) including a plurality of beads (1430) and interconnection elements in the form of links (1440). Beads (1430) and links (1440) are similar to beads (30) and links (40) described above, respectively, except as otherwise described below. In this regard, beads (1430) of this example each include a pair of housings (1432, 1434), at least one annular or toroidal rare-earth permanent magnet (1460), a chamber (1436) that is configured to receive a portion of a respective pair of links (1440), and a pair of openings (1433,

1435) at respective ends of chamber (1436). Links (1440) of this example each include a main body in the form of a generally cylindrical wire (1442) with free ends which each terminate in a restriction feature in the form of a ball tip (1444) and movably (e.g., slidably) join together a respective pair of beads (1430).

Sphincter augmentation device (1420) of the present version also includes opposing fastener features in the form of complementary clasp structures (1450*a*, 1450*b*) coupled to respective beads (1430) via corresponding links (1440) to allow the ends of device (1420) to be coupled together to form a loop. Clasp structures (1450*a*, 1450*b*) of this example each include a housing (1470), a disc-shaped rare-earth permanent magnet (1472), a chamber (1474) that is configured to receive a portion of a respective link (1440), an opening (1476) at a respective end of chamber (1474), and at least one connection element (1478*a*, 1478*b*) configured to mechanically interconnect with the at least one connection element (1478*a*, 1478*b*) of the other clasp structure (1450*a*, 1450*b*) to resist pulling apart of clasp structures (1450*a*, 1450*b*) from each other. In this regard, magnets (1472) may have a polar alignment such that magnets (1472) are attracted to each other when connection elements (1478*a*, 1478*b*) are interconnected with each other, to thereby help connection elements (1478*a*, 1478*b*) become and stay interconnected with each other. In addition to the foregoing, clasp structures (1450*a*, 1450*b*) may be constructed and operable in accordance with at least some of the teachings of U.S. Pat. No. 11,071,619, entitled "Coupling Assembly for Implantable Sphincter Assistance Device," U.S. Pat. No. 10,716,570, entitled "Magnetic Restraint Mechanism for a Sphincter Assist Device," and/or U.S. Pub. No. 2011/0098731, now abandoned, entitled "Magnetically Assisted Clasps for Prosthetic Implants, and Related Methods."

In the example shown, clasp structures (1450*a*, 1450*b*) each include a tab (1480) coupled to housing (1470) and configured to provide one or more surfaces to be gripped by an instrument, such as graspers (not shown), for assisting with manipulation of clasp structures (1450*a*, 1450*b*) and device (1420) generally by the instrument. For example, graspers may grip any surfaces of tabs (1480) to manipulate device (1420) during positioning of device (1420) about LES (6). In the example shown, each tab (1480) is integrally formed with the respective housing (1470) as a unitary piece. Each tab (1480) may be constructed of a rigid material. In some versions, each tab (1480) may include a textured surface to facilitate gripping by an instrument.

E. Exemplary Device with Clasp Bores for Instrument Gripping

FIG. 29 shows another exemplary sphincter augmentation device (1520) including a plurality of beads (1530) and interconnection elements in the form of links (1540). Beads (1530) and links (1540) are similar to beads (30) and links (40) described above, respectively, except as otherwise described below. In this regard, beads (1530) of this example each include a pair of housings (1532, 1534), at least one annular or toroidal rare-earth permanent magnet (1560), a chamber (1536) that is configured to receive a portion of a respective pair of links (1540), and a pair of openings (1533, 1535) at respective ends of chamber (1536). Links (1540) of this example each include a main body in the form of a generally cylindrical wire (1542) with free ends which each terminate in a restriction feature in the form of a ball tip (1544) and movably (e.g., slidably) join together a respective pair of beads (1530).

Sphincter augmentation device (1520) of the present version also includes opposing fastener features in the form of complementary clasp structures (1550a, 1550b) coupled to respective beads (1530) via corresponding links (1540) to allow the ends of device (1520) to be coupled together to form a loop. Clasp structures (1550a, 1550b) of this example each include a housing (1570), a disc-shaped rare-earth permanent magnet (1572), a chamber (1574) that is configured to receive a portion of a respective link (1540), an opening (1576) at a respective end of chamber (1574), and at least one connection element (1578a, 1578b) configured to mechanically interconnect with the at least one connection element (1578a, 1578b) of the other clasp structure (1550a, 1550b) to resist pulling apart of clasp structures (1550a, 1550b) from each other. In this regard, magnets (1572) may have a polar alignment such that magnets (1572) are attracted to each other when connection elements (1578a, 1578b) are interconnected with each other, to thereby help connection elements (1578a, 1578b) become and stay interconnected with each other. In addition to the foregoing, clasp structures (1550a, 1550b) may be constructed and operable in accordance with at least some of the teachings of U.S. Pat. No. 11,071,619, entitled "Coupling Assembly for Implantable Sphincter Assistance Device," U.S. Pat. No. 10,716,570, entitled "Magnetic Restraint Mechanism for a Sphincter Assist Device," and/or U.S. Pub. No. 2011/0098731, now abandoned, entitled "Magnetically Assisted Clasps for Prosthetic Implants, and Related Methods."

In the example shown, clasp structures (1550a, 1550b) each include a bore (1580) extending at least partially through housing (1570) and configured to be gripped by an instrument, such as graspers (not shown), for assisting with manipulation of clasp structures (1550a, 1550b) and device (1520) generally by the instrument. For example, graspers may grip bores (1580) to manipulate device (1520) during positioning of device (1520) about LES (6).

F. Exemplary Device with Clasp Alignment Indicia

Figures 30, 31:
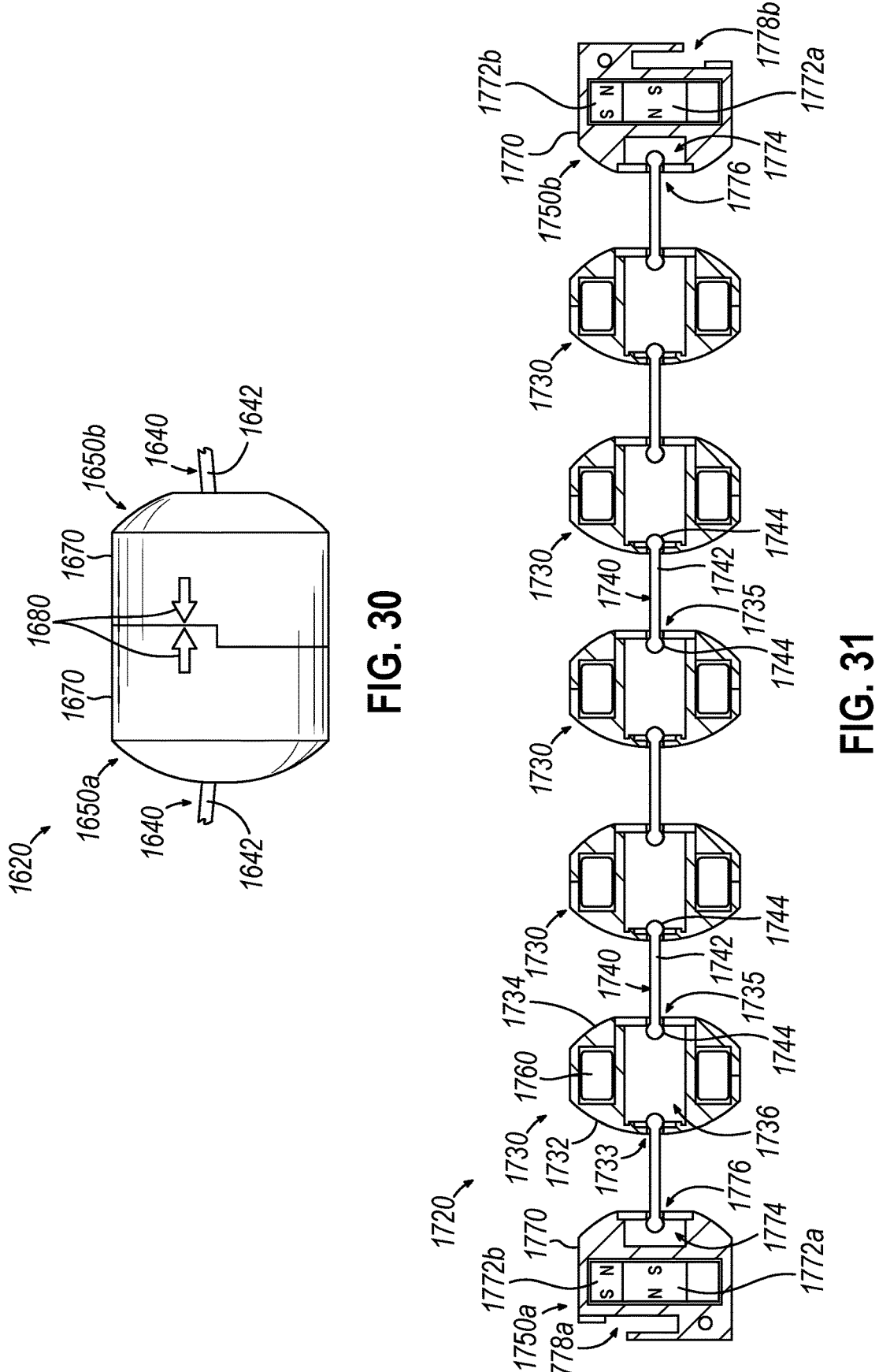
FIG. 30 depicts a perspective view of a portion of another exemplary sphincter augmentation device, showing clasp structures of the device having alignment indicia.
FIG. 31 depicts a top, cross-sectional view of another exemplary sphincter augmentation device, showing clasp structures of the device having a plurality of magnets for axially aligning the clasp structures with each other.

FIG. 30 shows a portion of another exemplary sphincter augmentation device (1620) including a plurality of beads (not shown), such as beads (30), and interconnection elements in the form of links (1640). Links (1640) are similar to links (40) described above, except as otherwise described below. In this regard, links (1640) of this example each include a main body in the form of a generally cylindrical wire (1642) with free ends which each terminate in a restriction feature in the form of a ball tip (not shown) and may be used to movably (e.g., slidably) join together a respective pair of beads (30).

Sphincter augmentation device (1620) of the present version also includes opposing fastener features in the form of complementary clasp structures (1650a, 1650b) which may be coupled to respective beads (30) via corresponding links (1640) to allow the ends of device (1620) to be coupled together to form a loop. Clasp structures (1650a, 1650b) of this example each include a housing (1670), a disc-shaped rare-earth permanent magnet (not shown), a chamber (not shown) that is configured to receive a portion of a respective link (1640), an opening (not shown) at a respective end of the chamber, and at least one connection element (not shown). In addition to the foregoing, clasp structures (1650a, 1650b) may be constructed and operable in accordance with at least some of the teachings of U.S. Pat. No. 11,071,619, entitled "Coupling Assembly for Implantable Sphincter Assistance Device," U.S. Pat. No. 10,716,570, entitled "Magnetic Restraint Mechanism for a Sphincter Assist Device," and/or U.S. Pub. No. 2011/0098731, now abandoned, entitled "Magnetically Assisted Clasps for Prosthetic Implants, and Related Methods."

In the example shown, clasp structures (1650a, 1650b) each include alignment indicia (1680) configured to be aligned with each other to indicate proper initial alignment of clasp structures (1650a, 1650b) and/or a fully latched state of clasp structures (1650a, 1650b) to thereby assist with coupling together of clasp structures (1650a, 1650b). For example, alignment indicia (1680) may each include a printed arrow. In the example shown, clasp structures (1650a, 1650b) may need to be appropriately aligned with each other in order for clasp structures (1650a, 1650b) to be sufficiently engaged with each other to form and maintain the loop. Thus, alignment indicia (1680) may provide visual feedback to the operator to indicate whether appropriate alignment of clasp structures (1650a, 1650b) with each other has been achieved.

G. Exemplary Device with Clasps Having Alignment Magnets

FIG. 31 shows another exemplary sphincter augmentation device (1720) including a plurality of beads (1730) and interconnection elements in the form of links (1740). Beads (1730) and links (1740) are similar to beads (30) and links (40) described above, respectively, except as otherwise described below. In this regard, beads (1730) of this example each include a pair of housings (1732, 1734), at least one annular or toroidal rare-earth permanent magnet (1760), a chamber (1736) that is configured to receive a portion of a respective pair of links (1740), and a pair of openings (1733, 1735) at respective ends of chamber (1736). Links (1740) of this example each include a main body in the form of a generally cylindrical wire (1742) with free ends which each terminate in a restriction feature in the form of a ball tip (1744) and movably (e.g., slidably) join together a respective pair of beads (1730).

Sphincter augmentation device (1720) of the present version also includes opposing fastener features in the form of complementary clasp structures (1750a, 1750b) coupled to respective beads (1730) via corresponding links (1740) to allow the ends of device (1720) to be coupled together to form a loop. Clasp structures (1750a, 1750b) of this example each include a housing (1770), a plurality of rare-earth permanent magnets (1772a, 1772b) that are stacked next to or nested relative to each other within housing (1770), a chamber (1774) that is configured to receive a portion of a respective link (1740), an opening (1776) at a respective end of chamber (1774), and at least one connection element (1778a, 1778b) configured to mechanically interconnect with the at least one connection element (1778a, 1778b) of the other clasp structure (1750a, 1750b) to resist pulling apart of clasp structures (1750a, 1750b) from each other. In this regard, magnets (1772) may have a polar alignment such that magnets (1772) are attracted to each other when connection elements (1778a, 1778b) are interconnected with each other, to thereby help connection elements (1778a, 1778b) become and stay interconnected with each other. In addition to the foregoing, clasp structures (1750a, 1750b) may be constructed and operable in accordance with at least some of the teachings of U.S. Pat. No. 11,071,619, entitled "Coupling Assembly for Implantable Sphincter Assistance Device," U.S. Pat. No. 10,716,570, entitled "Magnetic Restraint Mechanism for a Sphincter Assist Device," and/or U.S. Pub. No. 2011/0098731, now abandoned, entitled "Magnetically Assisted Clasps for Prosthetic Implants, and Related Methods."

In the example shown, magnets (1772a, 1772b) may assist with aligning clasp structures (1750a, 1750b) with each other in a predetermined manner during the process of coupling clasp structures (1750a, 1750b) together. In this regard, each plurality of magnets (1772a, 1772b) includes a central disc-shaped rare-earth permanent magnet (1772a) and at least one outer annular or toroidal rare-earth permanent magnet (1772b). In the example shown, each central magnet (1772a) is relatively larger than each outer magnet (1772a). In some versions, each central magnet (1772a) may present an opposite polarity at the respective end of device (1720) as that presented by the corresponding outer magnet (1772a). Thus, central magnet (1772a) of first clasp structure (1750a) may attract central magnet (1772a) of second clasp structure (1750b), and outer magnet (1772b) of first clasp structure (1750a) may likewise attract outer magnet (1772b) of second clasp structure (1750b). However, central magnet (1772a) of first clasp structure (1750a) may repel outer magnet (1772b) of second clasp structure (1750b), and central magnet (1772a) of second clasp structure (1750b) may likewise repel outer magnet (1772b) of first clasp structure (1750a) to thereby promote axial alignment of clasp structures (1750a, 1750b) with each other.

H. Exemplary Device with Clasp Having Resilient Latching Beam

Figure 32:
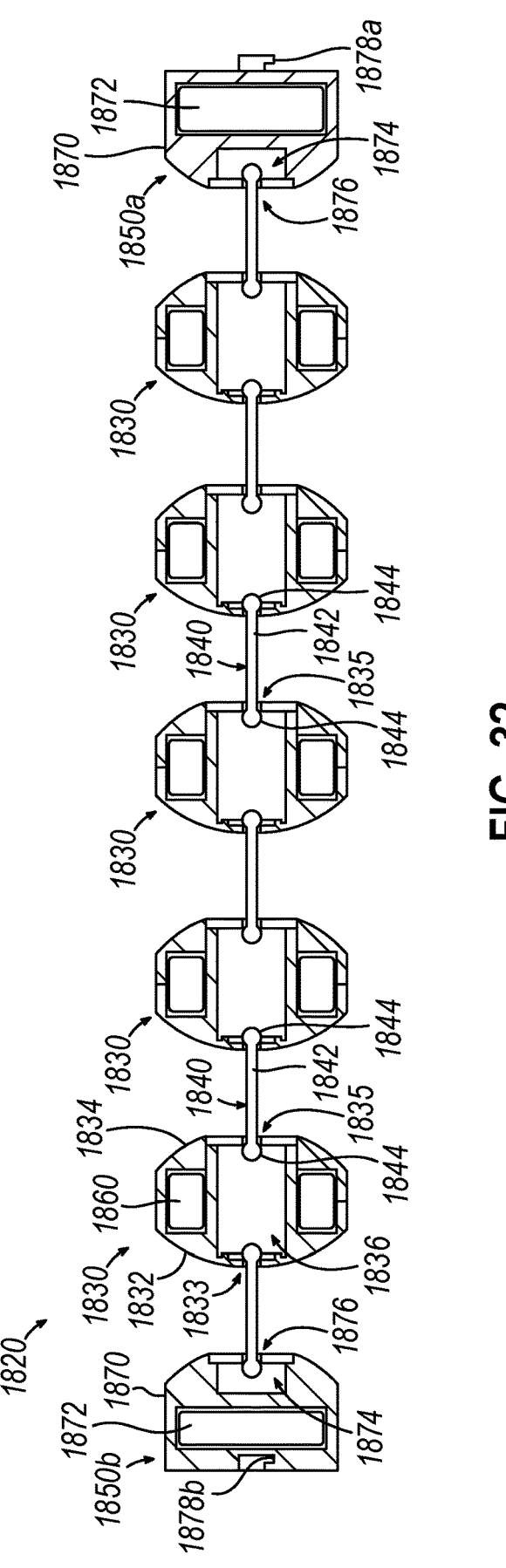
FIG. 32 depicts a top, cross-sectional view of another exemplary sphincter augmentation device, showing clasp structures of the device having a resilient detent and a complementary recess, respectively, for spring biasing the clasp structures together.

FIG. 32 shows another exemplary sphincter augmentation device (1820) including a plurality of beads (1830) and interconnection elements in the form of links (1840). Beads (1830) and links (1840) are similar to beads (30) and links (40) described above, respectively, except as otherwise described below. In this regard, beads (1830) of this example each include a pair of housings (1832, 1834), at least one annular or toroidal rare-earth permanent magnet (1860), a chamber (1836) that is configured to receive a portion of a respective pair of links (1840), and a pair of openings (1833, 1835) at respective ends of chamber (1836). Links (1840) of this example each include a main body in the form of a generally cylindrical wire (1842) with free ends which each terminate in a restriction feature in the form of a ball tip (1844) and movably (e.g., slidably) join together a respective pair of beads (1830).

Sphincter augmentation device (1820) of the present version also includes opposing fastener features in the form of complementary first and second clasp structures (1850a, 1850b) coupled to respective beads (1830) via corresponding links (1840) to allow the ends of device (1820) to be coupled together to form a loop. Clasp structures (1850a, 1850b) of this example each include a housing (1870), a disc-shaped rare-earth permanent magnet (1872), a chamber (1874) that is configured to receive a portion of a respective link (1840), an opening (1876) at a respective end of chamber (1874), and at least one connection element (1878a, 1878b). In this regard, first clasp structure (1850a) includes a connection element in the form of a resilient detent (1878a) configured to releasably engage a corresponding connection element in the form of a complementary recess (1878b) of second clasp structure (1850b) to thereby couple the ends of device (1820) together to form a loop. Magnets (1872) may have a polar alignment such that magnets (1872) are attracted to each other when connection elements (1878a, 1878b) are interconnected with each other, to thereby help connection elements (1878a, 1878b) become and stay interconnected with each other.

In the example shown, detent (1878a) may provide an automatic spring biasing of clasp structures (1850a, 1850b) toward each other when clasp structures (1850a, 1850b) are coupled together and/or in the process of being coupled together (e.g., approximated toward each other). In this regard, detent (1878a) may provide resistance to decoupling of clasp structures (1850a, 1850b) from each other via such spring biasing, which may only be overcome via application of a threshold separation force between clasp structures (1850a, 1850b), such as a threshold pulling force applied between clasp structures (1850a, 1850b) in the circumferential direction (e.g., relative to the loop formed by device (1820)).

I. Exemplary Device with Clasp Having Rotatable Magnet

FIGS. 33A-34B show a portion of another exemplary sphincter augmentation device (1920) including a plurality of beads (not shown), such as beads (30) and interconnection elements in the form of links (not shown), such as links (40).

Sphincter augmentation device (1920) of the present version also includes opposing fastener features in the form of complementary clasp structures (1950a, 1950b) which may be coupled to respective beads (30) via corresponding links (40) to allow the ends of device (1920) to be coupled together to form a loop. Clasp structures (1950a, 1950b) of this example each include a housing (1970), at least one rare-earth permanent magnet (1972a, 1972b, 1972c). In the example shown, magnet (1972a) is annular or toroidal, magnets (1972b, 1972c) are each disc-shaped, and magnet (1972c) is coupled to a rotatable knob (1973) as described in greater detail below). In any event, clasp structures (1950a, 1950b) each further include a chamber (1974) that is configured to receive a portion of a respective link (40), an opening (1976) at a respective end of chamber (1974), and at least one connection element (1978a, 1978b) configured to mechanically interconnect with the at least one connection element (1978a, 1978b) of the other clasp structure (1950a, 1950b) to resist pulling apart of clasp structures (1950a, 1950b) from each other. In this regard, magnets (1972a, 1972b) may have a polar alignment such that magnets (1972a, 1972b) are attracted to each other when connection elements (1978a, 1978b) are interconnected with each other, to thereby help connection elements (1978a, 1978b) become and stay interconnected with each other.

In the example shown, magnet (1972c) is rotatable within housing (1970) of first clasp structure (1950a) via rotation of knob (1973) to reverse the polarity of magnet (1972c) presented at the respective end of device (1920). For example, magnet (1972c) may be rotatable approximately 180° between a first state in which a first pole of magnet (1972c) is presented at the respective end of device (1920) for attracting magnet (1972b) of second clasp structure (1950b) as shown in FIGS. 33A and 34A, and a second state in which a second pole of magnet (1972c) is presented at the respective end of device (1920) for repelling magnet (1972b) of second clasp structure (1950b) as shown in FIGS. 33B and 34B. In this manner, magnet (1972c) may provide an automatic magnetic biasing of clasp structures (1950a, 1950b) toward each other when clasp structures (1950a, 1950b) are coupled together and/or in the process of being coupled together (e.g., approximated toward each other) in the first state, and may assist in decoupling of clasp structures (1950*a*, 1950*b*) from each other in the second state.

J. Exemplary Device with Link Having Release Notch and Beads Having Bailout Beacons FIGS. 29-30 show another exemplary sphincter augmentation device (2020) including a plurality of beads (2030) and interconnection elements in the form of links (2040*a*, 2040*b*). Beads (2030) and links (2040*a*, 2040*b*) are similar to beads (30) and links (40) described above, respectively, except as otherwise described below. In this regard, beads (2030) of this example each include a pair of housings (2032, 2034), at least one annular or toroidal rare-earth permanent magnet (2060), a chamber (2036) that is configured to receive a portion of a respective pair of links (2040*a*, 2040*b*), and a pair of openings (2033, 2035) at respective ends of chamber (2036). Links (2040*a*, 2040*b*) of this example each include a main body in the form of a generally cylindrical wire (2042*a*, 2042*b*) with free ends which each terminate in a restriction feature in the form of a ball tip (2044) and movably (e.g., slidably) join together a respective pair of beads (2030).

In the example shown, the plurality of links (2040*a*, 2040*b*) includes a plurality of first links (2040*a*) each having a solid wire (2042*a*) and at least one second link (2040*b*) having a breakaway wire (2042*b*) with a strategically weakened or frangible region defined by a release notch (2045). Release notch (2045) is configured to facilitate severing of breakaway wire (2042*b*) in response to application of a threshold force thereto. For example, release notch (2045) may be clamped by an instrument, such as graspers (G), to thereby sever breakaway wire (2042*b*). In this manner, breakaway wire (2042*b*) may serve as a single-use decoupling element.

Sphincter augmentation device (1920) of the present version also includes a pair of bailout beacons (2050) positioned on respective beads (2030) that flank second link (2040*b*) such that release notch (2045) is generally centered between bailout beacons (2050). In the example shown, each bailout beacon (2050) is coupled to the corresponding first housing (2032) of the respective bead (2030), and each bailout beacon (2050) and the respective bead (2030) are collectively encased in a conformal coating (2052). In any event, each bailout beacon (2050) is configured to generate a detectable signal(S) indicative of a position of the respective bailout beacon (2050) in three-dimensional space. For example, each bailout beacon (2050) may include a radiofrequency (RF) transmitter configured to generate an RF signal(S) and/or may include an illuminating element (e.g., LED) configured to emit an optical signal(S). In some versions, device (1920) may include an electromagnetic coil that is configured to convert an electromagnetic field into electrical power for driving bailout beacon (2050) to generate such signals(S). In this manner, the signals(S) generated by bailout beacons (2050) may be used to determine a position of release notch (2045) in three-dimensional space.

In this regard, FIG. 30 shows sphincter augmentation device (2020) installed about LES (6) and visually obscured by tissue overgrowth such that release notch (2045) is hidden from view. In order to locate release notch (2045), a clinician may insert an endoscope (E) and/or laparoscope (L) with a corresponding detector (D) into the patient's body. For example, endoscope (E) may be directed toward sphincter augmentation device (2020) via the patient's esophagus (2), while laparoscope (L) may be directed toward sphincter augmentation device (2020) via the patient's thoracic cavity. In any event, detector(s) (D) may be configured to receive the signals(S) generated by bailout beacons (2050) to thereby determine the position of release notch (2045). For example, detector(s) (D) may include an RF receiver configured to receive RF signals(S) generated by bailout beacons (2050) and/or may include a camera or optical sensor configured to receive optical signals(S) emitted by bailout beacons (2050).

In some versions, detector(s) (D) may include a field generator that is operable to generate an electromagnetic field, such that detector(s) (D) can cooperate with the electromagnetic coil of device (1920) to provide wireless transfer of power. In this regard, device (1920) can convert the wirelessly transmitted power into an RF beacon signal that is then read by an RF receiving coil of detector(s) (D). In addition, or alternatively, device (1920) can use the wirelessly transmitted power to illuminate an LED of bailout beacon (2050) that is then picked up by an optical sensor of detector(s) (D). It will be appreciated that if device (2050) is encased in scar tissue, the illumination may still be detected via transillumination through the tissue. In any event, once the position of release notch (2045) has been determined, the clinician may advance graspers (G) (e.g., laparoscopically) toward release notch (2045) and clamp release notch (2045) through the overgrown tissue to thereby sever breakaway wire (2042*b*).

In some versions, sphincter augmentation device (2020) may include an integrated cutting element having a sharp edge (not shown) that is positioned along breakaway wire (2042*b*) of second link (2040*b*) for selectively severing breakaway wire (2042*b*), such as at notch (2045). For example, such an integrated cutting element may be clamped by an instrument, such as graspers (G), to thereby sever breakaway wire (2042*b*). In addition, or alternatively, the conductive metallic surfaces of second link (2040*b*) and/or the beads (2030) that flank second link (2040*b*) may be coated with an insulative material while the conductive metallic surfaces of first links (2040*a*) and/or the remaining beads (2030) may remain exposed to enable differentiation of second link (2040*b*) and/or the beads (2030) that flank second link (2040*b*) from first links (2040*a*) and/or the remaining beads (2030) to thereby determine the position of release notch (2045) in three-dimensional space. For example, such exposed conductive metallic surfaces may promote induction of eddy currents within first links (2040*a*) when captured within the electromagnetic field generated by detector(s) (D) to thereby produce a first magnetic field which may be detected by detector(s) (D), while such insulated surfaces may result in a reduced induction of eddy currents within second link (2040*b*) when captured within the electromagnetic field generated by detector(s) (D) to thereby produce a second magnetic field which may be detected by detector(s) (D) and which is different from the first magnetic field. Such differences between the first and second magnetic fields may assist with differentiating second link (2040*b*) from first links (2040*a*) and thereby assist with locating release notch (2045).

VI. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a plurality of beads, wherein each bead of the plurality of beads comprises: (i) at least one housing, and (ii) at least one magnet positioned within the at least one housing; and (b) a plurality of interconnection elements, wherein each interconnection element of the plurality of interconnection elements movably joins together a corresponding pair of beads of the plurality of beads, wherein at least a portion of each interconnection element of the plurality of interconnection elements comprises at least one composite material; wherein the plurality of beads and the plurality of interconnection elements are sized and configured to form a loop around an anatomical structure in a patient; wherein the loop formed by the plurality of beads and the plurality of interconnection elements is configured to transition between a constricted configuration and an expanded configuration; wherein the loop in the constricted configuration is configured to prevent fluid flow through the anatomical structure; wherein the loop in the expanded configuration is configured to permit fluid flow through the anatomical structure; wherein the magnets are configured to magnetically bias the loop toward the constricted configuration.

Example 2

The apparatus of Example 1, wherein the at least one composite material includes at least one polymer.

Example 3

The apparatus of Example 2, wherein the at least one polymer includes a liquid crystal polymer.

Example 4

The apparatus of any one or more of Examples 1 through 3, wherein each interconnection element of the plurality of interconnection elements comprises: (i) a main body extending between a pair of ends, and (ii) a pair of heads, wherein each head of the pair of heads is positioned at a respective end of the pair of ends.

Example 5

The apparatus of Example 4, wherein the main body comprises the at least one composite material.

Example 6

The apparatus of any one or more of Examples 4 through 5, wherein each head of the pair of heads comprises the at least one composite material.

Example 7

The apparatus of any one or more of Examples 4 through 6, wherein the main body has a first strength, wherein each head of the pair of heads has a second strength greater than the first strength.

Example 8

The apparatus of Example 7, wherein the main body comprises a first material, wherein each head of the pair of heads comprises a second material different from the first material, wherein one of the first or second materials includes the composite material.

Example 9

The apparatus of Example 7, wherein the main body comprises a first form of the composite material, wherein each head of the pair of heads comprises a second form of the composite material different from the first form of the composite material.

Example 10

The apparatus of any one or more of Examples 4 through 9, wherein the main body includes a sheath comprising a plurality of interwoven fibers.

Example 11

The apparatus of any one or more of Examples 4 through 10, wherein the main body includes at least one of a wire or a cable.

Example 12

The apparatus of any one or more of Examples 4 through 11, wherein each head of the pair of heads is molded onto the respective end of the main body.

Example 13

The apparatus of any one or more of Examples 4 through 12, wherein each head of the pair of heads flares outwardly from the respective end of the main body.

Example 14

The apparatus of any one or more of Examples 4 through 13, wherein each head of the pair of heads includes at least one crimped collar.

Example 15

The apparatus of any one or more of Examples 4 through 14, wherein each interconnection element of the plurality of interconnection elements further comprises a rivet having a deformable shaft.

Example 16

An apparatus configured to be implanted within a biological structure, the apparatus comprising: (a) a plurality of beads, wherein each bead of the plurality of beads comprises: (i) at least one housing, and (ii) at least one magnet positioned within the at least one housing; and (b) a plurality of interconnection elements, wherein each interconnection element of the plurality of interconnection elements movably joins together a corresponding pair of beads of the plurality of beads, wherein each interconnection element of the plurality of interconnection elements comprises: (i) a main body extending between a pair of ends and comprising a first material, and (ii) a pair of heads, wherein each head of the pair of heads is positioned at a respective end of the pair of ends and comprises a second material different from the first material.

Example 17

The apparatus of Example 16, wherein the first material includes titanium.

Example 18

The apparatus of any one or more of Examples 16 through 17, wherein the second material includes a polymer.

Example 19

An apparatus configured to be implanted within a biological structure, the apparatus comprising: (a) a plurality of beads, wherein each bead of the plurality of beads comprises: (i) at least one housing, and (ii) at least one magnet positioned within the at least one housing; and (b) a plurality of interconnection elements, wherein each interconnection element of the plurality of interconnection elements movably joins together a corresponding pair of beads of the plurality of beads, wherein each interconnection element of the plurality of interconnection elements comprises: (i) a metallic core extending between a pair of ends, and (ii) a composite sheath positioned over the metallic core.

Example 20

The apparatus of Example 19, wherein each interconnection element of the plurality of interconnection elements further comprises a pair of composite heads, wherein each composite head of the pair of composite heads is positioned at a respective end of the pair of ends.

Example 21

An apparatus comprising: (a) a plurality of beads, wherein each bead of the plurality of beads comprises: (i) at least one housing, and (ii) at least one magnet positioned within the at least one housing; and (b) a plurality of interconnection elements, wherein each interconnection element of the plurality of interconnection elements movably joins together a corresponding pair of beads of the plurality of beads, wherein the plurality of beads and the plurality of interconnection elements are sized and configured to form an expandable loop around an anatomical structure in a patient, wherein the expandable loop is configured to apply at least one constrictive force to the anatomical structure, wherein the at least one constrictive force has a first rate of change when a dilation ratio of the expandable loop is within a first range, a second rate of change when the dilation ratio of the expandable loop is within a second range, and a third rate of change when the dilation ratio of the expandable loop is within a third range.

Example 22

The apparatus of Example 21, wherein the first range is between approximately 0% and approximately 25%, the second range is between approximately 25% and approximately 75%, and the third range is between approximately 75% and approximately 100%.

Example 23

The apparatus of Example 22, wherein the at least one constrictive force includes a first constrictive force generated via the at least one magnet of each bead of the plurality of beads, wherein the first constrictive force is greater within the first and second ranges than within the third range.

Example 24

The apparatus of Example 23, wherein the first constrictive force is greater within the first range than within the second range.

Example 25

The apparatus of Example 24, wherein the second rate of change of the first constrictive force is greater within the second range than within the first range.

Example 26

The apparatus of any one or more of Examples 23 through 25, wherein each bead of the plurality of beads further comprises at least one resilient member positioned within the at least one housing, wherein the at least one constrictive force includes a second constrictive force generated via the at least one resilient member of each bead of the plurality of beads.

Example 27

The apparatus of Example 26, wherein each interconnection element of the plurality of interconnection elements includes at least one cam surface configured to selectively engage the at least one resilient member of each bead of the corresponding pair of beads.

Example 28

The apparatus of Example 27, wherein each interconnection element of the plurality of interconnection elements includes at least one conical head, wherein the at least one cam surface is presented by the at least one conical head.

Example 29

The apparatus of any one or more of Examples 26 through 28, wherein the at least one resilient member is biased toward a radially contracted state.

Example 30

The apparatus of any one or more of Examples 26 through 29, wherein the at least one resilient member includes at least one coil spring.

Example 31

The apparatus of Example 30, wherein the at least one coil spring is slanted.

Example 32

The apparatus of any one or more of Examples 30 through 31, wherein the at least one coil spring is toroidal.

Example 33

The apparatus of any one or more of Examples 26 through 32, wherein the first constrictive force is greater than the second constrictive force when the dilation ratio is within the first range.

Example 34

The apparatus of any one or more of Examples 26 through 33, wherein the first constrictive force is equal to the second constrictive force when the dilation ratio is within the second range.

Example 35

The apparatus of any one or more of Example 26 through 34, wherein the first constrictive force is less than the second constrictive force when the dilation ratio is within the third range.

Example 36

An apparatus configured to be implanted within a biological structure, the apparatus comprising: (a) a plurality of beads, wherein each bead of the plurality of beads comprises: (i) at least one housing, (ii) at least one magnet positioned within the at least one housing, and (iii) at least one annular resilient member positioned within the at least one housing; and (b) a plurality of interconnection elements, wherein each interconnection element of the plurality of interconnection elements movably joins together a corresponding pair of beads of the plurality of beads and is at least partially disposed within the at least one annular resilient member of each bead of the corresponding pair of beads.

Example 37

The apparatus of Example 36, wherein each interconnection element of the plurality of interconnection elements includes at least one cam surface configured to radially expand the at least one annular resilient member.

Example 38

The apparatus of Example 37, wherein each interconnection element of the plurality of interconnection elements includes at least one conical head, wherein the at least one cam surface is presented by the at least one conical head.

Example 39

The apparatus of any one or more of Examples 36 through 38, wherein the at least one annular resilient member includes at least one toroidal coil spring.

Example 40

An apparatus configured to be implanted within a biological structure, the apparatus comprising: (a) a plurality of beads, wherein each bead of the plurality of beads comprises: (i) at least one housing, and (ii) at least one magnet positioned within the at least one housing; and (b) a plurality of interconnection elements, wherein each interconnection element of the plurality of interconnection elements movably joins together a corresponding pair of beads of the plurality of beads, wherein each interconnection element of the plurality of interconnection elements comprises an elastic composite material.

Example 41

An apparatus comprising: (a) a plurality of beads, wherein each bead of the plurality of beads comprises: (i) at least one housing, and (ii) at least one magnet positioned within the at least one housing; and (b) a plurality of interconnection elements, wherein each interconnection element of the plurality of interconnection elements movably joins together a corresponding pair of beads of the plurality of beads, wherein each interconnection element of the plurality of interconnection elements comprises: (i) a main body extending between a pair of ends, and (ii) a pair of heads, wherein each head of the pair of heads is positioned at a respective end of the pair of ends and received within a corresponding bead of the plurality of beads, wherein the plurality of beads and the plurality of interconnection elements are sized and configured to form a loop around an anatomical structure in a patient; wherein the loop formed by the plurality of beads and the plurality of interconnection elements is configured to transition between a constricted configuration and an expanded configuration; wherein the loop in the constricted configuration is configured to prevent fluid flow through the anatomical structure; wherein the loop in the expanded configuration is configured to permit fluid flow through the anatomical structure; wherein the apparatus is configured such that, when the loop is in the expanded configuration, a first head of a first interconnection element of the plurality of interconnection elements is received within a first bead of the plurality of beads and is spaced apart from a first centerline of the first bead by a first distance, and a second head of a second interconnection element of the plurality of interconnection elements is received within a second bead of the plurality of beads and is spaced apart from a second centerline of the second bead by a second distance different from the first distance.

Example 42

The apparatus of Example 41, wherein the first interconnection element has a first length, wherein the second interconnection element has a second length different from the first length.

Example 43

The apparatus of Example 42, wherein the first and second interconnection elements are adjacent to each other.

Example 44

The apparatus of any one or more of Examples 42 through 43, wherein the first length is approximately 0.140 inch.

Example 45

The apparatus of Example 44, wherein the second length is approximately 0.100 inch.

Example 46

The apparatus of any one or more of Examples 42 through 44, wherein the second length is greater than the first length, wherein the second interconnection element is pre-bent to form an obtuse angle.

Example 47

The apparatus of any one or more of Examples 41 through 46, wherein the first bead has a first length, wherein the second bead has a second length different from the first length.

Example 48

The apparatus of any one or more of Examples 41 through 47, wherein the first bead has a first diameter at the first centerline, wherein the second bead has a second diameter at the second centerline different from the first diameter.

Example 49

The apparatus of any one or more of Examples 41 through 48, wherein the first bead has a first bead size, wherein the second bead has a second bead size different from the first bead size.

Example 50

The apparatus of Example 49, wherein the at least one magnet positioned within the at least one housing of the first bead has a first magnet size, wherein the at least one magnet positioned within the at least one housing of the second bead has a second magnet size different from the first magnet size.

Example 51

The apparatus of any one or more of Examples 41 through 50, wherein each bead of the plurality of beads is asymmetric about a respective centerline of the bead.

Example 52

The apparatus of Example 51, wherein each bead of the plurality of beads includes a convex side and a chamfered side.

Example 53

The apparatus of Example 52, wherein the chamfered side of each bead of the plurality of beads is configured to abut the convex side of an adjacent bead of the plurality of beads.

Example 54

The apparatus of any one or more of Examples 41 through 53, wherein the first head is received within the first bead at a first position, wherein the second head is received within the second bead at a second position radially offset from the first position.

Example 55

The apparatus of any one or more of Examples 41 through 54, wherein the magnets are configured to magnetically bias the loop toward the constricted configuration.

Example 56

An apparatus configured to be implanted within a biological structure, the apparatus comprising: (a) a plurality of beads, wherein each bead of the plurality of beads comprises: (i) at least one housing, and (ii) at least one magnet positioned within the at least one housing; and (b) a plurality of interconnection elements, wherein each interconnection element of the plurality of interconnection elements movably joins together a corresponding pair of beads of the plurality of beads, wherein the plurality of interconnection elements includes a first interconnection element having a first length and a second interconnection element having a second length different from the first length.

Example 57

The apparatus of Example 56, wherein the first length is approximately 0.140 inch, wherein the second length is approximately 0.100 inch.

Example 58

The apparatus of Example 56, wherein the second length is greater than the first length, wherein the second interconnection element is pre-bent to form an obtuse angle.

Example 59

An apparatus comprising: (a) a plurality of beads, wherein each bead of the plurality of beads comprises: (i) at least one housing, and (ii) at least one magnet positioned within the at least one housing; and (b) a plurality of interconnection elements, wherein each interconnection element of the plurality of interconnection elements movably joins together a corresponding pair of beads of the plurality of beads, wherein the plurality of beads and the plurality of interconnection elements are sized and configured to form a loop around an anatomical structure in a patient; wherein the loop formed by the plurality of beads and the plurality of interconnection elements is configured to transition between a constricted configuration and an expanded configuration; wherein the loop in the constricted configuration is configured to prevent fluid flow through the anatomical structure; wherein the loop in the expanded configuration is configured to permit fluid flow through the anatomical structure; wherein the apparatus is configured such that, when the loop is in the expanded configuration, each bead of the plurality of beads is spaced apart from a corresponding adjacent bead of the plurality of beads by one of a first gap or a second gap different from the first gap, wherein the first and second gaps alternate circumferentially relative to the loop.

Example 60

The apparatus of Example 59, wherein the plurality of interconnection elements includes a plurality of first interconnection elements having a first length and a plurality of second interconnection elements having a second length different from the first length, wherein the first and second interconnection elements alternate circumferentially relative to the loop.

Example 61

An apparatus comprising: (a) a plurality of beads, wherein each bead of the plurality of beads comprises: (i) at least one housing, and (ii) at least one magnet positioned within the at least one housing; (b) a plurality of interconnection elements, wherein each interconnection element of the plurality of interconnection elements movably joins together a corresponding pair of beads of the plurality of beads, wherein the plurality of beads and the plurality of interconnection elements are sized and configured to form an expandable loop around an anatomical structure in a patient; and (c) at least one decoupling element, wherein the at least one decoupling element is positioned along the loop and is configured to selectively release a first portion of the loop from a second portion of the loop in response to application of a threshold force to the at least one decoupling element in a circumferential direction relative to the loop.

Example 62

The apparatus of Example 61, wherein the at least one decoupling element includes a weakened portion of an interconnection element of the plurality of interconnection elements, wherein the weakened portion is configured to be severed in response to application of the threshold force to the weakened portion.

Example 63

The apparatus of Example 62, wherein the weakened portion is defined by a release notch provided along the respective interconnection element.

Example 64

The apparatus of Example 61, wherein the at least one decoupling element includes first and second quick-release clasp structures selectively coupled to each other, wherein the first and second quick-release clasp structures are configured to be separated from each other in response to application of the threshold force to a portion of at least one of the first or second quick-release clasp structures in the circumferential direction.

Example 65

The apparatus of Example 64, wherein one of the first or second quick-release clasp structures includes a tab.

Example 66

The apparatus of Example 65, wherein the other of the first or second quick-release clasp structures includes a recess configured to disengage the tab in response to application of the threshold force to at least one of the tab or the recess.

Example 67

The apparatus of Example 66, wherein the tab is configured to be permanently deformed during disengagement of the tab from the recess.

Example 68

The apparatus of Example 61, wherein the at least one decoupling element includes a rotatable magnet.

Example 69

The apparatus of any one or more of Examples 61 through 68, wherein the at least one decoupling element includes a pair of decoupling elements positioned at respective ends of the apparatus.

Example 70

The apparatus of any one or more of Examples 61 through 69, wherein the at least one decoupling element includes a pair of decoupling elements positioned at a midpoint of the apparatus.

Example 71

The apparatus of any one or more of Examples 61 through 70, further comprising at least one bailout beacon configured to generate a signal indicating a position of the at least one decoupling element in three dimensional space.

Example 72

The apparatus of Example 71, wherein the signal includes a radiofrequency signal.

Example 73

The apparatus of any one or more of Examples 71 through 72, wherein the signal includes an optical signal.

Example 74

The apparatus of any one or more of Examples 71 through 73, wherein the at least one bailout beacon includes a pair of bailout beacons flanking the at least one decoupling element.

Example 75

The apparatus of any one or more of Examples 71 through 74, wherein the at least one bailout beacon is coupled to at least one bead of the plurality of beads.

Example 76

An apparatus comprising: (a) a plurality of beads, wherein each bead of the plurality of beads comprises: (i) at least one housing, and (ii) at least one magnet positioned within the at least one housing; and (b) a plurality of interconnection elements, wherein each interconnection element of the plurality of interconnection elements movably joins together a corresponding pair of beads of the plurality of beads, wherein the plurality of beads and the plurality of interconnection elements are sized and configured to form an expandable loop around an anatomical structure in a patient, wherein at least one interconnection element of the plurality of interconnection elements includes a breakaway wire.

Example 77

The apparatus of Example 76, wherein the breakaway wire includes a weakened portion, wherein the weakened portion is configured to be severed in response to application of a threshold force to the weakened portion.

Example 78

The apparatus of Example 77, wherein the weakened portion is defined by a release notch provided along the breakaway wire.

Example 79

An apparatus configured to be implanted within a biological structure, the apparatus comprising: (a) a plurality of beads, wherein each bead of the plurality of beads comprises: (i) at least one housing, and (ii) at least one magnet positioned within the at least one housing; (b) a plurality of interconnection elements, wherein each interconnection element of the plurality of interconnection elements movably joins together a corresponding pair of beads of the plurality of beads; (c) a first pair of clasp structures positioned at respective ends of the apparatus and configured to selectively couple with each other; and (d) a second pair of clasp structures configured to be separated from each other in response to application of a threshold force to a portion of at least one of the second pair of clasp structures.

Example 80

The apparatus of Example 79, wherein the second pair of clasp structures are positioned at a midpoint of the apparatus.

VII. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a plurality of beads, wherein each bead of the plurality of beads comprises:
      (i) at least one housing,
      (ii) at least one magnet positioned within the at least one housing, and
      (iii) at least one resilient member positioned within the at least one housing; and
   (b) a plurality of interconnection elements, wherein each interconnection element of the plurality of interconnection elements movably joins together a corresponding pair of beads of the plurality of beads, wherein the plurality of beads and the plurality of interconnection elements are sized and configured to form an expandable loop around an anatomical structure in a patient,
   wherein the plurality of beads is configured to apply at least one constrictive force, wherein the at least one constrictive force includes at least one of:
      (i) a first constrictive force generated via the at least one magnet of each bead of the plurality of beads; or
      (ii) a second constrictive force generated via the at least one resilient member of each bead of the plurality of beads;
   wherein the at least one resilient member is configured to engage a respective interconnection element to thereby apply the second constrictive force of the at least one constrictive force;
   wherein the expandable loop is configured to apply the at least one constrictive force to the anatomical structure, wherein the at least one constrictive force has a first rate of change when a dilation ratio of the expandable loop is within a first range, a second rate of change when the dilation ratio of the expandable loop is within a second range, and a third rate of change when the dilation ratio of the expandable loop is within a third range, and wherein the dilation ratio is a ratio of a current size of the expandable loop relative to a maximum size of the expandable loop;
   wherein the first range of the dilation ratio is between approximately 0% and approximately 25%, the second range of the dilation ratio is between approximately 25% and approximately 75%, and the third range of the dilation ratio is between approximately 75% and approximately 100%; and
   wherein the first constrictive force is greater when the dilation ratio is within the first and second ranges than within the third range.

2. The apparatus of claim 1, wherein the first constrictive force is greater when the dilation ratio is within the first range than within the second range.

3. The apparatus of claim 2, wherein the second rate of change of the at least one constrictive force is greater within the second range than within the first range.

4. The apparatus of claim 1, wherein each interconnection element of the plurality of interconnection elements includes at least one cam surface configured to selectively engage the at least one resilient member of each bead of the corresponding pair of beads.

5. The apparatus of claim 4, wherein each interconnection element of the plurality of interconnection elements includes at least one conical head, and wherein the at least one cam surface is presented by the at least one conical head.

6. The apparatus of claim 1, wherein the at least one resilient member is biased toward a radially contracted state.

7. The apparatus of claim 1, wherein the at least one resilient member includes at least one coil spring.

8. The apparatus of claim 7, wherein the at least one coil spring is slanted.

9. The apparatus of claim 7, wherein the at least one coil spring is toroidal.

10. The apparatus of claim 1, wherein the first constrictive force is greater than the second constrictive force when the dilation ratio is within the first range.

11. The apparatus of claim 1, wherein the first constrictive force is equal to the second constrictive force when the dilation ratio is within the second range.

12. The apparatus of claim 1, wherein the first constrictive force is less than the second constrictive force when the dilation ratio is within the third range.

13. An apparatus configured to be implanted within a biological structure, the apparatus comprising:

(a) a plurality of beads, wherein each bead of the plurality of beads comprises:
(i) at least one housing,
(ii) at least one magnet positioned within the at least one housing, and
(iii) at least one annular resilient member positioned within the at least one housing, and wherein the at least one annular resilient member includes at least one toroidal coil spring; and
(b) a plurality of interconnection elements, wherein each interconnection element of the plurality of interconnection elements movably joins together a corresponding pair of beads of the plurality of beads, and wherein each interconnection element is disposed within the at least one annular resilient member of each bead of the corresponding pair of beads.

14. The apparatus of claim 13, wherein each interconnection element of the plurality of interconnection elements includes at least one cam surface configured to radially expand the at least one annular resilient member.

15. The apparatus of claim 14, wherein each interconnection element of the plurality of interconnection elements includes at least one conical head, and wherein the at least one cam surface is presented by the at least one conical head.

16. An apparatus configured to be implanted within a biological structure, the apparatus comprising:

(a) a plurality of beads, wherein each bead of the plurality of beads comprises:
(i) at least one housing,
(ii) at least one magnet positioned within the at least one housing, and
(iii) at least one annular resilient member positioned within the at least one housing, and wherein the at least one annular resilient member includes at least one toroidal coil spring; and
(b) a plurality of interconnection elements, wherein each interconnection element of the plurality of interconnection elements movably joins together a corresponding pair of beads of the plurality of beads, wherein each interconnection element of the plurality of interconnection elements comprises an elastic composite material, and wherein each interconnection element is disposed within the at least one annular resilient member of each bead of the corresponding pair of beads.

* * * * *